United States Patent
Holguin et al.

(10) Patent No.: US 7,019,067 B2
(45) Date of Patent: Mar. 28, 2006

(54) POLYMER POWDERS, PRESSURE SENSITIVE ADHESIVES AND METHODS OF MAKING THE SAME

(75) Inventors: Daniel L. Holguin, Fullerton, CA (US); H. Paul Barker, Sherman Oaks, CA (US); Kenneth S. Lin, San Marino, CA (US)

(73) Assignee: Avery Dennison Corporation, Pasadena, CA (US)

( * ) Notice: Subject to any disclaimer, the term of this patent is extended or adjusted under 35 U.S.C. 154(b) by 0 days.

(21) Appl. No.: 10/799,500

(22) Filed: Mar. 12, 2004

(65) Prior Publication Data

US 2004/0266965 A1 Dec. 30, 2004

Related U.S. Application Data

(63) Continuation of application No. 10/133,808, filed on Apr. 26, 2002, now Pat. No. 6,743,880, which is a continuation-in-part of application No. 09/757,980, filed on Jan. 10, 2001, now Pat. No. 6,653,427, which is a continuation-in-part of application No. 09/540,252, filed on Mar. 31, 2000, now Pat. No. 6,706,836, application No. 10/799,500, and a continuation of application No. 09/540,252, filed on Mar. 31, 2000, now Pat. No. 6,706,836.

(51) Int. Cl.
*C08F 4/04* (2006.01)

(52) U.S. Cl. .................. 524/558; 526/91; 526/320

(58) Field of Classification Search ............... 524/558; 526/91, 320
See application file for complete search history.

(56) References Cited

U.S. PATENT DOCUMENTS

| | | | |
|---|---|---|---|
| 2,976,576 A | 3/1961 | Wichterle et al. | |
| 3,220,960 A | 11/1965 | Wichterle et al. | |
| 3,567,760 A | 3/1971 | Feldman et al. | |
| 3,576,760 A | 4/1971 | Gould et al. | |
| 3,784,540 A * | 1/1974 | Kliment et al. | 526/320 |
| 3,813,695 A | 6/1974 | Podell, Jr. et al. | |
| 3,860,490 A * | 1/1975 | Guttag | 435/182 |
| 3,963,685 A | 6/1976 | Abrahams | |
| 4,140,115 A | 2/1979 | Schonfeld | |
| 4,243,719 A * | 1/1981 | Holmes | 340/550 |
| 4,275,138 A | 6/1981 | Kita et al. | |
| 4,303,066 A | 12/1981 | D'Andrea | |
| 4,356,288 A | 10/1982 | Lewis et al. | |
| 4,379,863 A | 4/1983 | Snyder | |
| 4,482,577 A | 11/1984 | Goldstein et al. | |
| 4,499,154 A | 2/1985 | James et al. | |
| 4,548,845 A | 10/1985 | Parsons et al. | |
| 4,563,184 A | 1/1986 | Korol | |
| 4,575,476 A | 3/1986 | Podell et al. | |
| 4,593,053 A | 6/1986 | Jevne et al. | |
| 4,732,786 A | 3/1988 | Patterson et al. | |
| 4,768,523 A | 9/1988 | Cahalan et al. | |
| 4,812,549 A | 3/1989 | Muramoto et al. | |
| 4,892,787 A | 1/1990 | Kruse et al. | |
| 4,904,749 A | 2/1990 | Brusky et al. | |
| 4,935,307 A | 6/1990 | Iqbal et al. | |
| 4,994,267 A | 2/1991 | Sablotsky | |
| 5,034,154 A | 7/1991 | Yezrielev et al. | |
| 5,190,805 A | 3/1993 | Atherton et al. | |
| 5,206,071 A | 4/1993 | Atherton et al. | |
| 5,225,473 A | 7/1993 | Duan | |

(Continued)

FOREIGN PATENT DOCUMENTS

DE 19516111 A1 11/1996
EP 024164 A1 2/1981

(Continued)

OTHER PUBLICATIONS

Polymer International, vol. 36, No. 4, p. 303-308 (Apr. 1995).

(Continued)

*Primary Examiner*—Bernard Lipman
(74) *Attorney, Agent, or Firm*—Curatolo Sidoti Co., LPA; Joseph G. Curatolo; Salvatore A. Sidoti

(57) ABSTRACT

A method for making hydrophilic homopolymers and copolymers of poly 2-hydroxyethyl methacrylate. Also disclosed are coatings, films, hydrogels, cosmetic compositions, dermatological compositions, pressure sensitive adhesives containing the hydrophilic homopolymers or copolymers of poly 2-hydroxyethylmethacrylate. Further disclosed are methods of coating substrates with the hydrophilic homopolymers and copolymers of poly 2-hydroxyethyl methacrylate and hydrophilic pressure sensitive adhesives.

27 Claims, 2 Drawing Sheets

U.S. PATENT DOCUMENTS

| | | | |
|---|---|---|---|
| 5,336,208 A | | 8/1994 | Rosenbluth et al. |
| 5,478,631 A | | 12/1995 | Kawano et al. |
| 5,508,366 A | | 4/1996 | Andrist et al. |
| 5,516,865 A | | 5/1996 | Urquiola |
| 5,523,076 A | * | 6/1996 | Schoon .................. 424/61 |
| 5,580,565 A | | 12/1996 | Tighe et al. |
| 5,601,723 A | | 2/1997 | Kirk et al. |
| 5,665,477 A | | 9/1997 | Meathrel et al. |
| 5,672,392 A | | 9/1997 | De Clercq et al. |
| 5,695,484 A | | 12/1997 | Cox |
| 5,700,585 A | | 12/1997 | Lee |
| 5,712,346 A | | 1/1998 | Lee |
| 6,461,340 B1 | | 10/2002 | Lenker et al. |
| 6,653,427 B1 | * | 11/2003 | Holguin ................. 526/320 |
| 6,706,836 B1 | * | 3/2004 | Holguin et al. ......... 526/320 |
| 6,743,880 B1 | * | 6/2004 | Holguin ................. 526/320 |

FOREIGN PATENT DOCUMENTS

| | | | |
|---|---|---|---|
| EP | 0716929 A1 | | 6/1996 |
| JP | 63-227682 | * | 3/1987 |
| JP | 2-22302 A | | 1/1990 |
| JP | 9-241596 | * | 9/1997 |
| WO | WO 92/11825 | | 7/1992 |
| WO | WO 99/06454 | | 2/1999 |

OTHER PUBLICATIONS

Chang, et al. "Avery Adhesive Test, AAT," Adhesive Age, vol. 40, No. 10, p. 18-23 (1997).

E.P. Chang, "Visoelastic Windows of Pressure-Sensitive Adhesives," J. Adhesion, vol. 34, p. 189-200 (1991).

E.P. Chang, "Visoelastic Properties of Pressure-Sensitive Adhesives," J. Adhesion, p. 233-248 (1997).

* cited by examiner

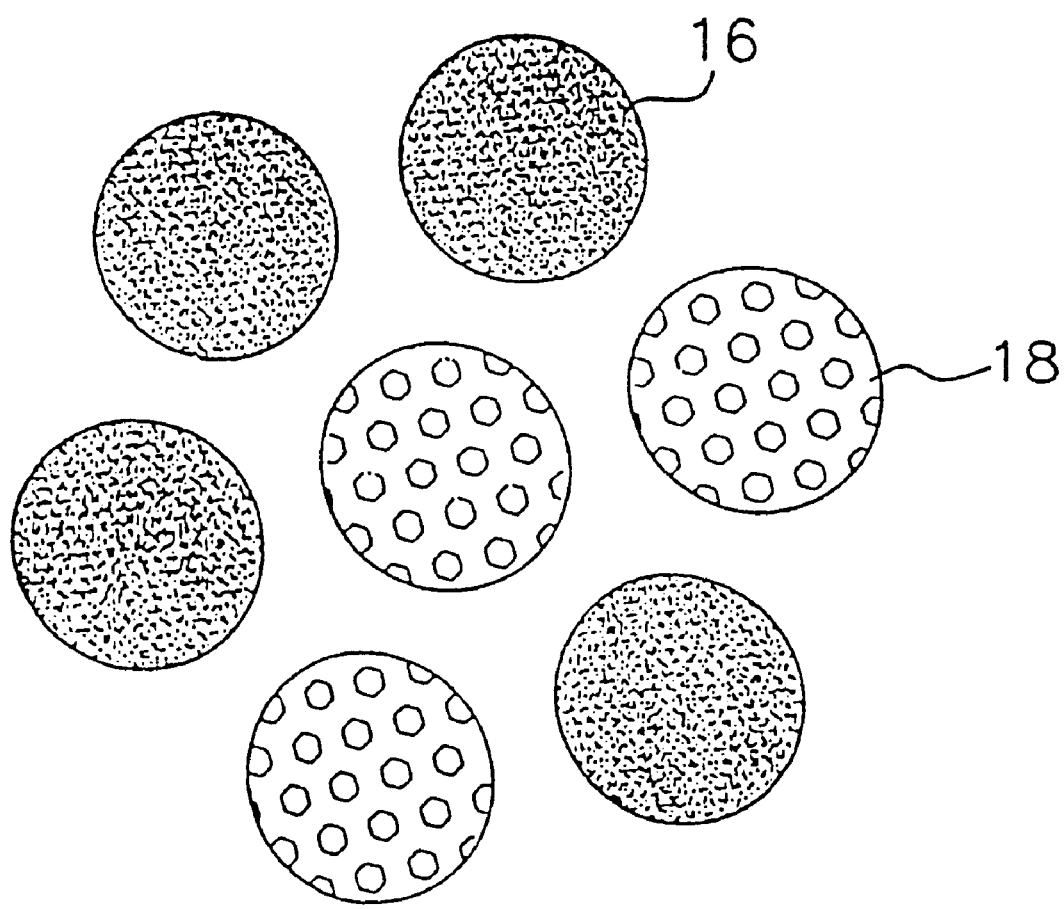

POLYMER POWDERS, PRESSURE SENSITIVE ADHESIVES AND METHODS OF MAKING THE SAME

CROSS REFERENCE TO RELATED APPLICATIONS

The present application is a continuation of U.S. Ser. No. 10/133,808, filed on Apr. 26, 2002, now U.S. Pat. No. 6,743,880, which is a continuation-in-part of U.S. Ser. No. 09/757,980, filed on Jan. 10, 2001, now U.S. Pat. No. 6,653,427, which is a continuation-in-part of U.S. Ser. No. 09/540,252, filed on Mar. 31, 2000, now U.S. Pat. No. 6,706,836. The present application is also a continuation of U.S. Ser. No. 09/540,252, filed on Mar. 31, 2000, now U.S. Pat. No. 6,706,836. Each of U.S. Ser. Nos. 09/540,252, 09/757,980, and 10/133,808 are incorporated herein by reference.

FIELD OF THE INVENTION

This invention is related to the method of preparing hydrophilic poly 2-hydroxyethyl methacrylate homopolymers and copolymers and to their use as pressure sensitive adhesives, hydrogels, coatings, and compositions suitable for topical application to skin.

BACKGROUND OF THE INVENTION

The family of synthetic hydrophilic polymers includes polyacrylic acid, polyvinyl pyrrolidone, polyvinyl alcohol, polyacrylamide, poly hydroxybutyl acrylate, and poly 2-hydroxyethyl methacrylate. In this family of synthetic hydrophilic polymers, poly 2-hydroxyethyl methacrylate and poly hydroxybutyl acrylate are water insoluble polymers prepared from a water soluble monomer. The other polymers require crosslinking to form a water insoluble polymer.

2-Hydroxyethyl methacrylate polymers are of interest because of their biocompatibility, as evidenced by excellent performance in animal implant studies. The extensive use of 2-hydroxyethyl methacrylate polymers for contact lenses for the eyes illustrates the non irritating nature of the polymers.

Other than commercial use in contact lenses, 2-hydroxyethyl methacrylate polymers have had limited commercial success, used at low percentages only, because of the nature of the monomer. Industrial grade 2-hydroxyethyl methacrylate monomer contains a small amount of crosslinker impurity which can cause gel formation during solvent polymerization. The 2-hydroxyethyl methacrylate monomer is water soluble and the 2-hydroxyethyl methacrylate polymer is water insoluble which causes difficulty in emulsion polymerization employing a high portion of 2-hydroxyethyl methacrylate monomer. The preparation of 2-hydroxyethyl methacrylate polymer therefore generally requires the use of very pure and expensive monomer, having ethylene glycol dimethacrylate impurities less than 0.035 weight percent, based on the weight of the monomer, or a very extensive and expensive polymerization process.

Requirements of high quality inkjet coatings include clarity, water resistance, good ink absorption with quick drying, and low surface friction to enhance sheet feeding in inkjet printers. Typical inkjet coatings satisfy the requirements of water resistance, good ink absorption with quick drying, and low surface friction through the use of mixtures of polymers, or polymers with pigments, however, these mixtures are not clear.

U.S. Pat. No. 2,976,576 describes the use of poly 2-hydroxyethyl methacrylate resin for contact lenses and body implants.

U.S. Pat. No. 3,220,960 describes the use of poly 2-hydroxyethyl methacrylate resin for contact lenses and body implants.

U.S. Pat. No. 3,567,760 describes the preparation of 2-hydroxyethyl methacrylate copolymers in methanol that are water soluble salts for entrapping drugs, pesticides, flavoring agents, and fragrances.

U.S. Pat. No. 3,963,685 describes the preparation of methanol soluble poly 2-hydroxyethyl methacrylate for wound care dressings using high purity 2-hydroxyethyl methacrylate monomer having not over 0.035 weight percent of alkylene glycol dimethacrylate impurities.

EP 024164A1 describes the preparation of methanol soluble poly 2-hydroxyethyl methacrylate using high purity 2-hydroxyethyl methacrylate monomer.

Polymer International, vol. 36 no. 4, pp.303–308 (April 1995), describes the preparation of dimethylformamide soluble poly 2-hydroxyethyl methacrylate using a chain transfer agent to prevent gellation.

U.S. Pat. No. 4,303,066 describes the use of a plasticized poly 2-hydroxyethyl methacrylate resin prepared from high purity monomer as a non-tacky synthetic film for skin burns, with shortened forming time by adding water to the mixture.

U.S. Pat. No. 4,593,053 describes the use of a plasticized polyvinyl pyrrolidone as a hydrophilic medical type pressure sensitive adhesive for biomedical electrodes and transdermal devices.

WO 92/11825 describes the use of plasticized poly 2-hydroxyethyl methacrylate resin as a hydrophilic medical type pressure sensitive adhesive for a medical device.

U.S. Pat. No. 5,225,473 describes the use of a UV cured plasticized polyvinyl pyrrolidone as a hydrophilic medical type pressure sensitive adhesive for biomedical electrodes and transdermal devices.

U.S. Pat. No. 4,892,787 describes coated paper for inkjet printing containing pigment, an acrylic emulsion, and a water soluble polymer.

U.S. Pat. No. 5,206,071 describes acrylic graft copolymers and water soluble polymers.

U.S. Pat. No. 5,478,631 describes an inkjet recording sheet using a pigment and an amphoteric ion latex.

EP 0716929A1 describes acrylic graft copolymers and water soluble polymers.

DE 19516111A1 describes water soluble copolymers with crosslinkers.

U.S. Pat. No. 5,672,392 describes the preparation of recording materials for inkjet printers using acrylic emulsions and water soluble polymers.

U.S Pat. No. 3,813,695 discloses a rubber or latex surgical glove that is laminated with an internal lining of a hydrophilic material.

U.S. Pat. No. 4,575,476 discloses a dipped rubber glove having an outer rubber layer and a lubricating layer formed of a hydrogel polymer bonded thereto to provide a skin-contacting surface of the glove.

In general, the present invention is directed to providing a cost-effective method for the preparation of hydrophilic 2-hydroxyethyl methacrylate homopolymers and copolymers with utility as films, coatings, pressure sensitive adhesives, and compositions suitable for topical application to the skin.

The present invention is further directed to providing clear inkjet coatings without pigments that are water resistant and have good ink absorption with quick drying.

The invention is also related to providing a cost-effective method for the preparation of gel-free, hydrophilic polymers, which have utility in topical skin applications, as cosmetic compositions, dermatological compositions, and as skin friendly coatings, as pressure sensitive adhesives, and as precursors for hydrogels.

SUMMARY OF THE INVENTION

A method is provided for the preparation of gel-free poly 2-hydroxyethyl methacrylate substantially in the absence of a chain transfer agent, comprising introducing monomeric 2-hydroxyethyl methacrylate containing ethylene glycol dimethacrylate impurities in the range of no more than about 0.05–0.1% by weight of the monomer, into alcohol, polymerizing the 2-hydroxyethyl methacrylate to form a polymerization mixture, and optionally removing the alcohol. The alcohol is preferably selected from one of methanol and ethanol. Hydrophilic pressure sensitive adhesives are provided by adding polyethylene glycol to the polymerization mixture prior to removing the alcohol. Flexible hydrophilic coatings also are provided by adding glycerin to the polymerization mixture prior to removing the alcohol by drying.

In another embodiment, the monomeric 2-hydroxyethyl methacrylate contains alkylene glycol methacrylate impurities in the range of no more than about 3% by weight, wherein the alkylene glycol methacrylate impurities are selected from the group consisting of ethylene glycol dimethacrylate, diethylene glycol monomethacrylate, methacrylic acid and mixtures thereof.

A method is also provided for the preparation of a gel free, hydrophilic, water soluble polymer substantially in the absence of a chain transfer agent comprising a copolymer of 2-hydroxyethyl methacrylate and acrylic acid or methacrylic acid, including introducing monomeric 2-hydroxyethyl methacrylate into water solution with one of acrylic acid and methacrylic acid, adjusting the pH of the solution to a pH in the range of greater than about pH 3 to less than about pH 9, and copolymerizing the monomeric 2-hydroxyethyl methacrylate and acrylic or methacrylic acid.

In one embodiment, the monomeric 2-hydroxyethyl methacrylate contains at least 0.05% by weight, based on the monomer, of ethylene glycol dimethacrylate.

In another embodiment, hydrogels are prepared with copolymer concentrations greater than about 35% by weight.

In another embodiment, the copolymer of 2-hydroxyethyl methacrylate and acrylic acid or methacrylic acid is blended with a polyalkylene glycol, such as polyethylene glycol, to form a pressure sensitive adhesive.

In another embodiment, the copolymer of 2-hydroxyethyl methacrylate and acrylic acid or methacrylic acid is blended with glycerin to form a flexible coating.

A method is also provided for the preparation of a gel free hydrophilic polymer substantially in the absence of a chain transfer agent comprising a copolymer of 2-hydroxyethyl methacrylate and 4-hydroxybutyl acrylate, including introducing monomeric 2-hydroxyethyl methacrylate containing no more than about 0.05–0.1% by weight of ethylene glycol dimethacrylate into an alcohol solution with 4-hydroxybutyl acrylate, polymerizing the 2-hydroxyethyl methacrylate and 4-hydroxybutyl acrylate to form a polymerization mixture, and removing the alcohol. The alcohol is selected from one of methanol and ethanol, with ethanol being preferred.

In another embodiment, the monomeric 2-hydroxyethyl methacrylate contains no more than about 3% by weight alkylene glycol methacrylate impurities, wherein the alkylene glycol methacrylate impurities are selected from the group consisting of ethylene glycol dimethacrylate, diethylene glycol monomethacrylate, methacrylic acid and mixtures thereof.

A method of preparing an acrylic emulsion ink jet receptive clear coating is also provided comprising: forming an alkyl acrylate monomer-containing pre-emulsion feed mixture, introducing an activator into the alkyl acrylate monomer-containing pre-emulsion feed mixture, reacting a water soluble monomer feed in said alkyl acrylate monomer-containing pre-emulsion feed mixture, said water soluble monomer feed comprising 2-hydroxyethyl methacrylate and n-vinylpyrrolidone, to form a clear polymer in said alkyl acrylate monomer-containing pre-emulsion feed mixture.

In another embodiment, the method further comprises subsequently reacting with said clear polymer in said alkyl acrylate monomer-containing pre-emulsion feed mixture, a water insoluble monomer feed mixture comprising 2-hydroxyethyl methacrylate, n-vinyl pyrrolidone, butyl acrylate, and methacrylic acid to form a clear polymer over said polymer in said alkyl acrylate monomer-containing pre-emulsion feed mixture.

A method for the preparation of a powdered low gel poly 2-hydroxyethyl methacrylate substantially in the absence of a chain transfer agent is also provided comprising: introducing monomeric 2-hydroxyethyl methacrylate containing ethylene glycol dimethacrylate impurities in the range of no more than about 0.05 to about 0.1% by weight, based on the monomer, into water, polymerizing the 2-hydroxyethyl methacrylate, drying said polymerized the 2-hydroxyethyl methacrylate, and grinding said dried polymerized 2-hydroxyethyl methacrylate to form a powder.

In another embodiment, the monomeric 2-hydroxyethyl methacrylate contains no more than about 3% by weight alkylene glycol methacrylate impurities, wherein the alkylene glycol methacrylate impurities are selected from the group consisting of ethylene glycol dimethacrylate, diethylene glycol monomethacrylate, methacrylic acid and mixtures thereof.

In another embodiment, said poly 2-hydroxyethyl methacrylate powder is blended with a polyalkylene glycol, such as polyethylene glycol to form a pressure sensitive adhesive.

A method is also provided for the preparation of a gel free hydrophilic polymer substantially in the absence of a chain transfer agent comprising a copolymer of 2-hydroxyethyl methacrylate and 4-hydroxybutyl acrylate, including introducing monomeric 2-hydroxyethyl methacrylate containing no more than about 0.05–0.1% by weight of ethylene glycol dimethacrylate into an alcohol solution with 4-hydroxybutyl acrylate, polymerizing the 2-hydroxyethyl methacrylate and 4-hydroxybutyl acrylate to form a polymerization mixture, and removing the alcohol. The alcohol is selected from one of methanol and ethanol, with ethanol being preferred.

In another embodiment, the monomeric 2-hydroxyethyl methacrylate contains no more than about 3% by weight alkylene glycol methacrylate impurities, wherein the alkylene glycol methacrylate impurities are selected from the group consisting of ethylene glycol dimethacrylate, diethylene glycol monomethacrylate, methacrylic acid and mixtures thereof.

A method is also provided for the preparation of a gel free hydrophilic copolymer of 2-hydroxyethyl methacrylate and 4-hydroxybutyl acrylate substantially in the absence of a chain transfer agent comprising introducing monomeric 2-hydroxyethyl methacrylate containing no more than about 0.05–0.1% by weight of ethylene glycol dimethacrylate into a solution of water and alcohol with 4-hydroxybutyl acrylate, and polymerizing the 2-hydroxyethyl methacrylate and 4-hydroxybutyl acrylate to form a polymerization mixture.

In a preferred embodiment, the alcohol is selected from one of methanol and ethanol, with ethanol being preferred.

In another embodiment, the monomeric 2-hydroxyethyl methacrylate contains no more than about 3% by weight alkylene glycol methacrylate impurities, wherein the alkylene glycol methacrylate impurities are selected from the group consisting of ethylene glycol dimethacrylate, diethylene glycol monomethacrylate, methacrylic acid and mixtures thereof.

In another embodiment, the copolymer of 2-hydroxyethyl methacrylate and 4-hydroxybutyl acrylate is blended with a polyalkylene glycol, such as polyethylene glycol, to form a pressure sensitive adhesive.

The invention also provides a method for the preparation of a gel-free homopolymer of 4-hydroxybutyl acrylate substantially in the absence of a chain transfer agent comprising introducing monomeric 4-hydroxybutyl acrylate into alcohol, and polymerizing the 4-hydroxybutyl acrylate to form a polymerization mixture.

In another embodiment, the present invention provides a method for the preparation of a gel free hydrophilic homopolymer of 4-hydroxybutyl acrylate substantially in the absence of a chain transfer agent comprising introducing monomeric 4-hydroxybutyl acrylate into a solution of water and alcohol, and polymerizing the 4-hydroxybutyl acrylate.

In a preferred embodiment, the alcohol is selected from one of methanol and ethanol, with ethanol being preferred.

In another embodiment, the present invention provides a method for the preparation of a gel free hydrophilic homopolymer of 2-hydroxyethyl methacrylate substantially in the absence of a chain transfer agent comprising introducing monomeric 2-hydroxyethyl methacrylate containing no more than about 0.05–0.1% by weight of ethylene glycol dimethacrylate into a solution of water and alcohol, and polymerizing the 2-hydroxyethyl methacrylate.

In a preferred embodiment, the alcohol is selected from one of methanol and ethanol, with ethanol being preferred. These homopolymers of 2-hydroxyethyl methacrylate prepared are stable in solution.

In another embodiment, the monomeric 2-hydroxyethyl methacrylate contains no more than about 3% by weight alkylene glycol methacrylate impurities, wherein the alkylene glycol methacrylate impurities are selected from the group consisting of ethylene glycol dimethacrylate, diethylene glycol monomethacrylate, methacrylic acid and mixtures thereof.

The present invention provides a method for the preparation of a water insoluble, gel-free copolymer of 2-hydroxyethyl methacrylate and acrylic acid or methacrylic acid substantially in the absence of a chain transfer agent comprising: introducing monomeric 2-hydroxyethyl methacrylate containing ethylene glycol dimethacrylate impurities up to about 0.15% by weight, based on the weight of the monomer, and at least one of acrylic acid or methacrylic acid into a solution of water and alcohol; and copolymerizing the 2-hydroxyethyl methacrylate and the at least one of acrylic acid or methacrylic acid to form a polymerization mixture.

In one embodiment, the monomeric 2-hydroxyethyl methacrylate useful in the inventive method may contain ethylene glycol dimethacrylate impurity in the range of about 0.05% to about 0.1% by weight of the monomer. In another embodiment, the inventive method uses a monomeric 2-hydroxyethyl methacrylate that contains impurities in a total amount of no more than about 3% by weight of the monomer, where the impurities include ethylene glycol dimethacrylate, diethylene glycol monomethacrylate, methacrylic acid and mixtures of these impurities.

Hydrophilic pressure sensitive adhesives are provided by adding polyalkylene glycol to the polymerization mixture. Flexible skin coatings are provided by adding a flexiblizing agent to the polymerization mixture.

The present invention also provides a method for the preparation of a hydrophilic, gel-free, water insoluble copolymer of 2-hydroxyethyl methacrylate, 4-hydroxybutyl acrylate and at least one of acrylic acid or methacrylic acid substantially in the absence of a chain transfer agent comprising: introducing monomeric 2-hydroxyethyl methacrylate, monomeric 4-hydroxybutyl acrylate and at least one of acrylic acid or methacrylic acid into a solution of water and alcohol, wherein the monomeric 2-hydroxyethyl methacrylate contains ethylene glycol dimethacrylate impurities up to about 0.15% by weight, based on the weight of the monomer; and copolymerizing the monomeric 2-hydroxyethyl methacrylate, monomeric 4-hydroxybutyl acrylate and at least one of acrylic acid or methacrylic acid to form a polymerization mixture.

In another embodiment, the monomeric 2-hydroxyethyl methacrylate useful in the inventive method contain ethylene glycol dimethacrylate impurity in the range of about 0.05% to about 0.1% by weight of the monomer. In another embodiment, the inventive method uses a monomeric 2-hydroxyethyl methacrylate that contains impurities in a total amount of no more than about 3% by weight of the monomer, where the impurities include ethylene glycol dimethacrylate, diethylene glycol monomethacrylate, methacrylic acid and mixtures of these impurities.

Hydrophilic pressure sensitive adhesives are provided by adding polyalkylene glycol to the polymerization mixture. Flexible skin coatings are provided by adding a flexiblizing agent to the polymerization mixture.

The present invention also provides a method for the preparation of a substantially monoalcohol-free, gel-free, water insoluble, hydrophilic copolymer of 2-hydroxyethyl methacrylate and 4-hydroxybutyl acrylate substantially in the absence of a chain transfer agent comprising: introducing monomeric 2-hydroxyethyl methacrylate containing ethylene glycol dimethacrylate impurities up to about 0.15% by weight, based on the weight of the monomer, and monomeric 4-hydroxybutyl acrylate into a solution of water and a monoalcohol; copolymerizing the monomeric 2-hydroxyethyl methacrylate and the 4-hydroxybutyl acrylate to form a polymerization mixture; leaching the copolymer of 2-hydroxyethyl methacrylate and 4-hydroxybutyl acrylate to substantially remove residual monomer; and substantially replacing the monoalcohol with a polyhydric alcohol.

In another embodiment, the monomeric 2-hydroxyethyl methacrylate that is useful in the inventive method may contain ethylene glycol dimethacrylate impurity in the range of about 0.05% to about 0.1% by weight of the monomer. In another embodiment, the inventive method uses a monomeric 2-hydroxyethyl methacrylate that contains impurities in a total amount of no more than about 3% by weight of the monomer, where the impurities include ethylene glycol dimethacrylate, diethylene glycol monomethacrylate, methacrylic acid and mixtures of these impurities.

Flexible skin coatings are provided by removing the water after the leaching and replacing steps.

The invention further provides a method for the preparation of a substantially monoalcohol-free, gel-free, water insoluble, hydrophilic copolymer of 2-hydroxyethyl methacrylate and 4-hydroxybutyl acrylate substantially in the absence of a chain transfer agent comprising: introducing monomeric 2-hydroxyethyl methacrylate containing ethylene glycol dimethacrylate impurities up to about 0.15% by weight, based on the weight of the monomer, and monomeric 4-hydroxybutyl acrylate into a solution of water and polyhydric alcohol; and copolymerizing the monomeric 2-hydroxyethyl methacrylate and the 4-hydroxybutyl acrylate to form a polymerization mixture.

In another embodiment, the monomeric 2-hydroxyethyl methacrylate that is useful in the inventive method may contain ethylene glycol dimethacrylate impurity in the range of about 0.05% to about 0.1% by weight of the monomer. In another embodiment, the inventive method uses a monomeric 2-hydroxyethyl methacrylate that contains impurities in a total amount of no more than about 3% by weight of the monomer, where the impurities include ethylene glycol dimethacrylate, diethylene glycol monomethacrylate, methacrylic acid and mixtures of these impurities.

Flexible skin coatings are provided by substantially removing the water from the polymerization mixture.

The invention further provides a method for the preparation of a substantially monoalcohol-free, gel-free, water insoluble, hydrophilic homopolymer of 2-hydroxyethyl methacrylate substantially in the absence of a chain transfer agent comprising: introducing monomeric 2-hydroxyethyl methacrylate containing ethylene glycol dimethacrylate impurities up to about 0.15% by weight, based on the weight of the monomer, into a solution of water and a monoalcohol; polymerizing the 2-hydroxyethyl methacrylate to form a polymerization mixture; leaching the homopolymer of 2-hydroxyethyl methacrylate to substantially remove residual monomer; and substantially replacing the monoalcohol with a polyhydric alcohol.

In another embodiment, the monomeric 2-hydroxyethyl methacrylate that is useful in the inventive method may contain ethylene glycol dimethacrylate impurity in the range of about 0.05% to about 0.1% by weight of the monomer. In another embodiment, the inventive method uses a monomeric 2-hydroxyethyl methacrylate that contains impurities in a total amount of no more than about 3% by weight of the monomer, where the impurities include ethylene glycol dimethacrylate, diethylene glycol monomethacrylate, methacrylic acid and mixtures of these impurities.

Flexible skin coatings are provided by substantially removing the water from the polymer after the leaching and replacing steps.

The present invention further provides a method for the preparation of substantially gel-free, water insoluble, hydrophilic homopolymer of 2-hydroxyethyl methacrylate substantially in the absence of a chain transfer agent comprising: introducing monomeric 2-hydroxyethyl methacrylate containing ethylene glycol dimethacrylate impurities up to about 0.15% by weight, based on the weight of the monomer, into a solution of water and polyhydric alcohol; and polymerizing the 2-hydroxyethyl methacrylate to form a polymerization mixture.

As such, this invention includes methods of preparing gel-free, hydrophilic, water insoluble homopolymers and copolymers, and gel-free, hydrophilic water soluble copolymers that are suitable in the formulation of topical compositions for application to human skin and hair, such as cosmetic compositions and dermatological compositions, and to their use as pressure sensitive adhesives and flexible coatings.

The term "low gel" as used in the specification refers to a poly 2-hydroxyethyl methacrylate (polyHEMA) polymer having less than 15% gel content, as determined by the method described hereinbelow.

The term "gel free" as used in the specification refers to a polyHEMA polymer having less than 5% gel content, as determined by visual inspection or by the "gel content" method described hereinbelow. The term "gel free" as used in the specification is intended to be synonymous with the phrases "soluble in alcohol" or "insoluble in water." The presence or absence of gel in the polymer products of the present invention can be determined by visually inspecting the polymerization mixture for the presence of particulates. Optionally, a thin film of the polymer product can be poured and visually inspected for particulates. A polymer product containing no particulate matter upon visual inspection is considered to be "gel-free."

The "gel content" of the poly HEMA polymers is a measure of the polymer that is insoluble in methanol (MeOH). The gel content is determined as follows: The poly HEMA adhesive polymer is coated onto a silicone release liner and dried at 70° C. for 15 minutes. The adhesive is removed from the release liner, and a 60 to 80 mg sample of the adhesive is accurately weighed out and placed into a 10 μm PTFE membrane filter. The edges of the filter are thermally sealed to contain the sample, and the filter is placed in a vial containing about 15 g of methanol. The vial is agitated for 72 hours, and the filter is taken out of the solvent and dried at 120° C. for 120 minutes.

The filter is then weighed, and the resulting weight of the sample is used to calculate the percent gel as follows:

$$\% \text{ gel} = (b/a) \times 100$$

wherein,
a=initial weight of the sample, and
b=final weight of the sample.

BRIEF DESCRIPTION OF THE DRAWINGS

FIG. 2 depicts a blend of separately polymerized copolymer particles.

DETAILED DESCRIPTION OF THE INVENTION

Figure 1:
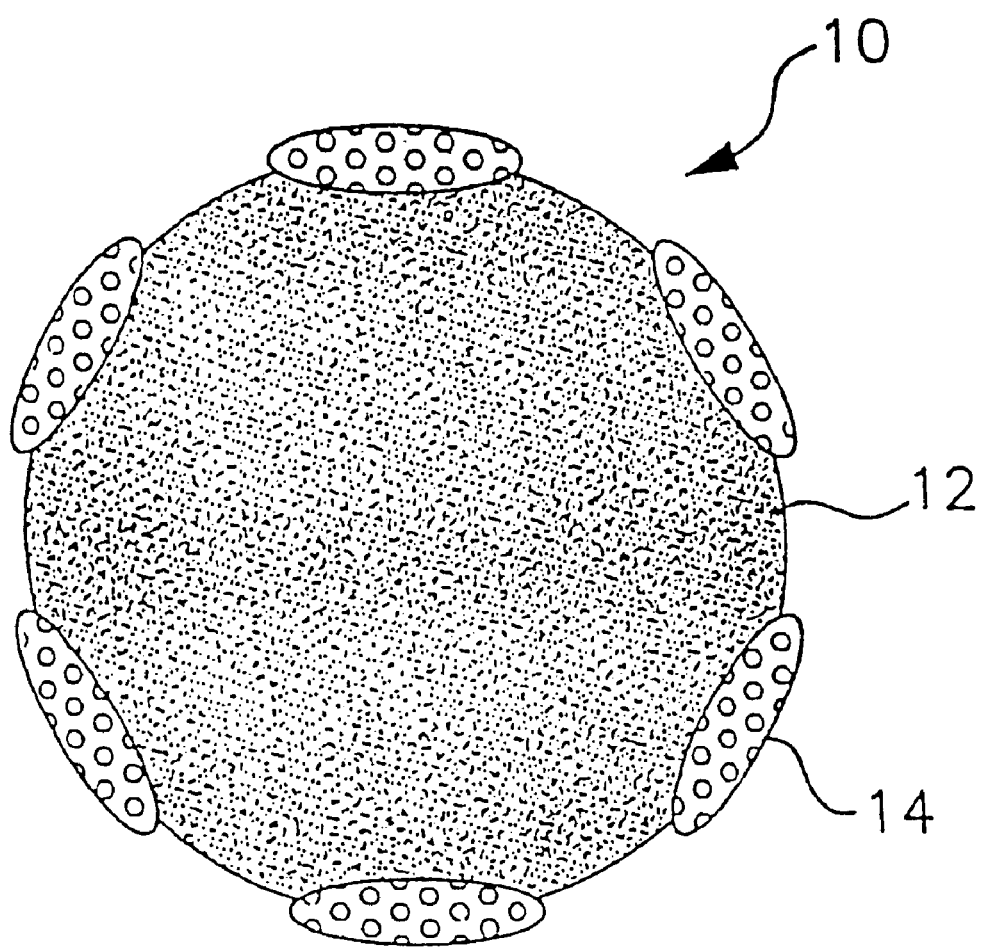
FIG. 1 depicts a sequentially polymerized copolymer particle.

In one embodiment, the present invention provides a method for the preparation of a gel-free poly 2-hydroxyethyl methacrylate substantially in the absence of a chain transfer agent. The method includes introducing monomeric 2-hydroxyethyl methacrylate containing ethylene glycol dimethacrylate impurities in the range of no more than about 0.05 to 0.1% by weight into an alcohol selected from one of methanol and ethanol, polymerizing the 2-hydroxyethyl methacrylate to form a polymerization mixture, and removing the alcohol. Polymerization is induced by free radical initiation, and the alcohol is preferably removed by coating a substrate and drying the mixture. In one embodiment, the monomeric 2-hydroxyethyl methacrylate contains alkylene glycol impurities in a total amount of no more than 3% by weight, and the impurities are selected from the group consisting of ethylene glycol dimethacrylate, diethylene glycol monomethacrylate, methacrylic acid and mixtures thereof. The controlled level of impurities results in the gel free polymer, even without using ultra-pure monomer.

As described above, free radical polymerization is initiated by a suitable initiator. The initiator must be soluble in the alcohol and the 2-hydroxyethyl methacrylate monomer mixture. Suitable initiators that are soluble in alcohol include, but are not limited to, peroxides such as benzoyl peroxide, and azo compounds, such as 2,2'-azobis(isobutyronitrile).

The method of the present invention, therefore, provides for the cost effective preparation of a gel-free poly 2-hydroxyethyl methacrylate, substantially in the absence of a chain transfer agent, using industrial grade 2-hydroxyethyl methacrylate monomer. A 2-Hydroxyethyl methacrylate monomer suitable for use in the method of the present invention is available from Mitsubishi Rayon, Japan.

In another embodiment, the present invention provides a method for the preparation of a gel-free poly 2-hydroxyethyl methacrylate substantially in the absence of a chain transfer agent, to achieve a hydrophilic pressure sensitive adhesive. The method includes introducing monomeric 2-hydroxyethyl methacrylate containing ethylene glycol dimethacrylate impurities in the range of about 0.05 to 0.1% by weight into an alcohol selected from one of methanol or ethanol, polymerizing the 2-hydroxyethyl methacrylate to form a polymerization mixture, adding a polyalkylene glycol, such as polyethylene glycol in a range of about 40% to about 70% by weight, based on the weight of the polymer and the polyethylene glycol, and removing the alcohol to form a hydrophilic pressure sensitive adhesive. Polymerization is induced by free radical initiation, and alcohol removal is preferably accomplished by coating the mixture onto a substrate and drying the mixture. Although the preferred polyalkylene glycol used to prepare the pressure sensitive is polyethylene glycol, other polyalkylene glycols, such as polypropylene glycol may be used. In addition, copolymers of ethylene and propylene glycol may also be used to form the pressure sensitive adhesive.

In another embodiment, the 2-hydroxyethyl methacrylate contains alkylene glycol impurities in a total amount of no more than about 3% by weight of monomer, and the impurities are selected from the group consisting of ethylene glycol dimethacrylate, diethylene glycol monomethacrylate, methacrylic acid and mixtures thereof. The hydrophilic pressure sensitive adhesives formed by this method have utility in many label and tape applications, and is particularly suitable for medical applications.

In yet another embodiment, the present invention provides a method for the preparation of a flexible hydrophilic coating comprising a gel-free poly 2-hydroxyethyl methacrylate produced substantially in the absence of a chain transfer agent. The method comprises introducing monomeric 2-hydroxyethyl methacrylate containing ethylene glycol dimethacrylate impurities in the range of about 0.05 to 0.1% by weight into an alcohol selected from one of methanol and ethanol, polymerizing the 2-hydroxyethyl methacrylate to form a polymerization mixture, adding glycerin to the polymerization mixture in an amount from about 10% to about 50% by weight of the polymer, preferably about 25% by weight of the polymer, and removing the alcohol to form a flexible hydrophilic coating. Polymerization is induced by free radical initiation, and alcohol removal by coating the mixture and drying.

In another embodiment, the 2-hydroxyethyl methacrylate contains alkylene glycol methacrylate impurities in the range of about 3%, based on the weight of the monomer. Preferably, the alkylene glycol impurities are selected from the group consisting of ethylene glycol dimethacrylate, diethylene glycol monomethacrylate, methacrylic acid and mixtures thereof, in a total amount of no more than about 3% by weight of monomer. The flexible hydrophilic coating formed by this method has utility in skin-friendly applications in which a high Moisture Vapor Transmission Rate (MVTR) is needed together with protective, skin barrier properties. The coating is also suitable for printable coatings, such as inkjet coatings for paper, plastic film, and the like.

While the above methods involve the formulation of a homopolymer of the 2-hydroxyethyl methacrylate monomer, the present invention also provides a method for the preparation of a gel free, hydrophilic, water soluble polymer comprising a copolymer of 2-hydroxyethyl methacrylate and acrylic acid or methacrylic acid. This method includes introducing monomeric 2-hydroxyethyl methacrylate into water solution with one of acrylic acid and methacrylic acid in weight ratio in the range of about 3 to about 15%, adjusting the pH of the solution to a pH in the range of greater than about pH 3 to less than about pH 9, and copolymerizing the monomeric 2-hydroxyethyl methacrylate and acrylic or methacrylic acid. Copolymerization is induced by free radical initiation. A pH of 3 or less and a pH of 9 or greater should be avoided, because the reactants may precipitate out or not form a useable copolymer.

In one preferred embodiment, the method of forming a copolymer of 2-hydroxyethyl methacrylate and one of acrylic acid and methacrylic acid includes introducing monomeric 2-hydroxyethyl methacrylate into water solution with one of acrylic acid and methacrylic acid in weight ratio in the range of about 3 to about 15%, adjusting the pH of the solution to at least pH 5, and copolymerizing the monomeric 2-hydroxyethyl methacrylate and acrylic or methacrylic acid.

In one embodiment, the 2-hydroxyethyl methacrylate monomer contains at least 0.05% by weight of ethylene glycol dimethacrylate.

An initiator is added to the mixture of the monomeric 2-hydroxyethyl methacrylate and acrylic or methacrylic acid in an amount effective to initiate copolymerization. Suitable initiators include dissociative initiators and redox initiators. Suitable dissociative initiators that may be used in the present invention include, but are not limited to, persulfates such as ammonium persulfate, potassium persulfate and sodium persulfate, hydrogen peroxide, tert-butyl hydroperoxide, and azo compounds such as 4,4'-azobis(4-cyanovaleric acid). Redox initiators include, but are not limited to, persulfates with bisulfate, such as sodium persulfate with sodium metabisulfite, hydrogen peroxide with ferrous ion, sulfite ion, bisulfite ion or ascorbic acid, and hydroperoxides with sulfoxylates, such as tert-butyl hydroperoxide with sodium formaldehyde sulfoxylate.

In a preferred embodiment, methacrylic acid is used. In another preferred embodiment, the hydrophilic copolymer comprises from about 90% to about 95% by weight 2-hydroxyethyl methacrylate.

In the preparation of the hydrophilic copolymer of 2-hydroxyethyl methacrylate and methacrylic acid or acrylic acid of the present invention, it is preferable to raise the pH of the monomer mixture to at least a pH of about 5 in order to neutralize the monomer mixture before polymerization to prevent the precipitation of the polymer as it is formed. The pH adjustment may be accomplished by adding aqueous ammonium hydroxide or other basic chemical(s) known to those skilled in the art. The hydrophilic copolymer that is formed is soluble in methanol and soluble in water at concentrations up to about 35% by weight. At concentrations greater than about 35% by weight in water, the hydrophilic copolymer becomes a hydrogel.

By definition, a hydrogel is swellable with water and insoluble in water, forms an equilibrium state with water, and maintains its equilibrium shape. The hydrophilic copolymers of 2-hydroxyethyl methacrylate and methacrylic acid or acrylic acid of this invention meet all of the criteria for a hydrogel at polymer concentrations greater than about 35% by weight without the necessity of crosslinking. Hydrogels at lower concentrations of polymer can meet this criteria with crosslinking with formaldehydes, metal salts, aziridines, isocyanates, dichromates, and the like, in the amount of up to about 10% by weight of polymer. If the copolymers are crosslinked, then the amount of crosslinker is preferably less than about 10% by weight of the polymer if crosslinkers other than isocyanates are used, and up to about 20% by weight of the polymer if isocyanates are used.

In another embodiment, the present invention provides a method for the preparation of substantially gel-free, hydrophilic, water soluble copolymers of 2-hydroxyethyl methacrylate and methacrylic acid or acrylic acid substantially in the absence of a chain transfer agent, to achieve a hydrophilic pressure sensitive adhesive. The method includes introducing monomeric 2-hydroxyethyl methacrylate into water solution with one of acrylic acid and methacrylic acid, adjusting the pH of the monomer mixture to a pH in the range of greater than about pH 3 to about less than pH 9, copolymerizing the 2-hydroxyethyl methacrylate and acrylic or methacrylic acid to form a polymerization mixture, adding a polyalkylene glycol, such as polyethylene glycol in a range of about 40% to about 70% by weight, based on the weight of the polymer and the polyethylene glycol, to the polymerization mixture, and removing the water to form a hydrophilic pressure sensitive adhesive. Polymerization is induced by free radical initiation, and water removal is preferably accomplished by coating the mixture onto a substrate and drying the mixture. Although the preferred polyalkylene glycol used to prepare the pressure sensitive is polyethylene glycol, other polyalkylene glycols, such as polypropylene glycol may be used. In addition, copolymers of ethylene and propylene glycol may also be used to form the pressure sensitive adhesive.

In one preferred embodiment, the method of forming a copolymer of 2-hydroxyethyl methacrylate and one of acrylic acid and methacrylic acid includes introducing monomeric 2-hydroxyethyl methacrylate into water solution with one of acrylic acid and methacrylic acid in weight ratio in the range of about 3 to about 15%, adjusting the pH of the solution to at least pH 5, and copolymerizing the monomeric 2-hydroxyethyl methacrylate and acrylic or methacrylic acid.

In yet another embodiment, the present invention provides a method for the preparation of a flexible hydrophilic coating comprising a substantially gel-free hydrophilic copolymer of 2-hydroxyethyl methacrylate and methacrylic acid and acrylic acid produced substantially in the absence of a chain transfer agent. The method comprises introducing monomeric 2-hydroxyethyl methacrylate into water solution with one of acrylic acid and methacrylic acid, adjusting the pH of the monomer mixture to a pH in the range of greater than about pH 3 to about less than pH 9, copolymerizing the 2-hydroxyethyl methacrylate and acrylic or methacrylic acid to form a polymerization mixture, adding glycerin to the polymerization mixture in an amount from about 10% to about 50% by weight of the polymer, preferably about 25% by weight of the polymer, and removing the water to form a flexible hydrophilic coating, which is particularly suited for medical and skin care. Polymerization is induced by free radical initiation, and water removal by coating the mixture and drying.

In one preferred embodiment, the method of forming a copolymer of 2-hydroxyethyl methacrylate and one of acrylic acid and methacrylic acid includes introducing monomeric 2-hydroxyethyl methacrylate into water solution with one of acrylic acid and methacrylic acid in weight ratio in the range of about 3 to about 15%, adjusting the pH of the solution to at least pH 5, and copolymerizing the monomeric 2-hydroxyethyl methacrylate and acrylic or methacrylic acid.

In addition to the uses as hydrogels, pressure sensitive adhesives, and flexible films or coatings, the poly 2-hydroxyethyl methacrylate/acrylic acid or methacrylic acid copolymer prepared in water can also be used as an abrasion resistant coating for glass bottles. Crosslinkers and surfactants may be added to the poly 2-hydroxyethyl methacrylate/acrylic acid or methacrylic acid copolymer coatings to achieve optimum coating performance.

The crosslinker may be added to the copolymer in an amount from about 1 to about 10 percent by weight based on the weight of the copolymer. Suitable crosslinkers include, but are not limited to, formaldehydes, metal salts, aziridines, isocyanates, dichromates and the like. A preferred crosslinker that may be added to the copolymer is ammonium dichromate, and is added to the copolymer at about 7.5% by weight, based on the weight of the copolymer.

The surfactant may be added to the copolymer in an amount from about 0 to about 5 percent by weight based on the weight of the copolymer. Suitable surfactants include, but are not limited to, water dispersible silicone and fluorocarbon surfactants. A preferred surfactant that may be added to the copolymer is a silicone surfactant that is commercially available from Dow Corning, and is added to the copolymer at about 2% by weight, based on the weight of the copolymer.

The copolymer coating can be easily removed from the glass bottles by alkali treatment, such as an alkaline solution of 1% sodium hydroxide.

In another embodiment, the present invention provides a method for the preparation of a gel free hydrophilic polymer substantially in the absence of a chain transfer agent comprising a copolymer of 2-hydroxyethyl methacrylate and 4-hydroxybutyl acrylate, including introducing monomeric 2-hydroxyethyl methacrylate containing 0.05 to 0.1% by weight of ethylene glycol dimethacrylate impurities, into an alcohol solution with 4-hydroxybutyl acrylate, polymerizing the 2-hydroxyethyl methacrylate and 4-hydroxybutyl acrylate to form a polymerization mixture, and removing the alcohol. The alcohol is selected from one of methanol and ethanol, with ethanol being preferred.

In another embodiment, the monomeric 2-hydroxyethyl methacrylate contains no more than about 3% by weight of alkylene glycol methacrylate impurities.

The copolymer of 2-hydroxyethyl methacrylate and 4-hydroxybutyl acrylate is a hydrophilic copolymer that is insoluble in water and does not require crosslinking for water resistance. In addition, the copolymer of 2-hydroxyethyl methacrylate and 4-hydroxybutyl acrylate is flexible enough to form a flexible coating or film for medical and skin care or skin protection applications without the need for the addition of glycerin. The coating is also suitable for printable coatings, such as inkjet coatings for paper, plastic film, and the like. The flexible coating comprising the copolymer of 2-hydroxyethyl methacrylate and 4-hydroxybutyl acrylate is also useful as a Rubber or latex glove coating, with particular usefulness in wet-donning applications. Rubber or latex gloves require the ability of donning, that is, the ability to slide on and off the surface of the skin with minimal friction. The copolymer of 2-hydroxyethyl methacrylate and 4-hydroxybutyl acrylate provides a flexible, non-tacky glove coating that allows the donning, wet or dry, of the Rubber or latex glove with minimal blocking and without undue friction or clinging.

In addition to its applicability to hydrophilic coatings and pressure sensitive adhesives, the present invention provides a method for the preparation of an acrylic emulsion ink jet receptive clear coating. In this embodiment, the method includes forming an alkyl acrylate monomer-containing pre-emulsion feed mixture, introducing an activator into the alkyl acrylate monomer-containing pre-emulsion feed mixture, reacting a water soluble monomer feed in the alkyl acrylate monomer-containing pre-emulsion feed mixture, wherein the weight ratio of the alkyl acrylate monomer-containing pre-emulsion feed mixture to the water soluble monomer feed is from about 1:1 to about 1:2, to form a clear, transparent polymer in the alkyl acrylate monomer-containing emulsion feed mixture. The alkyl acrylate monomers may include, but are not limited to, ethyl acrylate, 2-ethylhexyl acrylate, butyl acrylate, isooctyl acrylate, and the like. A preferred alkyl acrylate monomer is butyl acrylate. The water soluble monomer feed comprises 2-hydroxyethyl methacrylate and a cationic monomer, such as n-vinylpyrrolidone, wherein the weight ratio range of the 2-hydroxyethyl methacrylate to the cationic monomer is from about 1:0 to about 1:1. The term "clear" as used herein to describe the polymer refers to a polymer product that does not include particulate or inclusions that would indicate incompatibilities in the polymerization process. The term "transparent" as used herein to describe the polymer refers to a polymer product that is capable of being seen through. Both "clear" and "transparent" appearances are based upon unaided, visual inspection.

In one embodiment, the 2-hydroxyethyl methacrylate contains at least 0.05% by weight of ethylene glycol dimethacrylate.

The acrylic emulsion ink jet receptive clear coating of the present invention does not require the addition of fillers or particulate to obtain ink absorbency, and is particularly useful with ink jet printers that use dye based inks.

In a variation of this embodiment, the preformed clear polymer in the alkyl acrylate monomer-containing emulsion mixture is subsequently reacted with a water insoluble monomer feed mixture, for example comprising 2-hydroxyethyl methacrylate, n-vinyl pyrrolidone, butyl acrylate, and methacrylic acid, in a weight ratio of about 20% to about 80% to form a second clear polymer substantially over the preformed clear polymer in the alkyl acrylate monomer-containing emulsion mixture.

The addition of the water soluble monomer feed to the alkyl acrylate monomer-containing pre-emulsion feed mixture produces a first clear, or core polymer formed in the alkyl acrylate monomer-containing pre-emulsion mixture. A second clear polymer, may be formed in the presence of the first polymer from a second monomer charge which is, in one embodiment, the water insoluble monomer feed comprising 2-hydroxyethyl methacrylate, n-vinyl pyrrolidone, butyl acrylate and methacrylic acid. The second clear polymer is formed substantially over the first clear polymer.

This polymerization process is known as sequential polymerization. It is believed that the product is a domain-type emulsion polymer in which the first or core particles form one domain and the second or shell copolymer forms a second domain which partially or continuously surrounds the core. By reserving a significant amount of the monomers to the second charge one can effectively use the monomers of the second charge to control properties.

The two systems are depicted to FIG. Nos. 1 and 2. With reference to FIG. 1, a sequentially polymerized polymer particle is formed in a reaction emulsion mixture as particle 10 and comprised of a central domain 12 completely or partially surrounded by a second stage polymerized outer domain 14. In their formation, the monomers of the inner domain are polymerized first, followed by polymerization of the monomers forming the outer domain which associate with and are believed to attach to the initially formed inner domain copolymer particles.

As depicted in FIG. 2, if the individual polymers are separately polymerized and mixed, they form a random blend of core 16 and shell 18 polymer particles with little or no attachment or association with each other.

As discussed above, an initiator is added to the monomeric 2-hydroxyethyl methacrylate monomers and, optionally, n-vinyl pyrrolidone, in an amount effective to initiate copolymerization. Suitable initiators include dissociative initiators and redox initiators. Suitable dissociative initiators include, but are not limited to, persulfates such as ammonium persulfate, potassium persulfate and sodium persulfate, hydrogen peroxide, tert-butyl hydroperoxide, and azo compounds such as 4,4'-azobis(4-cyanovaleric acid). Redox initiators include, but are not limited to, persulfates with bisulfate ion, such as sodium persulfate with sodium metabisulfite, hydrogen peroxide with ferrous ion, sulfite ion, bisulfite ion or ascorbic acid, and hydroperoxides with sulfoxylates, such as tert-butyl hydroperoxide with sodium formaldehyde sulfoxylate.

A preferred activator is sodium formaldehyde sulfoxylate, preferably in an amount of about 0.1 to about 1 weight percent based on the weight of the polymer. The water insoluble monomer feed may further comprise an effective amount of an initiator, such as tert-butyl hydroperoxide or the like, and at least one water insoluble acrylate or methacrylate selected from methyl acrylate, methyl methacrylate, 2-ethylhexyl acrylate, butyl acrylate, trifluoroethyl methacrylate, and mixtures thereof in the amount of about 15 to about 35% by weight of the polymer, preferably from about 15% by weight of the polymer. Trifluoroethyl methacrylate is preferably included in the water insoluble monomer feed in an amount of about 1.5% by weight, based on the weight of the polymer. Inclusion of trifluoroethyl methacrylate results in the improvement of sheet feeding performance during inkjet printing.

The substrate which is used in the present invention may be any substrate material such as paper and polymeric films in the form of sheets and strips, and the like. Preferred types of paper include semi-gloss paper and high gloss paper. In one embodiment, the substrate is a polymeric film. In a preferred embodiment, the substrate is a polymeric film formed from a thermoplastic material. In a more preferred embodiment, the substrate is a polymeric film selected from the group consisting of polystyrene, a polyester, and a polyolefin such as polyethylene or polypropylene.

The acrylic emulsion ink jet receptive clear coatings of the present invention are particularly suited as coatings for clear films and high gloss photo quality paper. It is an advantage of the present invention that these acrylic emulsion ink jet receptive coatings are clear, water resistant, have good ink absorption with quick drying, and low surface friction to enhance sheet feeding in ink jet printers. It is also an advantage of the present invention that the above properties may be achieved without the use of pigments or mixtures of polymers that would be expected to reduce the clarity of the coatings.

The copolymer of 2-hydroxyethyl methacrylate and 4-hydroxybutyl acrylate is a hydrophilic copolymer that is insoluble in water and does not require crosslinking for water resistance. In addition, the copolymer of 2-hydroxyethyl methacrylate and 4-hydroxybutyl acrylate is flexible enough to form a flexible coating or film for medical and skin care or skin protection applications without the need for the addition of glycerin. The flexible coating comprising the copolymer of 2-hydroxyethyl methacrylate and 4-hydroxybutyl acrylate is also useful as a Rubber or latex glove coating, with particular usefulness in wet-donning applications. Rubber or latex gloves require the ability of donning, that is, the ability to slide a glove on and off the surface of the skin with minimal friction. The copolymer of 2-hydroxyethyl methacrylate and 4-hydroxybutyl acrylate provides a flexible, non-tacky glove coating that allows the donning, wet or dry, of the Rubber or latex glove with minimal blocking and without undue friction or clinging.

In another embodiment, the copolymer product of 2-hydroxyethyl methacrylate and 4-hydroxybutyl acrylate may further contain up to about 10 weight percent of an additional monomer, based on the weight of the copolymeric product. More preferably, the copolymeric product may contain from about 2 to about 4 weight percent of the additional monomer. The inclusion of up to about 10 weight percent of the monomer increases the cohesive strength of the copolymer, while still maintaining pressure sensitive adhesive properties, skin coating properties, and water resistance. Useful monomers include alkyl acrylates, alkyl methacrylates, hydroxyalkyl acrylates, hydroxyalkyl methacrylates, N-vinyl lactams, vinyl acetate and styrene monomers.

The present invention, therefore, provides a gel-free, hydrophilic copolymer of 2-hydroxyethyl methacrylate and 4-hydroxybutyl acrylate that does not to be plasticized with either water or glycerin. The copolymer of 2-hydroxyethyl methacrylate and 4-hydroxybutyl acrylate is a water-insoluble, water-absorbing, amphilic, elastic, abrasion resistant and has improved mechanical properties. Additionally, the copolymer has a high moisture vapor transmission rate that is skin friendly and, therefore, is "skin friendly."

In another embodiment, the present invention provides a copolymer of 2-hydroxyethyl methacrylate and 4-hydroxybutyl acrylate is prepared substantially in the absence of a chain transfer agent. The copolymer is prepared by introducing monomeric 2-hydroxyethyl methacrylate with 4-hydroxybutyl acrylate into a solution of water and alcohol. The monomeric 2-hydroxyethyl methacrylate should contain ethylene glycol dimethacrylate impurities in the range of about 0.05 to about 0.1% by weight. The monomers of 2-hydroxyethyl methacrylate and 4-hydroxybutyl acrylate are copolymerized to form a polymerization mixture and the alcohol/water solution is substantially removed.

The copolymerization reaction of the monomeric 2-hydroxyethyl methacrylate and 4-hydroxybutyl acrylate is carried using a water-soluble initiator system. The use of a water-soluble initiator system results in a more efficient conversion of monomers into copolymer product and, therefore, reducing the amount of residual monomer remaining after the copolymerization reaction. Reducing the amount of residual monomer remaining in the polymerization mixture avoids the need of an extensive leaching process to remove the residual monomers and the remaining water-soluble initiator, which results in a time and cost savings.

In a preferred embodiment, the monomeric 2-hydroxyethyl methacrylate contains alkylene glycol impurities in the range of no more than about 3% by weight, wherein the alkylene glycol impurities are selected from ethylene glycol dimethacrylate, diethylene glycol monomethacrylate, methacrylic acid and mixtures thereof.

In general, the copolymers of 2-hydroxyethyl methacrylate and 4-hydroxybutyl acrylate can be utilized as a topical skin coating or barrier. Some useful applications of the copolymer of 2-hydroxyethyl methacrylate and 4-hydroxybutyl acrylate includes use as sprayable carriers for topical application of drugs to the skin. For this application, the copolymer of 2-hydroxyethyl methacrylate and 4-hydroxybutyl acrylate may be mixed with an alcohol or glycol solution to produce a sprayable vehicle or carrier that can be sprayed directly onto the skin. The copolymer may also be a component of a cream, including water in oil emulsions and oil in water emulsions, lotions, which are suspensions in water or oil, ointments, which are solutions in petroleum or polyethylene glycol, or aerosols, which are sprayable solutions in water/alcohol and gels.

The copolymer of 2-hydroxyethyl methacrylate and 4-hydroxybutyl acrylate may also be a component of a transdermal drug delivery system. Specifically, the water-insoluble copolymer can be used as a carrier or vehicle to deliver an effective amount of a pharmacologically active agent (drug) transdermally. In this embodiment, the copolymer may be loaded with an effective amount of a pharmacologically active agent and locally placed on the surface of the skin. The transdermal drug delivery system can also include, as known in the art, skin permeation enhancers to facilitate the transderaml delivery of the pharmacologically active agent. The copolymer performs a dual function as a carrier of a pharmacologically active agent and a protective coating or skin barrier.

The copolymers of 2-hydroxyethyl methacrylate and 4-hydroxybutyl acrylate can be sprayed onto the skin before the application of adhesive-coated bandages, tapes, or other adhesive-coated medical devices to prevent irritation of sensitive skin.

The copolymers of 2-hydroxyethyl methacrylate and 4-hydroxybutyl acrylate can be used as an elastomeric medical film. Preferably, the copolymer of 2-hydroxyethyl methacrylate and 4-hydroxybutyl acrylate can be coated onto a substrate, such as a release liner and dried. The copolymer will be self cross-linking with heat treatment. Preferably, the copolymer will be self cross-linking by heat treating at a temperature in the range of about 70° C. to about 150° C., more preferably in a temperature range of about 70° C. to about 125° C. The elastomeric medical film can be used directly over a wound on the skin to provide a dressing or barrier. The elastomeric film is soft and pliable, and easily conforms to the contours of human skin.

The copolymers of 2-hydroxyethyl methacrylate and 4-hydroxybutyl acrylate can be used as a coating for gloves, such as rubber or latex medical gloves. The use of the copolymer of 2-hydroxyethyl methacrylate and 4-hydroxybutyl acrylate to coat a rubber or latex glove reduces the friction between the inner surface of the glove and the skin surface of the person donning the glove, especially under conditions of wet donning. The use of the copolymer of 2-hydroxyethyl methacrylate and 4-hydroxybutyl acrylate as a glove coating, therefore, alleviates the need for the use of powder or other lubricating materials with the gloves.

The copolymers of 2-hydroxyethyl methacrylate and 4-hydroxybutyl acrylate may also be included in sun block and sunscreen lotions, creams and sprays. as a carrier or vehicle of ultra-violet (UV) light absorbers, such as aminobenzoic acid, benzophenone-8 and benzophenone-4.

The copolymers of 2-hydroxyethyl methacrylate and 4-hydroxybutyl acrylate can be used as a carrier for water resistant cosmetic products. The cosmetic composition comprising the copolymer of 2-hydroxyethyl methacrylate and 4-hydroxybutyl acrylate is easy to apply to and remove from the surface of human skin, it is non-greasy, and non-occlusive. Like skin, the copolymers of 2-hydroxyethyl methacrylate and 4-hydroxybutyl acrylate are water insoluble, hydrophilic, amphilic, elastic and abrasion resistant.

The copolymer of 2-hydroxyethyl methacrylate and 4-hydroxybutyl acrylate can also be included as a component of a nasal spray or other mucus membrane drug delivery systems, as a carrier for a pharmacologically active agent, such as a pharmaceutical. Using a mucus membrane drug delivery system is a potential benefit over ingestion of pills, tablets or capsules, or repeated injections of pharmacologically active agents, because these traditional methods have initially high concentrations of the pharmacologically active agent, which may be toxic or cause side effects to the target organ or surrounding structures. As time passes, the concentration of the pharmacologically active agent diminishes and another dosage is required to maintain the pharmacologically effective level. Utilizing a mucus membrane drug delivery system including the copolymer of 2-hydroxyethyl methacrylate and 4-hydroxybutyl acrylate as a carrier for a pharmacologically active agent may permit the delivery of an effective amount of a pharmacologically active agent and maintenance of the pharmacologically effective level over longer periods of time.

In another embodiment, the copolymer of 2-hydroxyethyl methacrylate and 4-hydroxybutyl acrylate is blended with a polyalkylene glycol, such as polyethylene glycol, to form a pressure sensitive adhesive. The pressure sensitive adhesive product can be coated onto a substrate, such as a release liner. The pressure sensitive adhesive products can be used as a bandage, tape, wound dressing, surgical drapes and ostomy site dressings.

The copolymer of 2-hydroxyethyl methacrylate and 4-hydroxybutyl acrylate can further be used as a lubricant for speed swimming. The copolymer may be applied to the skin of a swimmer, for example prior to competitive swimming events. As described above, the copolymer may be applied to the skin of a swimmer by spraying the copolymer directly onto the skin.

In another embodiment, the copolymer product of 2-hydroxyethyl methacrylate and 4-hydroxybutyl acrylate, prepared in a solution of water and alcohol, may further contain up to about 10 weight percent of an additional monomer, based on the weight of the copolymeric product. More preferably, the copolymeric product may contain from about 2 to about 4 weight percent of the monomer. The inclusion of up to about 10 weight percent of the monomer increases the cohesive strength of the copolymer, while still maintaining pressure sensitive adhesive properties, skin coating properties, and water resistance. Useful monomers include alkyl acrylates, alkyl methacrylates, hydroxyalkyl acrylates, hydroxyalkyl methacrylates, N-vinyl lactams, vinyl acetate and styrene monomers.

In another embodiment, the present invention provides a method for the preparation of a gel free hydrophilic homopolymer of 4-hydroxybutyl acrylate substantially in the absence of a chain transfer agent. The method includes introducing monomeric 4-hydroxybutyl acrylate into a solution of water and alcohol, and polymerizing the 4-hydroxybutyl acrylate. As described above, the alcohol is selected from one of methanol and ethanol, with ethanol being preferred.

In another embodiment, the invention also provides a method for the preparation of a gel-free homopolymer of 4-hydroxybutyl acrylate in alcohol and substantially in the absence of a chain transfer agent comprising. The monomeric 4-hydroxybutyl acrylate is introduced into an alcohol solution. The monomeric 4-hydroxybutyl acrylate is polymerized to form a polymerization mixture.

In another embodiment, the invention provides substrates coated with the hompolymer of 4-hydroxybutyl acrylate prepared in a solution of water and alcohol and a method of coating a substrate comprising applying to the substrate the polymerization mixture of a hompolymer of 4-hydroxybutyl acrylate prepared in a solution of water and alcohol and, thereafter, removing the alcohol and water from the polymerization mixture. In a preferred embodiment, the substrate is a release liner.

In another embodiment, the invention provides a method of coating a substrate comprising applying to the substrate the polymerization mixture of a hompolymer of 4-hydroxybutyl acrylate prepared in a solution of water and alcohol, and further comprising adding a polyalkylene glycol to the polymerization mixture prior to the removing of the alcohol and water, and thereafter removing the alcohol from the polymerization mixture to form a hydrophilic pressure sensitive adhesive upon removing the alcohol and water from the polymerization mixture. The polyalkylene glycol to be added to the polymerization mixture containing the homopolymer of 4-hydroxybutyl acrylate may be selected from, but should not be limited to, polyethylene glycol, polypropylene glycol, copolymers of ethylene glycol and propylene glycol and mixtures thereof.

It should be noted, however, that the homopolymer of 4-hydroxybutyl acrylate may form a hydrophilic pressure sensitive adhesive even without the addition of a polyalkylene glycol to the polymerization mixture. However, the addition of a polyalkylene glycol to the polymerization mixture prior to removing the solution of alcohol and water may enhance the adhesive properties of the resulting pressure sensitive adhesive.

The homopolymer of 4-hydroxybutyl acrylate prepared in a solution of water and alcohol, like the copolymer of 2-hydroxylethyl methacrylate and 4-hydroxybutyl acrylate, has a wide variety of applications. As described above for the copolymer of 2-hydroxylethyl methacrylate and 4-hydroxybutyl acrylate, the homopolymer of 4-hydroxybutyl acrylate can be used to prepare elastomeric films for medical applications.

The homopolymer of 4-hydroxybutyl acrylate may also be used as a carrier for a transdermal drug delivery system or a mucus membrane drug delivery system. The carrier may be loaded with a pharmacologically active agent, such as a pharmaceutical.

The homopolymer of 4-hydroxybutyl acrylate is also useful for the preparation of creams, lotions, and ointments.

The homopolymer of 4-hydroxybutyl acrylate may also be used to prepare aerosol and spray compositions for direct application to the skin.

The homopolymer of 4-hydroxybutyl acrylate may also be used to prepare a skin friendly cosmetic composition.

The homopolymer of 4-hydroxybutyl acrylate may also be used to prepare a coating comprising the homopolymer. The coating compositions find particular application in the coating of rubber or latex gloves, such as the surgical gloves used in the medical field.

In another embodiment, the homopolymer product of 4-hydroxybutyl acrylate may further contain up to about 10 weight percent of an additional monomer, based on the weight of the polymeric product. More preferably, the polymeric product may contain from about 2 to about 4 weight percent of the monomer. The inclusion of up to about 10 weight percent of the monomer increases the cohesive strength of the homopolymer, while still maintaining pressure sensitive adhesive properties, skin coating properties, and water resistance. Useful monomers include alkyl acrylates, alkyl methacrylates, hydroxyalkyl acrylates, hydroxyalkyl methacrylates, N-vinyl lactams, vinyl acetate and styrene monomers.

In another embodiment, the present invention provides a method for the preparation of a gel free hydrophilic homopolymer of 2-hydroxyethyl methacrylate substantially in the absence of a chain transfer agent. The method includes introducing monomeric 2-hydroxyethyl methacrylate containing no more than about 0.05–0.1% by weight of ethylene glycol dimethacrylate into a solution of water and alcohol, and polymerizing the 2-hydroxyethyl methacrylate.

In a variation of this method, the monomeric 2-hydroxyethyl methacrylate contains no more than about 3% by weight alkylene glycol methacrylate impurities. Preferably, the alkylene glycol methacrylate impurities are selected from, but are not limited to, ethylene glycol dimethacrylate, diethylene glycol monomethacrylate, methacrylic acid and mixtures thereof. Again, the alcohol used in the water/alcohol mixture and into which the monomeric 2-hydroxyethyl methacrylate is introduced includes, but should not be limited to, methanol and ethanol, with ethanol being preferred.

The invention also provides a substrates coated with the homopolymer of 2-hydroxyethyl methacrylate prepared in a solution of water and an alcohol and a method of coating a substrate comprising applying to a substrate a polymerization mixture containing the homopolymer of 2-hydroxyethyl methacrylate and, thereafter, removing the alcohol and water from the polymerization mixture. In one preferred embodiment, the substrate is a release liner.

In another embodiment, the invention provides hydrophilic pressure sensitive adhesives prepared by adding a polyalkylene glycol to the homopolymer of 2-hydroxyethyl methacrylate prepared in a solution of water and alcohol, and a method of coating a substrate comprising applying to a substrate a polymerization mixture containing the homopolymer of 2-hydroxyethyl methacrylate, and further comprising adding a polyalkylene glycol to the polymerization mixture prior to the removing of the alcohol and water, to form a hydrophilic pressure sensitive adhesive upon removing said alcohol and water. In one preferred embodiment, the substrate is a release liner. The polyalkylene glycol that is added to the polymerization mixture containing the homopolymer of 2-hydroxyethyl methacrylate may be selected from, but is not limited to, polyethylene glycol, polypropylene glycol, copolymers of ethylene glycol and propylene glycol and mixtures thereof.

The homopolymer of 2-hydroxyethyl methacrylate prepared in a solution of water and alcohol, like the homopolymer of 4-hydroxybutyl acrylate, has a wide variety of applications. As described above for the homopolymers of 4-hydroxybutyl acrylate, the homopolymer of 2-hydroxyethyl methacrylate can be used to prepare elastomeric films for medical applications.

The homopolymer of 2-hydroxyethyl methacrylate may also be used as a carrier for a transdermal drug delivery system or a mucus membrane drug delivery system. The carrier may be loaded with a pharmacologically active agent, such as a pharmaceutical.

The homopolymer of 2-hydroxyethyl methacrylate is also useful for the preparation of creams, lotions, and ointments.

The homopolymer of 2-hydroxyethyl methacrylate may also be used to prepare aerosol and spray compositions for direct application to the skin.

The homopolymer of 2-hydroxyethyl methacrylate may also be used to prepare a skin friendly cosmetic composition.

The homopolymer of 2-hydroxyethyl methacrylate may also be used to prepare a coating comprising the homopolymer. The coating compositions find particular application in the coating of rubber or latex gloves, such as the surgical gloves used in the medical field.

All of the homopolymers and copolymers prepared in accordance with the methods of the present invention may also be useful as a carrier of an insect repellant for topical application to the skin.

In another embodiment, the homopolymer product of 2-hydroxyethyl methacrylate may further contain up to about 10 weight percent of an additional monomer, based on the weight of the copolymeric product. More preferably, the polymeric product may contain from about 2 to about 4 weight percent of the monomer. The inclusion of up to about 10 weight percent of the monomer increases the cohesive strength of the polymer, while still maintaining pressure sensitive adhesive properties, skin coating properties, and water resistance. Useful monomers include alkyl acrylates, alkyl methacrylates, hydroxyalkyl acrylates, hydroxyalkyl methacrylates, N-vinyl lactams, vinyl acetate and styrene monomers.

2-Hydroxyethyl methacrylate monomer suitable for use in the method of the present invention may also be made by blending industrial grade 2-hydroxyethyl methacrylate monomer from various sources to provide the desired level of impurities. Although less economical, 2-hydroxyethyl methacrylate monomer suitable for use in the method of the present invention may also be made by adding specified amounts of impurities to a higher purity 2-hydroxyethyl methacrylate monomer, to control the properties desired.

The polymers and copolymers of the present invention may be applied to various substrates as described below by any conventional means known in the art such as die coating, roll coating, reverse roll coating, gravure coating, reverse gravure coating, offset gravure coating, Mayer rod or wire wound rod coating, spraying, brushing, and the like. The polymers and copolymers of the present invention may be heated or cooled to facilitate the coating process and to alter the depth or penetration into the substrate.

The amount of the polymers and copolymers of the present invention applied to a substrate may be varied depending upon the characteristics of the substrate, the characteristics desired to be imparted to the substrate, and the particular characteristics of the polymers and copolymers. For economic reasons, it is normally desired to apply the lowest amount of coating to obtain the desired result. Typically, the applied coating weights may, depending on the substrate and intended use, range from about 0.1 to about 100 grams/meter$^2$. For pressure sensitive adhesive applications, the amount is preferably in the range of about 15 grams/meter$^2$ to about 45 grams/meter$^2$. For hydrophilic coating and ink jet coating applications, the amount is preferably from about 1 gram/meter$^2$ to about 25 grams/meter$^2$.

Composites of the present invention may be prepared in various forms including webs which may be in roll form and which can thereafter be cut or slit into strips or sheets of desired dimensions.

As described hereinabove, all of the homopolymers and copolymers prepared in accordance with the methods of the present invention have a high MVTR, are water-insoluble, are flexible, hydrophilic, are water-absorbing, and have good mechanical properties.

All of the homopolymers and copolymers prepared in accordance with the methods of the present invention are suitable for the preparation of and use as elastomeric films, pressure sensitive adhesives, coatings, hydrogels, compositions for topical applications to the skin such as, creams, lotions, ointments, gels, aerosols, sprays, cosmetic compositions, deodorants, and insect repellants.

The unique combination of characteristics makes the homopolymers and copolymer suitable as medical elastomeric films, bandages, tapes, wound care dressings, surgical drapes, ostomy site dressings, as a carrier for transdermal drug delivery systems, and as a carrier for mucus membrane drug delivery systems. Typical pharmacologically active agents include, but are not limited to, corticosteroids, anti-acne agents such as retinoic acid and benzoyl peroxide, anti-infectives such as erythromycin, tetracycline, and clindamycin, anti-fungals such as tolnaftate, undecylenic acid, nystatin, clotrimazole, and fluconazole, antioxidants such as butylated hydroxytoluene, t-butylhydroquinone, tocopherol, surfactants such as sodium lauryl sulfate, UV absorbers such as aminobenzoic acid, benzphenon-8, and benzophenone-4, humectants such as propylene glycol, glycerin, polyethylene glycol, and butylene glycol, alpha hydroxy acids, and emollients such as castor oil, mineral oil, petroleum cetyl palmitate, cetyl alcohol, and stearyl alcohol.

The homopolymers and copolymers prepared in accordance with the methods of the present invention are also useful as a protective coating for skin prior to the application of bandages, tapes or medical devices to the skin.

Another embodiment involves a processes for the preparation of gel-free, water insoluble copolymers that can be subsequently converted to gel-free, hydrophilic, water soluble copolymers by pH adjustment. The copolymer products of the present invention can be prepared from an inexpensive industrial or technical grade 2-hydroxyethyl methacrylate monomer source that contains low levels of ethylene glycol dimethacrylate impurity.

The gel-free, water insoluble copolymers of the present invention can be subjected to a leaching process to substantially remove residual unreacted monomer from the copolymerization mixture to achieve a copolymer product having even lower residual monomer content. While the copolymers of the present invention have many uses, the copolymer products having low residual monomer content are especially useful in the formulation of cosmetic products for application to the skin and hair, and of dermatological products for use in skin and hair care applications.

In one embodiment, the present invention provides a method for the preparation of a gel-free, water insoluble copolymer of 2-hydroxyethyl methacrylate and acrylic acid or methacrylic acid substantially in the absence of a chain transfer agent. The method of producing the gel-free copolymer includes introducing monomeric 2-hydroxyethyl methacrylate containing ethylene glycol dimethacrylate impurities up to about 0.15% by weight of the monomer, and at least one of acrylic acid or methacrylic acid into a solution of water and alcohol. The monomeric 2-hydroxyethyl methacrylate and monomeric acrylic acid and/or methacrylic acid are polymerized to form a polymerization mixture containing a copolymer of 2-hydroxyethyl methacrylate and acrylic acid and/or methacrylic acid.

The method of preparing the gel-free, water insoluble copolymer of 2-hydroxyethyl methacrylate and acrylic acid and/or methacrylic acid can utilize monomeric 2-hydroxyethyl methacrylate containing ethylene glycol dimethacrylate impurities in the range of about 0.05% to about 0.1%, by weight of the 2-hydroxyethyl methacrylate monomer.

The method of preparing the gel-free, water insoluble copolymer of 2-hydroxyethyl methacrylate and acrylic acid and/or methacrylic acid may also utilize monomeric 2-hydroxyethyl methacrylate that contains impurities in a total amount of no more than about 3% by weight of the monomer, where the impurities include ethylene glycol dimethacrylate, diethylene glycol monomethacrylate, methacrylic acid and mixtures of these impurities.

2-Hydroxyethyl methacrylate monomer suitable for use in the method of the present invention may also be made by blending industrial grade 2-hydroxyethyl methacrylate monomer from various sources to provide the desired level of impurities. Although less economical, 2-hydroxyethyl methacrylate monomer suitable for use in the method of the present invention may also be made by adding specified amounts of impurities to a higher purity 2-hydroxyethyl methacrylate monomer, to control the properties desired.

As described above, the copolymer of 2-hydroxyethyl methacrylate and acrylic or methacrylic acid is prepared in a solution of alcohol and water. The alcohol used in the inventive method may include $C_1$–$C_4$ lower alcohols. Preferably, the alcohol used in the copolymerization of 2-hydroxyethyl methacrylate and acrylic acid and/or methacrylic acid, according to the inventive method, is ethanol.

The method for the preparation of a gel-free, water insoluble copolymer of 2-hydroxyethyl methacrylate and methacrylic or acrylic acid occurs substantially in the absence of a chain transfer agent. Polymerization is induced by free radical initiation using a suitable free radical polymerization initiator. The initiator preferably should be soluble in alcohol, water and the monomer mixture. The initiator is added to the alcohol/water solution containing the mixture of the monomeric 2-hydroxyethyl methacrylate and acrylic or methacrylic acid in an amount effective to initiate copolymerization. Suitable initiators include dissociative initiators and redox initiators. Suitable dissociative initiators that may be used in the present invention include, but are not limited to, persulfates such as ammonium persulfate, potassium persulfate and sodium persulfate, hydrogen peroxide, tertbutyl hydroperoxide, and azo compounds such as 4,4'-azobis(4-cyanovaleric acid). Redox initiators include, but are not limited to, persulfates with bisulfite, such as sodium persulfate with sodium metabisulfite, hydrogen peroxide with ferrous ion, sulfite ion, bisulfite ion or ascorbic acid, and hydroperoxides with sulfoxylates, such as tert-butyl hydroperoxide with sodium formaldehyde sulfoxylate.

The gel-free, water insoluble copolymer of 2-hydroxyethyl methacrylate and acrylic or methacrylic acid may be subjected to a conventional leaching process to remove unreacted, residual monomer from the polymerization mixture. Typically, a desired amount of water is added to the polymerization mixture to precipitate the copolymer product. The effluent forms on the surface of the copolymer product and is easily decanted off. Thereafter, the copolymer product may be redissolved with a suitable diluent and then precipitated again. The diluents that can be used to redissolve the copolymer product preferably include, but are not limited to, lower alcohols, alkylene glycols and polyalkylene glycols. Preferably, ethanol and polypropylene glycol are used to redissolve the copolymer product during the leaching process.

The gel-free, water insoluble, leached copolymer of 2-hydroxyethyl methacrylate and acrylic or methacrylic acid is converted to a hydrophilic, gel-free, water soluble copolymer by pH adjustment with a suitable base. According to the present invention, the water insoluble copolymer can be converted to a water soluble copolymer by adjusting the pH of the copolymer to a pH of greater than about 4.5. Preferably, the pH of the copolymer is adjusted to a pH in the range of about 5.5 to about 7.5. Suitable bases that can be used to adjust the pH of the copolymerization mixture include, but are not limited to, hydroxides such as ammonium hydroxide, potassium hydroxide, sodium hydroxide and alcohol amines, such as triethanolamine.

In another embodiment, the present invention provides a method for the preparation of a pressure sensitive adhesive formulation. The method includes preparing a gel-free, water insoluble copolymer of 2-hydroxyethyl methacrylate and acrylic or methacrylic acid. The method utilizes monomeric 2-hydroxyethyl methacrylate containing ethylene glycol dimethacrylate impurity up to about 0.15 weight %, based on the weight of the monomer, to prepare a copolymer of 2-hydroxyethyl methacrylate and acrylic or methacrylic acid. The monomeric 2-hydroxyethyl methacrylate that is useful in the inventive method may contain ethylene glycol dimethacrylate impurity in the range of about 0.05% to about 0.1% by weight of the monomer. Furthermore, the 2-hydroxyethyl methacrylate contains alkylene glycol methacrylate impurities in the range of about 3%, based on the weight of the monomer. Preferably, the alkylene glycol impurities are selected from the group consisting of ethylene glycol dimethacrylate, diethylene glycol monomethacrylate, methacrylic acid and mixtures thereof, in a total amount of no more than about 3% by weight of monomer.

The copolymer is then leached as described above. A polyalkylene glycol is then added to the copolymerization mixture, and the alcohol and water is substantially removed from the polymerization mixture to form a hydrophilic pressure sensitive adhesive. Suitable polyalkylene glycols that can be added to the copolymerization mixture to form the pressure sensitive adhesive include polyethylene glycol, polypropylene glycol and copolymers of polyethylene glycol and polypropylene glycol. Preferably, the polyalkylene glycol used to prepare the pressure sensitive adhesive is polyethylene glycol. The polyalkylene glycol, such as polyethylene glycol, can be added to the copolymerization mixture in an amount ranging from about 40% to about 70% by weight, based on the weight of the copolymer and the polyalkylene glycol. Furthermore, the pH of the copolymer product can be adjusted, as described above, to render the copolymer product water soluble prior to the addition of the polyalkylene to the polymerization mixture. The hydrophilic pressure sensitive adhesives formed by this method have utility in many label and tape applications, and is particularly suitable for medical applications.

In a further embodiment, the present invention provides a method for the preparation of a flexible hydrophilic coating including a gel-free copolymer of 2-hydroxyethyl methacrylate and one of acrylic or methacrylic acid, produced substantially in the absence of a chain transfer agent. The method comprises introducing monomeric 2-hydroxyethyl methacrylate containing ethylene glycol dimethacrylate impurities up to about 0.15 weight %, based on the weight of the monomer into a solution of alcohol and water. The monomers are copolymerized to form a polymerization mixture. The polymerization mixture is then leached to remove residual monomer. A suitable flexiblizing agent is added to the copolymerization mixture to impart a flexibility property to the copolymer, and then the alcohol and water is removed to form a hydrophilic, flexible coating. Suitable flexiblizing agents include, for example, alkylene glycols and glycerin. Preferably, the flexiblizing agents that are added to the copolymerization mixture to form the flexible skin coating are propylene glycol and glycerin. The flexiblizing agent should be added to the copolymerization mixture in amount sufficient to impart a desired level of flexibility to the copolymer. Preferably, the flexiblizing agent is added to the polymerization mixture in an amount ranging from about 10% to about 50% by weight of the polymer, most preferably the flexiblizing agent is added to the polymerization mixture in amount of about 25%, by weight of the polymer.

The monomeric 2-hydroxyethyl methacrylate that is useful in the inventive method may contain ethylene glycol dimethacrylate impurity in the range of about 0.05% to about 0.1% by weight of the monomer. Furthermore, the 2-hydroxyethyl methacrylate contains alkylene glycol methacrylate impurities in the range of about 3%, based on the weight of the monomer. Preferably, the alkylene glycol impurities are selected from the group consisting of ethylene glycol dimethacrylate, diethylene glycol monomethacrylate, methacrylic acid and mixtures thereof, in a total amount of no more than about 3% by weight of monomer. Furthermore, the pH of the copolymer product can be adjusted, as described above, to render the copolymer product water soluble prior to the addition of the flexibilizing agent to the polymerization mixture. The flexible hydrophilic coating formed by this method has utility in skin-friendly applications in which a high Moisture Vapor Transmission Rate (MVTR) is needed together with protective, skin barrier properties. The coating is also suitable for printable coatings, such as inkjet coatings for paper, plastic film, and the like.

In another embodiment, the present invention provides a method for the preparation of a gel free, water insoluble copolymer of 2-hydroxyethyl methacrylate, 4-hydroxybutyl acrylate and acrylic and/or methacrylic acid. The method includes introducing monomeric 2-hydroxyethyl methacrylate containing up to about 0.15 weight % of ethylene glycol dimethacrylate impurity, based on the weight of the monomer, monomeric 4-hydroxybutyl acrylate and monomeric acrylic and/or methacrylic acid into a solution of alcohol and water, and copolymerizing these monomers to form a polymerization mixture. The alcohol is selected from lower alcohols, and is preferably selected from one of methanol and ethanol. More preferably, the lower alcohol used is ethanol.

The method of a preparing the gel free, water insoluble copolymer of 2-hydroxyethyl methacrylate, 4-hydroxybutyl acrylate and acrylic and/or methacrylic acid may include using monomeric 2-hydroxyethyl methacrylate containing 0.05 to 0.1% by weight of ethylene glycol dimethacrylate impurities, based on the weight of the monomer.

The method of preparing the gel free, water insoluble copolymer of 2-hydroxyethyl methacrylate, 4-hydroxybutyl acrylate and acrylic and/or methacrylic acid may include using monomeric 2-hydroxyethyl methacrylate that contains impurities in a total amount of no more than about 3% by weight of the monomer, where the impurities include ethylene glycol dimethacrylate, diethylene glycol monomethacrylate, methacrylic acid and mixtures of these impurities.

A 2-hydroxyethyl methacrylate monomer that is particularly suitable for use in the preparation of a copolymer of 2-hydroxyethyl methacrylate, 4-hydroxybutyl acrylate and acrylic and/or methacrylic acid is available from Mitsubishi Rayon, Japan. The Mitsubishi 2-hydroxyethyl methacrylate monomer contains less than 0.15% by weight of ethylene glycol dimethacrylate impurity, based on the weight of the monomer. The controlled level of impurities in the 2-hydroxyethyl methacrylate monomer permits the preparation of the gel-free polymer, without the need for using a very expensive, ultra-pure 2-hydroxyethyl methacrylate monomer source.

The method for the preparation of a gel-free, water insoluble copolymer of 2-hydroxyethyl methacrylate, 4-hydroxybutyl acrylate and methacrylic or acrylic acid occurs substantially in the absence of a chain transfer agent. Polymerization is induced by free radical initiation using a suitable free radical polymerization initiator. The initiator is added to the alcohol/water solution containing the mixture of the monomeric 2-hydroxyethyl methacrylate, 4-hydroxybutyl acrylate and acrylic or methacrylic acid in an amount effective to initiate copolymerization. The initiator preferably should be soluble in alcohol, water and the monomer mixture. Suitable initiators for the copolymerization of the monomeric 2-hydroxyethyl methacrylate, 4-hydroxybutyl acrylate and acrylic or methacrylic acid that are soluble in water include, but are not limited to, dissociative initiators and redox initiators. Suitable dissociative initiators that may be used in the present invention include, but are not limited to, persulfates such as ammonium persulfate, potassium persulfate and sodium persulfate, hydrogen peroxide, tert-butyl hydroperoxide, and azo compounds such as 4,4'-azobis (4-cyanovaleric acid). Redox initiators include, but are not limited to, persulfates with bisulfite, such as sodium persulfate with sodium metabisulfite, hydrogen peroxide with ferrous ion, sulfite ion, bisulfite ion or ascorbic acid, and hydroperoxides with sulfoxylates, such as tert-butyl hydroperoxide with sodium formaldehyde sulfoxylate.

The gel-free, water insoluble copolymer of 2-hydroxyethyl methacrylate, 4-hydroxybutyl acrylate and acrylic or methacrylic acid may be subjected to a conventional leaching process to substantially remove unreacted, residual monomer from the polymerization mixture. Typically, a desired amount of water is added to the polymerization mixture to precipitate the copolymer product. The effluent forms on the surface of the copolymer product and is decanted off. Thereafter, the copolymer product is redissolved with a suitable diluent, followed by further precipitation and decanting. The diluents that can be used to redissolve the copolymer product preferably include, but are not limited to, lower alcohols, alkylene glycols and polyalkylene glycols. Preferably, ethanol and polypropylene glycol are used to redissolve the copolymer product during the leaching process.

The gel-free, water insoluble, leached copolymer of 2-hydroxyethyl methacrylate, 4-hydroxybutyl acrylate and acrylic or methacrylic acid can be converted to a hydrophilic, gel-free, water soluble copolymer by pH adjustment with a suitable base. According to the present invention, the pH of the copolymerization mixture need only be adjusted to a pH at which the water insoluble copolymer is converted to a water soluble copolymer. Preferably, the water insoluble copolymer can be converted to a water soluble copolymer by adjusting the pH of the copolymer to a pH of greater than about 4.5. More preferably, the pH of the copolymer can be adjusted to a pH in the range of about 5.5 to about 7.5. The pH adjustment of the copolymer can be achieved through the addition of a suitable base to a water/alcohol solution containing the copolymer or to a water/alkylene glycol solution containing the copolymer. Alternatively, the pH of the copolymer can be adjusted by redissolving the precipitated copolymer with a suitable base. Suitable bases that can be used to adjust the pH of the copolymer include, but are not limited to, hydroxides such as ammonium hydroxide, potassium hydroxide and sodium hydroxide, and alcohol amines, such as triethanolamine.

In one embodiment, the present invention provides a method for the preparation of a pressure sensitive adhesive formulation. The method includes preparing a gel-free, water insoluble copolymer of 2-hydroxyethyl methacrylate, 4-hydroxybutyl acrylate and acrylic or methacrylic acid. The method utilizes monomeric 2-hydroxyethyl methacrylate containing ethylene glycol dimethacrylate impurities up to about 0.15 weight %, based on the weight of the monomer. The monomeric 2-hydroxyethyl methacrylate that is useful in the inventive method may contain ethylene glycol dimethacrylate impurity in the range of about 0.05% to about 0.1% by weight of the monomer. Furthermore, the 2-hydroxyethyl methacrylate contains alkylene glycol methacrylate impurities in the range of about 3%, based on the weight of the monomer. Preferably, the alkylene glycol impurities are selected from the group consisting of ethylene glycol dimethacrylate, diethylene glycol monomethacrylate, methacrylic acid and mixtures thereof, in a total amount of no more than about 3% by weight of monomer. The monomeric 2-hydroxeythyl methacrylate, 4-hydroxybutyl acrylate and acrylic or methacrylic acid are copolymerized to form a polymerization mixture.

A polyalkylene glycol is then added to the copolymerization mixture and the alcohol and water is substantially removed to form a hydrophilic pressure sensitive adhesive. Suitable polyalkylene glycols that can be added to the copolymer to form the pressure sensitive adhesive include polyethylene glycol, polypropylene glycol and copolymers of polyethylene glycol and polypropylene glycol. Preferably, the polyalkylene glycol used to prepare the pressure sensitive adhesive is polyethylene glycol. The polyalkylene glycol, such as polyethylene glycol, can be added to the copolymerization mixture in an amount ranging from about 40% to about 70% by weight, based on the weight of the copolymer and the polyalkylene glycol. Prior to the addition of the polyalkylene glycol to the polymerization mixture, the copolymer product can be leached, as described above, to substantially remove residual monomer. Furthermore, the pH of the copolymer product can be adjusted to render the copolymer product water soluble before addition of the polyalkylene glycol to the polymerization mixture. The hydrophilic pressure sensitive adhesives formed by this method have utility in many label and tape applications, and is particularly suitable for medical applications.

In a further embodiment, the present invention provides a method for the preparation of a flexible hydrophilic coating comprising a gel-free copolymer of 2-hydroxyethyl methacrylate, 4-hydroxybutyl acrylate and one of acrylic or methacrylic acid, produced substantially in the absence of a chain transfer agent. The method comprises introducing monomeric 2-hydroxyethyl methacrylate containing ethylene glycol dimethacrylate impurities up to about 0.15 weight %, based on the weight of the monomer, monomeric 4-hydroxybutyl acrylate and monomeric acrylic and/or methacrylic acid into a solution of alcohol and water. The monomeric 2-hydroxyethyl methacrylate that is useful in the inventive method may contain ethylene glycol dimethacrylate impurity in the range of about 0.05% to about 0.1% by weight of the monomer. Furthermore, the 2-hydroxyethyl methacrylate contains alkylene glycol methacrylate impurities in the range of about 3%, based on the weight of the monomer. Preferably, the alkylene glycol impurities are selected from the group consisting of ethylene glycol dimethacrylate, diethylene glycol monomethacrylate, methacrylic acid and mixtures thereof, in a total amount of no more than about 3% by weight of monomer.

The monomers are copolymerized to form a polymerization mixture. A suitable flexiblizing agent is added to the copolymerization mixture to impart a flexibility property to the copolymer, and the alcohol and water is removed to for a hydrophilic, flexible coating. Suitable flexiblizing agents include, for example, alkylene glycols and glycerin. Preferably, the flexiblizing agents that are added to the copolymerization mixture to form the flexible skin coating are propylene glycol and glycerin. The flexiblizing agent should be added to the copolymerization mixture in amount sufficient to impart a desired level of flexibility to the copolymer. Preferably, the flexiblizing agent is added to the polymerization mixture in an amount ranging from about 10% to about 50% by weight of the polymer, preferably the flexiblizing agent is added to the polymerization mixture in amount of about 25%, by weight of the polymer The flexible hydrophilic coating formed by this method has utility in skin-friendly applications in which a high Moisture Vapor Transmission Rate (MVTR) is needed together with protective, skin barrier properties. The coating is also suitable for printable coatings, such as inkjet coatings for paper, plastic film, and the like.

The copolymer of 2-hydroxyethyl methacrylate, 4-hydroxybutyl acrylate and acrylic and/or methacrylic acid is a hydrophilic copolymer that, before pH adjustment, is insoluble in water and does not require crosslinking for water resistance. In addition, the copolymer of 2-hydroxyethyl methacrylate, 4-hydroxybutyl acrylate and methacrylic acid is flexible enough to form a flexible coating or film for medical and skin care or skin protection applications without the need for the addition of glycerin. The flexible coating comprising the copolymer of 2-hydroxyethyl methacrylate, 4-hydroxybutyl acrylate and methacrylic acid is also useful as a rubber or latex glove coating, with particular usefulness in wet-donning applications. Rubber or latex gloves require the ability of donning, that is, the ability to slide a glove on and off the surface of the skin with minimal friction. The copolymer of 2-hydroxyethyl methacrylate, 4-hydroxybutyl acrylate and methacrylic acid provides a flexible, non-tacky glove coating that allows the donning, wet or dry, of the rubber or latex glove with minimal blocking and without undue friction or clinging.

The present invention, in one embodiment, provides a gel-free, hydrophilic copolymer of 2-hydroxyethyl methacrylate, 4-hydroxybutyl acrylate and methacrylic acid that does not to be plasticized. The copolymer of 2-hydroxyethyl methacrylate, 4-hydroxybutyl acrylate and acrylic and/or methacrylic acid, before pH adjustment, is a water-insoluble, water-absorbing, amphiphilic, elastic, abrasion resistant and has improved mechanical properties. It should be noted, however, that while the copolymer of 2-hydroxyethyl methacrylate, 4-hydroxybutyl acrylate and methacrylic acid alone can be flexible enough to form a flexible skin coating, a desired flexiblizing agent, for example, glycerin or an alkyl glycol can be added to the copolymer to further enhance the performance as a skin coating.

A method for the preparation of hydrophilic, gel-free, water insoluble copolymer of 2-hydroxyethyl methacrylate and 4-hydroxybutyl acrylate substantially in the absence of a chain transfer agent is also included in the present invention. According to this embodiment, the copolymer of 2-hydroxyethyl methacrylate and 4-hydroxybutyl acrylate is substantially free of monoalcohol. The method includes introducing monomeric 2-hydroxyethyl methacrylate containing ethylene glycol dimethacrylate impurities up to about 0.15% by weight of the monomer and monomeric 4-hydroxybutyl acrylate into a solution of water and a monoalcohol. The monomeric 2-hydroxyethyl methacrylate and the 4-hydroxybutyl acrylate are then copolymerized in the solution of water and the monoalcohol to form a polymerization mixture. The copolymer is leached to remove residual unreacted monomer. The monoalcohol present in the leached copolymer product of 2-hydroxyethyl methacrylate and 4-hydroxybutyl acrylate is substantially replaced by redissolving the copolymer in a polyhydric alcohol, followed by further leaching and decanting, to produce a substantially monoalcohol-free copolymer of 2-hydroxyethyl methacrylate and 4-hydroxybutyl acrylate.

As used in the specification, the term "monoalcohol" refers to a monohydric alcohol. Without limitation, the monoalcohol used in the polymerization process is preferably selected from monohydric $C_1$–$C_4$ alkyl alcohols. More preferably, the monoalcohol used in the copolymerization of 2-hydroxyethyl methacrylate and 4-hydroxybutyl acrylate is selected from methanol and ethanol. The term "polyhydric alcohol" refers to an alcohol having more than one hydroxyl group and, is intended to encompass both dihydric alcohols, which have two hydroxyl groups, and alcohols having more than two hydroxyl groups.

The method of preparing the gel-free, water insoluble copolymer of 2-hydroxyethyl methacrylate and 4-hydroxybutyl acrylate, in another embodiment, can utilize monomeric 2-hydroxyethyl methacrylate containing ethylene glycol dimethacrylate impurities in the range of about 0.05% to about 0.1%, by weight of the 2-hydroxyethyl methacrylate monomer.

The method of preparing the gel-free, water insoluble copolymer of 2-hydroxyethyl methacrylate and 4-hydroxybutyl acrylate may also utilize monomeric 2-hydroxyethyl methacrylate that contains impurities in a total amount of no more than about 3% by weight of the monomer, where the impurities include ethylene glycol dimethacrylate, diethylene glycol monomethacrylate, methacrylic acid and mixtures of these impurities.

The method of forming the gel-free, water insoluble copolymer of 2-hydroxyethyl methacrylate and 4-hydroxybutyl acrylate employs the use of an industrial grade 2-hydroxyethyl methacrylate monomer. A 2-hydroxyethyl methacrylate industrial grade monomer that is particularly suitable for use in the method is available from Mitsubishi Rayon, Japan. This 2-hydroxyethyl methacrylate monomer contains less than about 0.15% by weight of ethylene glycol dimethacrylate impurity, based on the weight of the monomer.

2-Hydroxyethyl methacrylate monomer suitable for use in the method of preparing a copolymer of 2-hydroxyethyl methacrylate and 4-hydroxybutyl acrylate may also be made by blending industrial grade 2-hydroxyethyl methacrylate monomer from various sources to provide the desired level of impurities. Although less economical, 2-hydroxyethyl methacrylate monomer suitable for use in the method of the present invention may also be made by adding specified amounts of impurities to a higher purity 2-hydroxyethyl methacrylate monomer, to control the properties desired.

The preparation of a gel-free, water insoluble copolymer of 2-hydroxyethyl methacrylate and 4-hydroxybutyl acrylate occurs substantially in the absence of a chain transfer agent. Polymerization is induced by free radical initiation using a suitable free radical polymerization initiator. The initiator preferably should be soluble in alcohol, water and the monomer mixture. The initiator is added to the alcohol/water solution containing the mixture of the monomeric 2-hydroxyethyl methacrylate and 4-hydroxybutyl acrylate in an amount effective to initiate copolymerization. Suitable initiators include dissociative initiators and redox initiators. Suitable dissociative initiators that may be used in the present invention include, but are not limited to, persulfates such as ammonium persulfate, potassium persulfate and sodium persulfate, hydrogen peroxide, tert-butyl hydroperoxide, and azo compounds such as 4,4'-azobis(4-cyanovaleric acid). Redox initiators include, but are not limited to, persulfates with bisulfite, such as sodium persulfate with sodium metabisulfite, hydrogen peroxide with ferrous ion, sulfite ion, bisulfite ion or ascorbic acid, and hydroperoxides with sulfoxylates, such as tert-butyl hydroperoxide with sodium formaldehyde sulfoxylate.

As described above, the gel-free, water insoluble copolymer of 2-hydroxyethyl methacrylate and 4-hydroxybutyl acrylate may be subjected to a conventional leaching process to substantially remove unreacted, residual monomer from the polymerization mixture. Typically, a desired amount of water is added to the polymerization mixture to precipitate the copolymer product. The effluent forms on the surface of the copolymer product and is easily decanted off. Thereafter, the copolymer product is redissolved with a suitable diluent, and the redissolved copolymer may be subjected to further precipitation and decanting. Preferably, polyhydric alcohols are used to redissolve the copolymer product. Suitable polyhydric alcohols that can be used to redissolve the copolymer product include, but are not limited to, alkylene glycols, alkyl ethers of alkylene glycols, diols, glycerin and alkyl esters of glycerin. By redissolving the copolymer product in a polyhydric alcohol, the monoalcohol present in the copolymer product is substantially replaced by the polyhydric alcohol to produce a substantially monoalcohol free copolymer of 2-hydroxyethyl methacrylate and 4-hydroxybutyl acrylate.

The preferred alkylene glycols that can be used include, but are not limited to ethylene glycol and propylene glycol, with propylene glycol being more preferred. Where alkyl ethers of alkylene glycols are used to redissolve the copolymer product, the alkyl ethers of alkylene glycols may be selected from ethylene glycol monomethyl ether, ethylene glycol monoethyl ether, propylene glycol monomethyl ether and propylene glycol monoethyl ether. Furthermore, diols may be used to redissolve the copolymer product of 2-hydroxyethyl methacrylate and 4-hydroxybutyl acrylate. Suitable diols that may be utilized include, but are not limited to, 1,3-butanediol, 1,4-butanediol, 2-methyl-2,4-pentanediol, 2,5-hexanediol and 2,4-heptanediol. Glycerin and alkyl esters of glycerin may be utilized to redissolve the copolymer product of 2-hydroxyethyl methacrylate and 4-hydroxybutyl acrylate. If utilized, the alkyl esters of glycerin may include glycerin monolaurate, glycerin monooleate and glycerin monostearate. Preferably, polypropylene glycol or glycerin are used to redissolve the copolymer product.

A method is also included for the preparation of substantially monoalcohol-free, gel-free, water insoluble, hydrophilic copolymer of 2-hydroxyethyl methacrylate and 4-hydroxybutyl acrylate substantially in the absence of a chain transfer agent comprising. The method, according this embodiment, includes introducing monomeric 2-hydroxyethyl methacrylate containing ethylene glycol dimethacrylate impurities up to about 0.15% by weight, based on the weight of the monomer, and monomeric 4-hydroxybutyl acrylate into a solution of water and polyhydric alcohol. The monomeric 2-hydroxyethyl methacrylate and the 4-hydroxybutyl acrylate are copolymerized in the solution of water and polyhydric alcohol to form a polymerization mixture containing the copolymer.

The polyhydric alcohol in which the copolymerization of 2-hydroxyethyl methacrylate and 4-hydroxybutyl acrylate occurs includes, but is not limited to, alkylene glycols, alkyl ethers of alkylene glycols, diols, glycerin and alkyl esters of glycerin. The copolymer may be leached, preferably with water, to remove residual monomer. The polyhydric alcohol may be replaced by a monoalcohol by redissolving the copolymer in a monoalcohol, followed by leaching and decanting.

A method is provided for the preparation of a pressure sensitive adhesive including the copolymer of 2-hydroxyethyl methacrylate and 4-hydroxybutyl acrylate. The method includes preparing a gel-free, water insoluble copolymer of 2-hydroxyethyl methacrylate and 4-hydroxybutyl acrylate. The method utilizes monomeric 2-hydroxyethyl methacrylate containing ethylene glycol dimethacrylate impurity up to about 0.15 weight %, based on the weight of the monomer, to prepare a copolymer of 2-hydroxyethyl methacrylate and 4-hydroxybutyl acrylate. The copolymer is then leached as described above. A polyalkylene glycol is then added to the copolymerization mixture, and the alcohol and water is substantially removed from the polymerization mixture to form a hydrophilic pressure sensitive adhesive. Suitable polyalkylene glycols that can be added to the copolymerization mixture to form the pressure sensitive adhesive include polyethylene glycol, polypropylene glycol and copolymers of polyethylene glycol and polypropylene glycol. Preferably, the polyalkylene glycol used to prepare the pressure sensitive adhesive is polyethylene glycol. The polyalkylene glycol, such as polyethylene glycol, can be added to the copolymerization mixture in an amount ranging from about 40% to about 70% by weight, based on the weight of the copolymer and the polyalkylene glycol. The hydrophilic pressure sensitive adhesives formed by this method have utility in many label and tape applications, and is particularly suitable for medical applications.

The method of preparing the pressure sensitive adhesive including the gel-free, water insoluble copolymer of 2-hydroxyethyl methacrylate and 4-hydroxybutyl acrylate can also utilize monomeric 2-hydroxyethyl methacrylate containing ethylene glycol dimethacrylate impurities in the range of about 0.05% to about 0.1%, by weight of the 2-hydroxyethyl methacrylate monomer.

The method of preparing the pressure sensitive adhesive including the gel-free, water insoluble copolymer of 2-hydroxyethyl methacrylate and 4-hydroxybutyl acrylate may further utilize monomeric 2-hydroxyethyl methacrylate that contains impurities in a total amount of no more than about 3% by weight of the monomer, where the impurities include ethylene glycol dimethacrylate, diethylene glycol monomethacrylate, methacrylic acid and mixtures of these impurities.

The present invention also provides a method for the preparation of a flexible hydrophilic coating including a gel-free, water insoluble copolymer of 2-hydroxyethyl methacrylate and 4-hydroxybutyl acrylate, produced substantially in the absence of a chain transfer agent. The method comprises introducing monomeric 2-hydroxyethyl methacrylate containing ethylene glycol dimethacrylate impurities up to about 0.15 weight %, based on the weight of the monomer into a solution of alcohol and water. The monomers are copolymerized to form a polymerization mixture. The polymerization mixture is then leached to remove residual monomer. A suitable flexiblizing agent is added to the copolymerization mixture to impart a flexibility property to the copolymer, and then the alcohol and water is removed to form a hydrophilic, flexible coating. Suitable flexiblizing agents include, for example, alkylene glycols and glycerin. Preferably, the flexiblizing agents that are added to the copolymerization mixture to form the flexible skin coating are propylene glycol and glycerin. The flexiblizing agent should be added to the copolymerization mixture in amount sufficient to impart a desired flexiblizing property to the copolymer. Preferably, the flexiblizing agent is added to the polymerization mixture in an amount ranging from about 10% to about 50% by weight of the polymer, most preferably the flexiblizing agent is added to the polymerization mixture in amount of about 25%, by weight of the polymer. It should be noted, however, that while the copolymer of 2-hydroxyethyl methacrylate, and 4-hydroxybutyl acrylate alone can be flexible enough to form a flexible skin coating, a desired flexiblizing agent, for example, glycerin or an alkylene glycol can be added to the copolymer to further enhance the performance as a skin coating.

A method for the preparation of substantially monoalcohol-free, gel-free, water insoluble, hydrophilic homopolymer of 2-hydroxyethyl methacrylate substantially in the absence of a chain transfer agent is also provided. The method comprises introducing monomeric 2-hydroxyethyl methacrylate containing ethylene glycol dimethacrylate impurities up to about 0.15% by weight, based on the weight of the monomer, into a solution of water and a monoalcohol. The monomeric 2-hydroxyethyl methacrylate is polymerized to form a polymerization mixture containing the homopolymer. The homopolymer of 2-hydroxyethyl methacrylate may be leached to substantially remove residual monomer, followed by substantially replacing the monoalcohol with a polyhydric alcohol.

The same polyhydric alcohols used to redissolve the copolymer of 2-hydroxyethyl methacrylate and 4-hydroxybutyl acrylate and to substantially replace the monoalcohol in that copolymer can be used to redissolve the homopolymer of 2-hydroxyethyl methacrylate and to substantially replace the monoalcohol present in the homopolymer.

The method of preparing the gel-free, hydrophilic, water insoluble polymer of 2-hydroxyethyl methacrylate, in another embodiment, can utilize monomeric 2-hydroxyethyl methacrylate containing ethylene glycol dimethacrylate impurities in the range of about 0.05% to about 0.1%, by weight of the 2-hydroxyethyl methacrylate monomer.

The method of preparing the gel-free, hydrophilic, water insoluble polymer of 2-hydroxyethyl methacrylate may also utilize monomeric 2-hydroxyethyl methacrylate that contains impurities in a total amount of no more than about 3% by weight of the monomer, where the impurities include ethylene glycol dimethacrylate, diethylene glycol monomethacrylate, methacrylic acid and mixtures of these impurities.

The method of forming the gel-free, water insoluble polymer of 2-hydroxyethyl methacrylate employs the use of an industrial grade 2-hydroxyethyl methacrylate monomer. A 2-hydroxyethyl methacrylate industrial grade monomer that is particularly suitable for use in the method is available from Mitsubishi Rayon, Japan. This 2-hydroxyethyl methacrylate monomer contains less than 0.15% by weight of ethylene glycol dimethacrylate impurity, based on the weight of the monomer.

2-Hydroxyethyl methacrylate monomer suitable for use in the method of preparing a homopolymer of 2-hydroxyethyl methacrylate may also be made by blending industrial grade 2-hydroxyethyl methacrylate monomer from various sources to provide the desired level of impurities. Although less economical, 2-hydroxyethyl methacrylate monomer suitable for use in the method of the present invention may also be made by adding specified amounts of impurities to a higher purity 2-hydroxyethyl methacrylate monomer, to control the properties desired.

A method for the preparation of gel-free, hydrophilic homopolymer of 2-hydroxyethyl methacrylate substantially in the absence of a chain transfer agent is also included in the present invention. The method includes introducing monomeric 2-hydroxyethyl methacrylate containing ethylene glycol dimethacrylate impurities up to about 0.15% by weight into a solution of water and a polyhydric alcohol. The 2-hydroxyethyl thacrylate is then polymerized to form a polymerization mixture containing the homopolymer.

The method of preparing the gel-free, hydrophilic, water insoluble polymer of 2-hydroxyethyl methacrylate, in another embodiment, can utilize monomeric 2-hydroxyethyl methacrylate containing ethylene glycol dimethacrylate impurities in the range of about 0.05% to about 0.1%, by weight of the 2-hydroxyethyl methacrylate monomer.

The method of preparing the gel-free, hydrophilic, water insoluble polymer of 2-hydroxyethyl methacrylate may also utilize monomeric 2-hydroxyethyl methacrylate that contains impurities in a total amount of no more than about 3% by weight of the monomer, where the impurities include ethylene glycol dimethacrylate, diethylene glycol monomethacrylate, methacrylic acid and mixtures of these impurities.

The method of forming the gel-free, water insoluble polymer of 2-hydroxyethyl methacrylate employs the use of an industrial grade 2-hydroxyethyl methacrylate monomer. A 2-hydroxyethyl methacrylate industrial grade monomer that is particularly suitable for use in the method is available from Mitsubishi Rayon, Japan. This 2-hydroxyethyl methacrylate monomer contains less than 0.15% by weight of ethylene glycol dimethacrylate impurity, based on the weight of the monomer.

2-Hydroxyethyl methacrylate monomer suitable for use in the method of preparing a homopolymer of 2-hydroxyethyl methacrylate may also be made by blending industrial grade 2-hydroxyethyl methacrylate monomer from various sources to provide the desired level of impurities. Although less economical, 2-hydroxyethyl methacrylate monomer suitable for use in the method of the present invention may also be made by adding specified amounts of impurities to a higher purity 2-hydroxyethyl methacrylate monomer, to control the properties desired.

The polyhydric alcohol in which the copolymerization of 2-hydroxyethyl methacrylate and 4-hydroxybutyl acrylate occurs includes, but is not limited to, alkylene glycols, alkyl ethers of alkylene glycols, diols, glycerin and alkyl esters of glycerin.

The preparation of a gel-free, water insoluble homopolymer of 2-hydroxyethyl methacrylate occurs substantially in the absence of a chain transfer agent. Polymerization is induced by free radical initiation using a suitable free radical polymerization initiator. The initiator preferably should be soluble in alcohol, water and the monomer. The initiator is added to the alcohol/water solution containing the monomeric 2-hydroxyethyl methacrylate in an amount effective to initiate polymerization. Suitable initiators include dissociative initiators and redox initiators. Suitable dissociative initiators that may be used in the present invention include, but are not limited to, persulfates such as ammonium persulfate, potassium persulfate and sodium persulfate, hydrogen peroxide, tert-butyl hydroperoxide, and azo compounds such as 4,4'-azobis(4-cyanovaleric acid). Redox initiators include, but are not limited to, persulfates with bisulfite, such as sodium persulfate with sodium metabisulfite, hydrogen peroxide with ferrous ion, sulfite ion, bisulfite ion or ascorbic acid, and hydroperoxides with sulfoxylates, such as tert-butyl hydroperoxide with sodium formaldehyde sulfoxylate.

The gel-free, water insoluble homopolymer of 2-hydroxyethyl methacrylate may subjected to a conventional leaching process to substantially remove unreacted, residual monomer from the polymerization mixture. Typically, a desired amount of water is added to the polymerization mixture to precipitate the polymer product. The effluent forms on the surface of the polymer product and is easily decanted off. Thereafter, the polymer product is redissolved with a suitable diluent, and the redissolved polymer can be subjected to further precipitation and decanting. The diluents that can be used to redissolve the polymer product preferably include, but are not limited to, lower alcohols, alkylene glycols and polyalkylene glycols. Preferably, ethanol and polypropylene glycol are used to redissolve the polymer product during the leaching process. Furthermore, the polyhydric alcohol can be substantially replaced with a monohydric alcohol by redissolving the homopolymer in a monohydric alcohol, followed by further leaching and decanting to drive off the polyhydric alcohol, thus resulting in a copolymer product containing the monohydric alcohol.

The present invention includes a method for the preparation of a pressure sensitive adhesive including the homopolymer of 2-hydroxyethyl methacrylate. The method includes preparing a gel-free, water insoluble homopolymer of 2-hydroxyethyl methacrylate. The method utilizes monomeric 2-hydroxyethyl methacrylate containing ethylene glycol dimethacrylate impurity up to about 0.15 weight %, based on the weight of the monomer, to prepare a homopolymer of 2-hydroxyethyl methacrylate. The homopolymer is then leached as described above to substantially remove residual monomer. A polyalkylene glycol is then added to the polymerization mixture, and the alcohol and water is substantially removed from the polymerization mixture to form a hydrophilic pressure sensitive adhesive. Suitable polyalkylene glycols that can be added to the polymerization mixture to form the pressure sensitive adhesive include polyethylene glycol, polypropylene glycol and copolymers of polyethylene glycol and polypropylene glycol. Preferably, the polyalkylene glycol used to prepare the pressure sensitive adhesive is polyethylene glycol. The polyalkylene glycol, such as polyethylene glycol, can be added to the polymerization mixture in an amount ranging from about 40% to about 70% by weight, based on the weight of the copolymer and the polyalkylene glycol. The hydrophilic pressure sensitive adhesives formed by this method have utility in many label and tape applications, and is particularly suitable for medical applications.

The present invention also provides a method for the preparation of a flexible hydrophilic coating including a gel-free, water insoluble homopolymer of 2-hydroxyethyl methacrylate, produced substantially in the absence of a chain transfer agent. The method comprises introducing monomeric 2-hydroxyethyl methacrylate containing ethylene glycol dimethacrylate impurities up to about 0.15 weight %, based on the weight of the monomer into a solution of alcohol and water. The monomer is polymerized to form a polymerization mixture. The polymerization mixture is then leached to substantially remove residual monomer. A suitable flexiblizing agent is added to the copolymerization mixture to impart a flexibility property to the homopolymer, and then the alcohol and water is removed to form a hydrophilic, flexible coating. Suitable flexiblizing agents include, for example, alkylene glycols and glycerin. Preferably, the flexiblizing agents that are added to the polymerization mixture to form the flexible skin coating are propylene glycol and glycerin. The flexiblizing agent should be added to the polymerization mixture in amount sufficient to impart a desired flexiblizing property to the homopolymer. Preferably, the flexiblizing agent is added to the polymerization mixture in an amount ranging from about 10% to about 50% by weight of the homopolymer, most preferably the flexiblizing agent is added to the polymerization mixture in amount of about 25%, by weight of the polymer.

The copolymer product of 2-hydroxyethyl methacrylate and acrylic and/or methacrylic acid, the copolymer product of 2-hydroxyethyl methacrylate, 4-hydroxybutyl acrylate and acrylic and/or methacrylic acid, the copolymer of 2-hydroxyethyl methacrylate and 4-hydroxybutyl acrylate, and the homopolymer of 2-hydroxyethyl methacrylate may further contain up to about 10 weight percent of an additional monomer, based on the weight of the polymeric product. More preferably, the polymeric product may contain from about 2 to about 4 weight percent of the additional monomer. The inclusion of up to about 10 weight percent of the additional monomer increases the cohesive strength of the polymer product, while still maintaining pressure sensitive adhesive properties, skin coating properties, and water resistance. Useful monomers that may be added to the polymer products of the present invention include, for example, alkyl acrylates, alkyl methacrylates, hydroxyalkyl acrylates, hydroxyalkyl methacrylates, fluorinated alkyl acrylates, including 1H, 1H-triflouroethyl acrylate, 1H, 1H-heptaflourobutyl acrylate and 1H, 1H-pentadecaflourooctyl acrylate, fluorinated alkyl methacrylates including 1H, 1H-triflouroethyl methacrylate, 1H, 1H-heptaflourobutyl methacrylate and 1H, 1H-pentadecaflourooctyl methacrylate, N-vinyl lactam, dimethylaminoethyl acrylate, methylene chloride quaternary salt of dimethylaminoethyl acrylate, diethylaminoethyl acrylate, methylene chloride quaternary salt of diethylaminoethyl acrylate, dimethylaminoethyl methacrylate, methylene chloride quaternary salt of dimethylaminoethyl methacrylate, diethylaminoethyl methacrylate, methylene chloride quaternary salt of diethylaminoethyl methacrylate, vinyl acetate and styrene monomers. The alkyl component of the above monomers is preferably a $C_1$–$C_{17}$ alkyl group.

The copolymer of 2-hydroxyethyl methacrylate and acrylic and/or methacylic acid, or the copolymer of 2-hydroxyethyl methacrylate, 4-hydroxybutyl acrylate, and acrylic and/or methacrylic acid can utilize other polymerizable acid monomers besides acrylic acid and methacrylic acid. Non-limiting examples of other polymerizable acid monomers include, but are not limited to, b-carboxyethyl acrylate, crotonic acid, maleic acid, fumaric acid, and itaconic acid.

In general, the copolymer of 2-hydroxyethyl methacrylate and acrylic and/or methacrylic acid, the copolymer of 2-hydroxyethyl methacrylate, 4-hydroxybutyl acrylate and acrylic and/or methacrylic acid, the copolymer of 2-hydroxyethyl methacrylate and 4-hydroxybutyl acrylate, and the homopolymer of 2-hydroxyethyl methacrylate can be utilized in topical skin formulations, including cosmetic compositions, dermatological preparations and compositions, skin coatings or barriers. Some useful applications of these polymers include use as sprayable carriers for topical application of drugs to the skin. These polymers may also be a component of a cream, including water in oil emulsions and oil in water emulsions; lotions, which are suspensions in water or oil; ointments, which are solutions in petroleum or polyethylene glycol; or aerosols, which are sprayable solutions in water/alcohol and gels.

The polymers may also be a component of a transdermal drug delivery system. Specifically, the polymers can be used as a carrier or vehicle to deliver an effective amount of a pharmacologically active agent (drug) transdermally. In this embodiment, the polymers may be loaded with an effective amount of a pharmacologically active agent and locally placed on the surface of the skin. The transdermal drug delivery system can also include, as known in the art, skin permeation enhancers to facilitate the transdermal delivery of the pharmacologically active agent. The polymers can perform a dual function as a carrier of a pharmacologically active agent and a protective coating or skin barrier.

The polymers can also be sprayed onto the skin before the application of adhesive-coated bandages, tapes, or other adhesive-coated medical devices to prevent irritation of sensitive skin.

The polymers can be used as an elastomeric medical film. Preferably, the polymers can be coated onto a substrate, such as a release liner and dried. The polymers will be self cross-linking with heat treatment. Preferably, the polymers will be self cross-linking by heat treating at a temperature in the range of about 70° C. to about 150° C., more preferably in a temperature range of about 70° C. to about 125° C. The elastomeric medical film can be used directly over a wound on the skin to provide a dressing or barrier. The elastomeric film is soft and pliable, and easily conforms to the contours of human skin.

The polymers may also be included in sun block and sunscreen lotions, creams, sprays and as a carrier or vehicle of ultra-violet (UV) light absorbers, such as aminobenzoic acid, benzophenone-8 and benzophenone-4.

The polymers can be used as a carrier for cosmetic products. Cosmetic compositions including the polymers are easy to apply to and remove from the surface of human skin, are non-greasy, and non-occlusive. Like skin, the polymers are hydrophilic, amphiphilic and elastic.

The polymers can also be included as a component of a nasal spray or other mucus membrane drug delivery systems, as a carrier for a pharmacologically active agent, such as a pharmaceutical. Using a mucus membrane drug delivery system is a potential benefit over ingestion of pills, tablets or capsules, or repeated injections of pharmacologically active agents, because these traditional methods have initially high concentrations of the pharmacologically active agent, which may be toxic or cause side effects to the target organ or surrounding structures. As time passes, the concentration of the pharmacologically active agent diminishes and another dosage is required to maintain the pharmacologically effective level. Utilizing a mucus membrane drug delivery system including the polymers as a carrier for a pharmacologically active agent may permit the delivery of an effective amount of a pharmacologically active agent and maintenance of the pharmacologically effective level over longer periods of time.

The polymers can be blended with a polyalkylene glycol, such as polyethylene glycol, to form a pressure sensitive adhesive. The pressure sensitive adhesive can be coated onto a substrate, such as a release liner, in the formation of a pressure sensitive product. The pressure sensitive adhesive products can be used as a bandage, tape, wound dressing, surgical drape, ostomy site dressing and the like.

In another embodiment, the invention provides a method of coating a substrate comprising applying to a substrate the polymerization mixture any of the polymers that are prepared in a solution of water and alcohol, and further comprising adding a polyalkylene glycol to the polymerization mixture prior to the removing of the alcohol and water, and thereafter forming a hydrophilic pressure sensitive adhesive upon removing the alcohol and water from the polymerization mixture. The polyalkylene glycol to be added to the polymerization mixture includes, but is not limited to, polyethylene glycol, polypropylene glycol, copolymers of ethylene glycol and propylene glycol and mixtures thereof.

The polymers of the present invention may be applied to various substrates as described below by any conventional means known in the art such as die coating, roll coating, reverse roll coating, gravure coating, reverse gravure coating, offset gravure coating, Mayer rod or wire wound rod coating, spraying, brushing, and the like. The polymers of the present invention may be heated or cooled to facilitate the coating process to provide a desired coating of the polymer on the substrate.

Any of the polymer products produced in accordance with the present invention can be dried. The dried polymer may then be pulverized into a powder, or sprayed dried into a powder.

The amount of the polymer that is to applied to a substrate may be varied depending upon the characteristics of the substrate, the characteristics desired to be imparted to the substrate, and the particular characteristics of the polymers and copolymers. For economic reasons, it is normally desired to apply the lowest amount of coating to obtain the desired result. Typically, the applied coating weights may, depending on the substrate and intended use, range from about 0.1 to about 100 grams/meter$^2$. For pressure sensitive adhesive applications, the amount is preferably in the range of about 15 grams/meter$^2$ to about 45 grams/meter$^2$. For hydrophilic coating and ink jet coating applications, the amount is preferably from about 1 gram/meter$^2$ to about 25 grams/meter$^2$.

The substrate which is used in the present invention may be any substrate material such as paper, or polymeric films in the form of sheets and strips, and the like. Preferred types of paper include semi-gloss paper and high gloss paper. In one embodiment, the substrate is a polymeric film. In a preferred embodiment, the substrate is a polymeric film formed from a thermoplastic material. In a more preferred embodiment, the substrate is a polymeric film selected from the group consisting of polystyrene, a polyester, and a polyolefin such as polyethylene or polypropylene.

Composites of the present invention may be prepared in various forms including webs which may be in roll form and which can thereafter be cut or slit into strips or sheets of desired dimensions.

The polymers prepared in accordance with the methods of the present invention are suitable for the preparation of and use as elastomeric films, pressure sensitive adhesives, coatings, precursors ro hydrogels, compositions for topical applications to the skin such as, creams, lotions, ointments, gels, aerosols, sprays, cosmetic compositions, dermatological preparations and composotions, deodorants, and insect repellants.

As mentioned above, the unique combination of characteristics makes the polymers suitable for use in medical elastomeric films, bandages, tapes, wound care dressings, surgical drapes, ostomy site dressings, as a carrier for transdermal drug delivery systems, and as a carrier for mucus membrane drug delivery systems. These medical products can be loaded with a pharmacologically active agent. Typical pharmacologically active agents include, but are not limited to, corticosteroids, anti-acne agents such as retinoic acid and benzoyl peroxide, anti-infectives such as erythromycin, tetracycline, and clindamycin, anti-fungals such as tolnaftate, undecylenic acid, nystatin, clotrimazole, and fluconazole, antioxidants such as butylated hydroxytoluene, t-butylhydroquinone, tocopherol, surfactants such as sodium lauryl sulfate, UV absorbers such as aminobenzoic acid, benzphenon-8, and benzophenone-4, humectants such as propylene glycol, glycerin, polyethylene glycol, and butylene glycol, alpha hydroxy acids, and emollients such as castor oil, mineral oil, petroleum cetyl palmitate, cetyl alcohol, and stearyl alcohol.

In another embodiment, the present invention provides a method for the preparation of a powdered low-gel poly 2-hydroxyethyl methacrylate substantially in the absence of a chain transfer agent is also provided comprising: introducing monomeric 2-hydroxyethyl methacrylate containing ethylene glycol dimethacrylate impurities in the range of 0.05 to 0.1% by weight into water, polymerizing the 2-hydroxyethyl methacrylate, drying said polymerized 2-hydroxyethyl methacrylate, and grinding said dried polymerized 2-hydroxyethyl methacrylate to form a powder.

In another embodiment, the monomeric 2-hydroxyethyl methacrylate contains alkylene glycol methacrylate impurities in the range of no more than 3% by weight.

In a variation of this embodiment, the method for the preparation of a low-gel poly 2-hydroxyethyl methacrylate substantially in the absence of a chain transfer agent, comprises introducing monomeric 2-hydroxyethyl methacrylate containing ethylene glycol dimethacrylate impurities in the range of no more than about 0.05 to 0.1% by weight into water, polymerizing the 2-hydroxyethyl methacrylate to form a polymerization mixture, drying the polymerized 2-hydroxyethyl methacrylate, and grinding the dried polymerized 2-hydroxyethyl methacrylate to form a powder. The dry poly 2-hydroxyethyl methacrylate powder is then blended with a polyalkylene glycol, such as polyethylene glycol, to form a pressure sensitive adhesive, wherein the amount of the polyalkylene glycol used to prepare the pressure sensitive adhesive is from about 40 to about 70% by weight, based on the weight of the dry poly 2-hydroxyethyl methacrylate powder and the polyethylene glycol.

In another embodiment, the 2-hydroxyethyl methacrylate monomer contains alkylene glycol impurities that are selected from the group consisting of ethylene glycol dimethacrylate, diethylene glycol monomethacrylate, methacrylic acid and mixtures thereof, in a total amount of no more than about 3% by weight of monomer.

The hydrophilic pressure sensitive adhesive formed by this method has utility in many label and tape applications, and is particularly suitable for thick medical applications, and as an additive for cosmetic and skin care products. In another variation of this embodiment, the dry poly 2-hydroxyethyl methacrylate powder can be dissolved in alcohol and glycerin can be added to the polymerization mixture in an amount from about 10% to about 50% by weight of the polymer, preferably about 25% by weight of the polymer, and the alcohol removed to form a flexible hydrophilic coating. Before, the alcohol is removed, the solution can be sprayed onto the skin prior to applying a bandage, glove, or the like.

2-Hydroxyethyl methacrylate monomer suitable for use in the method of the present invention may also be made by blending industrial grade 2-hydroxyethyl methacrylate monomer from various sources to provide the desired level of impurities. Although less economical, 2-hydroxyethyl methacrylate monomer suitable for use in the method of the present invention may also be made by adding specified amounts of impurities to a higher purity 2-hydroxyethyl methacrylate monomer, to control the properties desired.

The polymers and copolymers of the present invention may be applied to various substrates as described below by any conventional means known in the art such as die coating, roll coating, reverse roll coating, gravure coating, reverse gravure coating, offset gravure coating, Mayer rod or wire wound rod coating, spraying, brushing, and the like. The polymers and copolymers of the present invention may be heated or cooled to facilitate the coating process and to alter the depth or penetration into the substrate.

The amount of the polymers and copolymers of the present invention applied to a substrate may be varied depending upon the characteristics of the substrate, the characteristics desired to be imparted to the substrate, and the particular characteristics of the polymers and copolymers. For economic reasons, it is normally desired to apply the lowest amount of coating to obtain the desired result. Typically, the applied coating weights may, depending on the substrate and intended use, range from about 0.1 to about 100 grams/meter$^2$. For pressure sensitive adhesive applications, the amount is preferably in the range of about 15 grams/meter$^2$ to about 45 grams/meter$^2$. For hydrophilic coating and ink jet coating applications, the amount is preferably from about 1 gram/meter$^2$ to about 25 grams/meter$^2$.

Composites of the present invention may be prepared in various forms including webs which may be in roll form and which can thereafter be cut or slit into strips or sheets of desired dimensions.

The following examples illustrate the method of preparation of the hydrophilic polymers and copolymers of the present invention. In the following examples, Disponil FES-77 is alkylpolyglycol ether sulfate, sodium salt, available from Henkel Corp., of Ambler, Pa. Airvol 523 is polyvinyl alcohol, available from Air Products and Chemicals, Inc., of Allentown, Pa.

EXAMPLE 1

Preparation of Poly 2-Hydroxyethyl Methacrylate in Ethanol

Recipe (1807 Gram Batch)

| Reactor Charge | |
|---|---|
| 2-Hydroxyethyl Methacrylate (Mitsubishi) | 540 grams |
| Ethanol | 1080 grams |
| Benzoyl peroxide | 2.7 grams |
| Cook-Off initiator #1 | |
| Ethanol | 60 grams |
| 2,2'-azobis(2,4-dimethylpentanenitrile)* | 1.4 grams |
| Cook-Off initiator #2 | |
| Ethanol | 60 grams |
| 2,2'-azobis(2,4-dimethylpentanenitrile)* | 1.4 grams |

-continued

| Cook-Off initiator #3 | |
| --- | --- |
| Ethanol | 60 grams |
| 2,2'-azobis(2,4-dimethylpentanenitrile)* | 1.4 grams |

*VAZO ®52 (2,2'-azobis(2,4-dimethylpentanenitrile) (Dupont; Wilmington, Delaware)

Procedure

1. The Reactor Charge was weighed out into a flask and poured into a reaction kettle with mixing, and was heated with an 80° C. jacket and a $N_2$ purge kettle.
2. The Cook-Off initiator #1 (Ethanol and VAZO®52) was weighed into a small beaker and mixed until the solids dissolved.
3. Three and one-half hours after the addition of the Reactor Charge, Cook-Off initiator #1 was added to the kettle.
4. The Cook-Off initiator #2 (Ethanol and VAZO®52) was weighed into a small beaker and mixed until the solids dissolved.
5. One hour after the addition of Cook-Off initiator #1, Cook-Off initiator #2 was added to the kettle.
6. The Cook-Off initiator #3 (Ethanol and VAZO®52) was weighed into a small beaker and mixed until the solids dissolved.
7. One hour after the addition of Cook-Off initiator #2, Cook-Off initiator #3 was added to the kettle.
8. One hour after the addition of Cook-Off initiator #3, the kettle contents were cooled and discharged.

The polymeric product synthesized in Example No. 1, above, exhibited the following properties:
Appearance: clear to light-yellow gel-free liquid
Solids: 30.5%
Viscosity: 8,700 cPs
Residual monomer: HEMA, 0.95%
Molecular weight: 483 K, PD 6.1

The appearance of the polymeric product in this example was determined utilizing a visual test looking at the clarity and color of the polymeric product. The presence of any gel in the polymeric product was determined by pouring a thin film of the product and visually inspecting for any particulate.

The percent solids in the polymeric product was measured by accurately weighing a small aluminum dish, then accurately weighing about 1 gram of wet polymer sample. The aluminum dish with the sample was dried under an infrared lamp for about 15 minutes. The aluminum dish with the dried sample was cooled and then accurately reweighed. The weight of the dried sample divided by the wet sample multiplied by 100 is the percent total solids in the sample.

The viscosity of the polymeric product was measured under ambient conditions (23–35° C.) with a Brookfield LV Viscometer using an appropriate spindle and speed for the measured viscosity. The viscosity units are centipoise, cPs.

The molecular weight of the polymeric product was measured using Gel Permeation Chromatography (GPC) in methanol with polyethylene glycol standards.

The protocols described hereinabove that were used to measure and evaluate the appearance, percent solids, viscosity and molecular weight of the polymeric product of Example No. 1 apply to all of the representative homopolymer and copolymer products produced according to the present invention, unless specifically indicated.

Example Nos. 2–6 are representative poly 2-hydroxyethyl methacrylates prepared in ethanol according to the present invention with 2-hydroxyethyl methacrylate monomers having alkylene glycol methacrylate impurities less than 3%, and wherein the alkylene glycol methacrylate impurities comprise ethylene glycol dimethacrylate impurities are between 0.05 and 0.1% by weight, and are compared to Comparative Example Nos. 7 and 8, which are poly 2-hydroxyethyl methacrylates prepared with 2-hydroxyethyl methacrylate monomers having alkylene glycol methacrylate impurities less than 3% and with ethylene glycol dimethacrylate greater than 0.15%. As Table I shows, substantially gel-free hydrophilic poly 2-hydroxyethyl methacrylates can be synthesized in ethanol. The poly 2-hydroxyethyl methacrylates can achieve molecular weights, Mw (weight average molecular weight), from about 176,000 to about 1,000,000, molecular weights, Mn (number average molecular weight), from about 59,000 to about 250,000, solids contents of about 30 weight percent, and a viscosity of about 1000 to about 151,000 cPs.

TABLE I

Synthesis of Poly 2-hydroxyethyl methacrylate in Ethanol

| Example No. | 2 | 3 | 4 | 5 | 6 | C7 | C8 |
| --- | --- | --- | --- | --- | --- | --- | --- |
| HEMA used[a] | Mitsubishi | Mitsubishi | Mitsubishi | Mitsubishi | Mitsubishi | Rohm & Haas | Rohm & Haas |
| Initiator | AIBN[b], 0.5% | BPo[c], 0.5% | BPo, 0.5% | BPo, 0.5% | BPo, 0.25% | AIBN, 0.5% | AIBN, 0.5% |
| Solids Content, % | 30 | 30.9 | 30.5 | 30.7 | 31.3 | gelled | gelled |
| Viscosity, cPs | 1090 | 7100 | 8700 | 15150 | 8200 | — | — |
| Mol. wt, Mw | 176,000 | 420,000 | 483,000 | 874,000 | 1,070,000 | — | — |
| Mol. wt, Mn | 59,200 | 68,000 | 78,700 | 187,000 | 252,000 | — | — |

[a] source of 2-hydroxyethyl methacrylate monomer
[b] AIBN (azobisisobutyronitrile)
[c] BPo(Benzoyl Peroxide)

Table I shows that the preparation of poly 2-hydroxyethyl methacrylate (poly HEMA) polymers, substantially in the absence of chain transfer agents, using the Mitsubishi HEMA monomer source having acceptable impurity levels provides high molecular weight gel free poly HEMA solution in alcohol. The molecular weight of the polymers can be varied by adjusting the type and amount of initiator used. The use of the AIBN initiator provides the lowest molecular weight polymer. In contrast, the poly HEMA prepared with Rohm & Haas HEMA monomer having 0.17% ethylene glycol dimethacrylate impurity levels, provided a gelled poly HEMA in alcohol, even when using AIBN as the initiator.

EXAMPLE 9

Preparation of Poly 2-Hydroxyethyl Methacrylate in Methanol

Recipe (982 Gram Batch)

| Reactor Charge | |
|---|---|
| 2-Hydroxyethyl Methacrylate (Mitsubishi) | 300 grams |
| Methanol | 700 grams |
| AIBN (2,2'-azobis(isobutyronitrile) | 1.5 grams |
| Cook-Off initiator | |
| Methanol | 15 grams |
| AIBN (2,2'-azobis(isobutyronitrile) | 0.75 grams |

Procedure

1. The Reactor Charge was weighed out into a flask and poured into a reaction kettle with mixing, and was heated with an 65° C. jacket and a $N_2$ purge kettle.
2. The Cook-Off initiator (Methanol and AIBN) was weighed into a small beaker and mixed until the solids dissolved.
3. Six hours after adding the Reactor Charge the Cook-Off initiator was added.
4. Four hours after adding the Cook Off initiator, the kettle contents were cooled and discharged.

The polymeric product synthesized in Example No. 9, above, exhibited the following properties:
Appearance: clear to light-yellow gel-free liquid
Solids: 36.7%
Viscosity: 39,000 cPs
Residual monomer: HEMA, 0.78%
Molecular weight: Mw=2,260 K, PD 4

The shear (min) and 180° peel adhesion properties of pressure sensitive adhesives prepared according to the present invention was evaluated. Table II, below, shows the shear properties and peel adhesion properties of pressure sensitive adhesives on substrates, such as stainless steel, high density polyethylene, and recycled cardboard. As Table II shows, pressure sensitive adhesives prepared by blending poly 2-hydroxyethyl methacrylate synthesized in methanol with 2-hydroxyethyl methacrylate monomers having alkylene glycol methacrylate impurities less than 3% by weight and with ethylene glycol dimethacrylate less than 0.1% and polyethylene glycol (PEG) have a 180° peel adhesion after twenty minutes of about 0.75 lb/in to about 4 lb/in on a stainless steel substrate, a 180° peel adhesion of about 0.2 lb/in to about 0.4 lb/in on a high density polyethylene substrate, and a 180° peel adhesion of about 1 lb/in to about 2 lb/in on a recycled cardboard substrate.

Table II also shows that pressure sensitive adhesives prepared by blending poly 2-hydroxyethyl methacrylate prepared with 2-hydroxyethyl methacrylate monomers having alkylene glycol methacrylate impurities less than 3% by weight and with ethylene glycol dimethacrylate impurity less than 0.1% with polyethylene glycol has a 180° peel adhesion after 24 hours of about 2.3 lb/in to about 4.3 lb/in on a stainless steel substrate, a 180° peel adhesion of about 0.3 lb/in to about 1 lb/in on a high density polyethylene substrate, and a 180° peel adhesion of about 2 lb/in to about 3.7 lb/in on a recycled cardboard substrate.

TABLE II

Poly 2-Hydroxyethyl Methacrylate synthesized in Methanol and Pressure Sensitive Adhesives

| Example No. | Resin/PEG | Coat Weight g/m² | Shear, min ¼ in², 500 g | 180° Peel, lb/in 20', SS | 180° Peel, lb/in 20', HDPE | 180° Peel, lb/in 20' RC | 180° Peel, lb/in 24 h, SS | 180° Peel, lb/in 24 h, HDPE | 180° Peel, lb/in 24 h RC |
|---|---|---|---|---|---|---|---|---|---|
| 10 | 1:1 | 38.1 | 2 c | 0.75 p | 0.2 p | 2.0 sl. c | 2.3 p | 0.3 p | 2.6 c |
| 11 | 1.2:0.8 | 33.6 | 98 c | 4.0 pt | 0.4 p | 1.7 sl. pt | 4.2 pt | 1.0 p | 3.7 pt |
| 12 | 1.3:0.7 | 30.7 | 143 c | 3.5 pt | 0.3 p | 1.1 sl. pt | 4.3 pt | 0.6 p | 2.0 pt |

SS—stainless steel;
HDPE—high density polyethylene;
RC—recycled cardboard
c—cohesive;
p—panel;
pt—paper tear;
sl.—slight Table II shows that polyHEMA polymers prepared in alcohol can be formulated with a plasticizer, such as polyethylene glycol (PEG) 400 (Carbowax; Union Carbide) to provide a pressure sensitive adhesive. The adhesive performance of the pressure sensitive adhesive can be varied by adjusting the amount of polyethylene glycol used in the preparation. A polyHEMA:PEG ratio in the range of about 1.5:0.5 to about 0.5:1.5 is used to prepare the pressure sensitive adhesive. Preferably, a polyHEMA:PEG ratio of about 1.2:0.8 is used to prepare the pressure sensitive adhesive.

Static shear measures the time required to remove a test sample from a substrate under a specific load. The test applies to the static force to remove an affixed pressure sensitive adhesive from a standard flat surface when the load acts parallel to the surface in a pure shearing action. In static shear testing, the samples were cut into 12×51 mm test strips. The test strips were applied to brightly annealed, highly polished stainless steel test panels having a typical size of about 50×75 mm, making a sample overlay of 12×12 mm with the test panel. The sample portion on the test panel was rolled on using a 2 kg, 5.45 pli 65 shore "A" rubber-faced roller, rolling back and forth one at a rate of 30 cm/min. After a dwell time of at least 15 minutes under standard laboratory testing conditions, the test panels with the test strips were placed at a 2° angle from the vertical, and a load of 500 g was attached to the end of the test strips. The time (in minutes) for the test sample to fail cohesively was measured by a timer.

To measure the peel adhesion, the adhesive was coated at an approximate coat weight of 25 g/m² (1.0 mil) onto a silicone coated release liner, and then laminated to a 2 mil Mylar™ facestock to form a laminate construction. The resulting laminate was die-cut into 25×204 mm sized test strips. The test strips were then applied to 50×152 mm brightly annealed, highly polishes stainless steel test panels in the lengthwise direction, and rolled down using a 2 kg 5.45 pli 65 shore "A" rubber faced roller. The roller was rolled back and forth once over the test strip at a rate of 30 cm/min. The samples were conditioned for either 15 minutes or 24 hours in a controlled environment testing room maintained at 20° C. and 50% relative humidity. After conditioning, the test strips were peeled away from the test panel in an Instron Universal Tester according to a modified version of the standard tape method Pressure-Sensitive Tape Council, PSTC-1. The force to remove the adhesive test strips from the test panel was measured in lbs/in. Glass panels and high density polyethylene panels were also used to measure peel adhesion.

Possible adhesion failure modes were: "panel failure," wherein the adhesive construction detached from the panel cleanly, without leaving any residue; "panel staining," wherein the adhesive construction detached cleanly, but left a faint stain or "shadow" on the panel; "cohesive failure," wherein the adhesive construction split apart, leaving residue on the test panel and the facestock; "facestock failure," wherein the adhesive completely detached from the facestock, and transferred to the test panel; and "mixed," wherein mixed failure modes were evident.

EXAMPLE 13

Preparation of HEMA/Methacrylic Acid Copolymer in Water

Recipe (1200 g Batch)

| Reactor Charge | |
|---|---|
| Deionized Water | 400.00 g |
| Initiator Charge | |
| Deionized Water | 100.00 g |
| Sodium Persulfate | 1.5 g |
| Monomer Feed | |
| 2-Hydroxyethyl Methacrylate | 270.0 g |
| Methacrylic Acid | 30.00 g |
| Deionized Water | 300.00 g |
| Ammonium Hydroxide (30%) | 12.3 g |
| Cook-Off Initiator #1 | |
| Deionized Water | 50.0 g |
| Sodium Persulfate | 0.75 g |
| Cook-Off Initiator #2 | |
| Deionized Water | 50.0 g |
| Sodium Persulfate | 0.75 g |

Procedure

1. The Reactor Charge was weighed out into a flask and poured into a reaction kettle.
2. The Reactor Charge was heated with an 80° C. jacket and a N₂ purge kettle.
3. The Monomer Feed (2-hydroxyethyl methacrylate, methacrylic acid, deionized water) was weighed into a feed jar, then ammonium hydroxide was added with mixing to adjust the pH to about 5.5.
4. The Initiator Charge (sodium persulfate and deionized water) was weighed out into a small beaker and mixed until the solid dissolved.
5. The Initiator Charge was poured into the reaction kettle with the heated and N₂₋ purged Reactor Charge.
6. After 10 minutes, the Monomer Feed was started for a 3-hour period (3.34 g/min), while maintaining an 80° C. jacket temperature.
7. The Cook-Off Initiator #1 (sodium persulfate and deionized water) was weighed into a small beaker and mixed until the solid dissolved.
8. One hour after the end of the Monomer Feed, the Cook-Off Initiator #1 was poured into the reaction kettle.
9. Cook-Off Initiator #2 (sodium persulfate and deionized water) was weighed into a small beaker and mixed until the solid dissolved.
10. One hour after adding Cook-Off #1, Cook-Off #2 was added.
11. One hour after adding Cook-Off #2, the kettle contents were cooled, then discharged into a quart jar.

The copolymer product synthesized in Example No. 13, above, exhibited the following properties:

Appearance: clear, light yellow gel-free liquid.
Solids: 25.9%
Viscosity: 33,000 cPs
pH: 5.5
Residual monomer: HEMA<0.02%, MAA 0.09%
Molecular weight: MW 392 K; polydispersity, the Mw/Mn (PD) 1.7

EXAMPLE 14

Preparation of HEMA/4-HBA Copolymer in Alcohol

Recipe (1003.75 g Batch)

| Reactor Charge | |
|---|---|
| 2-Hydroxyethyl Methacrylate (Mitsubishi) | 150 g |
| 4-Hydroxybutyl Acrylate (4-HBA) | 150 g |
| Ethanol | 600 g |
| Benzoyl Peroxide | 1.5 g |
| Cook-Off Initiator #1 | |
| Ethanol | 33.3 g |
| AIBN (2,2'-azobis[isobutyronitrile]) | 0.75 g |
| Cook-Off Initiator #2 | |
| Ethanol | 33.3 g |
| AIBN (2,2'-azobis[isobutyronitrile]) | 0.75 g |
| Cook-Off Initiator #3 | |
| Ethanol | 33.3 g |
| AIBN (2,2'-azobis[isobutyronitrile]) | 0.75 g |

Procedure

1. The Reactor Charge was weighed out into a flask and poured into a reaction kettle with mixing, heated with a 80° C. jacket, and $N_2$ purged.
2. The Cook-Off Initiator #1 (Ethanol and AIBN) was weighed into a small beaker and mixed until the solids dissolved.
3. Three and one-half hours after adding the Reactor Charge, the Cook-Off Initiator #1 was poured into the reaction kettle.
4. Cook-Off Initiator #2 (Ethanol and AIBN) was weighed into a small beaker and mixed until the solids dissolved.
5. One hour after adding Cook-Off #1, Cook-Off #2 was added.
6. Cook-Off Initiator #3 (Ethanol and AIBN) was weighed into a small beaker and mixed until the solids dissolved.
7. One hour after adding Cook-Off #2, Cook-Off #3 was added.
8. One hour after adding Cook-Off #3, the kettle contents were cooled, then discharged into a quart jar.

The copolymer product synthesized in Example No. 14, above, exhibited the following properties:
Appearance: clear, light yellow gel-free liquid.
Solids: 30.5%
Viscosity: 844 cPs
Residual monomer: HEMA<0.01%, 4-HBA 0.22%
Glass Transition Temperature, $T_g$, 9° C.
% Gel in water: 98%

The copolymer is swellable in water up to twice its weight.

Table III, below, shows the static shear and peel adhesion properties of pressure sensitive adhesives prepared by blending copolymers of poly 2-hydroxyethyl methacrylate and methacrylic acid (HEMA/MAA) with a polyalkylene glycol, such as polyethylene glycol (PEG). Example Nos. 13a and 13b are pressure sensitive adhesives prepared from blending HEMA/MAA copolymers and PEG. The HEMA polymers used in Example Nos. 13a and 13b were synthesized in water. Example No. 15 is a pressure sensitive adhesive prepared from blending HEMA/MAA copolymers and PEG. The HEMA/MAA copolymer used in Example No. 15 was synthesized in methanol. The HEMA polymer used in Example No. 16 was synthesized in methanol.

Static shear measures the time required to remove a test sample from a substrate under a specific load. The test applies to the static force to remove an affixed pressure sensitive adhesive from a standard flat surface when the load acts parallel to the surface in a pure shearing action. In static shear testing, the samples were cut into 12×51 mm test strips. The test strips were applied to brightly annealed, highly polished stainless steel test panels having a typical size of about 50×75 mm, making a sample overlay of 12×12 mm with the test panel. The sample portion on the test panel was rolled on using a 2 kg, 5.45 pli 65 shore "A" rubber-faced roller, rolling back and forth one at a rate of 30 cm/min. After a dwell time of at least 15 minutes under standard laboratory testing conditions, the test panels with the test strips were placed at a 2° angle from the vertical, and a load of 500 g was attached to the end of the test strips. The time (in minutes) for the test sample to fail cohesively was measured by a timer.

To measure the peel adhesion, the adhesive was coated at an approximate coat weight of 25 $g/m^2$ (1.0 mil) onto a silicone coated release liner, and then laminated to a 2 mil Mylar™ facestock to form a laminate construction. The resulting laminate was die-cut into 25×204 mm sized test strips. The test strips were then applied to 50×152 mm brightly annealed, highly polishes stainless steel test panels in the lengthwise direction, and rolled down using a 2 kg 5.45 pli 65 shore "A" rubber faced roller. The roller was rolled back and forth once over the test strip at a rate of 30 cm/min. The samples were conditioned for either 15 minutes or 24 hours in a controlled environment testing room maintained at 20° C. and 50% relative humidity. After conditioning, the test strips were peeled away from the test panel in an Instron Universal Tester according to a modified version of the standard tape method Pressure-Sensitive Tape Council, PSTC-1. The force to remove the adhesive test strips from the test panel was measured in lbs/in. Glass panels and high density polyethylene panels were also used to measure peel adhesion.

Possible adhesion failure modes were: "panel failure", wherein the adhesive construction detached from the panel cleanly, without leaving any residue; "panel staining", wherein the adhesive construction detached cleanly, but left a faint stain or "shadow" on the panel "cohesive failure", wherein the adhesive construction split apart, leaving residue on the test panel and the facestock; "facestock failure", wherein the adhesive completely detached from the facestock, and transferred to the test panel; and "mixed", wherein mixed failure modes were evident.

As Table III shows, pressure sensitive adhesives prepared with the HEMA/MAA copolymers of the present invention, exhibit a static shear of about 16 to about 170 minutes. Pressure sensitive adhesives prepared with the HEMA/MAA copolymers of the present invention exhibit a 180° peel adhesion on a stainless steel substrate of about 1.7 lb/in to about 3.4 lb/in after twenty minutes, and a 180° peel adhesion on a stainless steel substrate of about 2.7 lb/in to about 4 lb/in after 24 hours.

TABLE III

Pressure sensitive adhesives (PSA) prepared with copolymers of 2-hydroxyethylmethacrylate and methacrylic acid

| Example No. | Composition HEMA/MAA | Polymer:PEG | Shear, Min ¼ in², 500 g | 180° Peel, SS 20 min. | 180° Peel, SS 24 hours |
|---|---|---|---|---|---|
| 13a* | 90:10 | 1:1 | 169.5 c | 1.78 p | 2.78 pk |
| 13b* | 90:10 | 1:1 | 16.5 c | 3.41 p | 4.07 pt |

TABLE III-continued

Pressure sensitive adhesives (PSA) prepared with copolymers of 2-hydroxyethylmethacrylate and methacrylic acid

| Example No. | Composition HEMA/MAA | Polymer:PEG 1:1 | Shear, Min ¼ in², 500 g | 180° Peel, SS 20 min. | 180° Peel, SS 24 hours |
|---|---|---|---|---|---|
| 15** | 90:10 | 1:1 | 2.3 c | 0.88 p | 2.45 p |
| 16** | 100% HEMA | 1:1 | 1.8 c | 0.75 p | 2.26 p |

*HEMA/MMA copolymer synthesized in water
**HEMA/MMA copolymer synthesized in methanol
***poly HEMA synthesized in methanol Mode of failure
c = cohesive
p = panel
pk = fiber pick
pt = paper tear As Table III shows, poly HEMA/methacrylic acid copolymer prepared in water can also be formulated with a plasticizer, such as polyethylene glycol (PEG), to provide pressure sensitive adhesives. The adhesive performance of the pressure sensitive adhesives can be varied by adjusting the amount of PEG added. The results in Table III also show that the adhesive performance of the pressure sensitive adhesives comprising the poly HEMA/methacrylic acid copolymer prepared in water is comparable to the adhesive performance of pressure sensitive adhesives comprising poly HEMA prepared in alcohol, but without the need for the alcohol solvent.

As described hereinabove, the copolymer of 2-hydroxyethyl methacrylate and methacrylic acid prepared in water is also useful as abrasion resistant coatings for glass bottles. Tables IV and V, below, show the results of testing performed on glass beer bottles that were coated with the abrasion resistant coating comprising a copolymer of 2-hydroxyethyl methacrylate and methacrylic acid prepared in water according to the method of the present invention.

TABLE IV

Abrasion Resistant Coating comprising copolymer of polyHEMA/MMA (90/10)

| Example | Crosslinker[a] | Surfactant[b] | Wax[c] | Coating Clarity | Scratch Resistance | Water Resistance | Alkali Removal |
|---|---|---|---|---|---|---|---|
| 17 | 2.5% | 0 | 0 | 5 | 4 | 1 | 4 |
| 18 | 7.5% | 0 | 0 | 5 | 5 | 3 | 3 |
| 19 | 2.5% | 2% | 0 | 5 | 4 | 4 | 2.5 |
| 20 | 2.5% | 0 | 5% | 1 | 5 | 4 | 5 |
| 21 | 7.5% | 0 | 5% | 0 | 5 | 5 | 3 |
| 22 | 5% | 0 | 2.5% | 0 | 5 | 4 | 5 |
| 23 | 5% | 1% | 0 | 5 | 4 | 4 | 5 |

Rating: 0 = worst; 5 = best
a = ammonium dichromate
b = Dow Corning 193 Silicone surfactant
c = Michem 68725 wax

TABLE V

Abrasion Resistant Coating comprising copolymer of polyHEMA/MMA (90/10)

| Test | Example No. 24 Initial | Example No. 24 1 week, 70° C. | Example No. 24 3 week, 70° C. | Example No. 25 Initial | Example No. 25 1 week, 70° C. | Example No. 25 3 week, 70° C. |
|---|---|---|---|---|---|---|
| Auto Scratch | Good | Good | Good | OK | OK | OK |
| Scratch Resistance | 5H–6H | 6H | 6H | 5H | 6H | 6H |
| Water Resistance | | | | | | |
| Initial | OK | OK | OK | OK | OK | OK |
| 1 hour | 3H | H | H | 3H | 3H | 3H |
| Caustic Wash | Good | Good | Good | Good | Good | Good |

The auto scratch test is performed by contacting two coated bottles together to facilitate the scratching of the exterior surface of the bottles. The scratch resistance of the coated bottle is measured by using a H to 6H pencil to scratch the exterior surface of the coated bottle. The water resistance of the coated bottle is measured by soaking the coated bottles on deionized water for 48 hours at room temperature. The exterior surface of the soaked bottles are then scratched with an individual's fingernail immediately when taken from the water, or scratched with a H to 6H pencil after one hour of drying at room temperature. The caustic wash test measures the removability of the copolymer coating by alkali treatment. The copolymer coated bottles are placed into a caustic solution, such as 1% sodium hydroxide for 15 minutes at room temperature with magnetic stir bar agitation, followed by rinsing with water.

As Tables IV and V show, that the copolymers of 2-hydroxyethyl methacrylate and methacrylic acid are useful as abrasion resistant coatings for glass bottles. The copolymer coatings prevent scratching of the exterior surface of glass beer bottles, even after soaking in deionized water. In addition, the copolymer coating is easily removed from the exterior surface of the glass bottles by treatment with an alkali solution.

Examples 26–33 are copolymers of 2-hydroxyethyl methacrylate and 4-hydroxybutyl acrylate having varying ratios of 2-hydroxyethyl methacrylate to 4-hydroxybutyl acrylate, and which were prepared substantially in accordance with the procedure of Example 13. The moisture vapor transmission rate (MVTR) and mechanical properties, including % strain at peak, stress at peak, stress at 2% elongation, and Young's modulus, of the copolymers of 2-hydroxyethyl methacrylate and 4-hydroxybutyl acrylate were tested. The results of the evaluation of the moisture vapor transmission rate and mechanical properties are shown in Table VIa.

Moisture Vapor Transmission Rate (MVTR) is a measure to describe the ability of a film to allow moisture vapor to pass through over specific period of time and under a controlled temperature and atmospheric pressure. With particular reference to skin applications, such as protective films and coatings, the MVTR is a measure of a film's ability to move vapor away from the skin of a patient. The MVTR was measured according to INDA Standard IST 70.4 (99). The samples were coated on a 1 mil thick MVTR film commercially available from Mylan Technologies (St. Albans, Vt.; U.S.A.) under the designation Medifilm 390 at a coat weight of 25 to 35 g/m².

TABLE VIa

| Example | Ratio HEMA/4HBA | $T_g$ | % Strain at peak | Stress at peak (psi) | Stress at 2% yield (psi) | Young's Modulus (psi) | MVTR g/m²/day |
|---|---|---|---|---|---|---|---|
| 26 | 50/50 | 5° C. | too soft | — | — | — | 3440 |
| 27 | 60/40 | 20° C. | 266 | 1035 | 216 | 5,585 | 2880 |
| 28 | 67/33 | 26° C. | 166 | 1618 | 910 | 38,211 | 2590 |
| 29 | 70/30 | 29° C. | 6.7 | 2142 | 1583 | 59,657 | 1980 |
| 30 | 75/25 | 36° C. | 4.9 | 4026 | 2520 | 145,714 | 1920 |
| 31 | 80/20 | 54° C. | too brittle | — | — | — | 2650 |
| 32 | 100/0 | 70° C. | too brittle | — | — | — | 2156 |
| 33 | 0/100 | −30° C. | — | — | — | — | 4330 |

Coatings of the copolymers of 2-hydroxyethyl methacrylate and 4-hydroxybutyl acrylate were also evaluated for abrasion resistance of the coating to cloth to simulate the abrasion resistance of the copolymer to clothing.

The abrasion resistance of the copolymers of 2-hydroxyethyl methacrylate and 4-hydroxybutyl acrylate of Examples 26–32, prepared in accordance with the methods of the present invention, were evaluated for abrasion resistance by a modified Southerland Rub Test (ASTM D1331-89). The results of the abrasion resistance studies are set forth in Table VIb.

TABLE VIb

| | Ratio HEMA/ | Southerland Rub Test 4 lbs, 200 strokes | |
|---|---|---|---|
| Example | 4HBA | Coating against coating | Coating against cloth |
| 26 | 50/50 | failed, too tacky | slight abrasion |
| 27 | 60/40 | few scratches | slight abrasion |
| 28 | 67/33 | scratches & abrasion | slight abrasion |
| 29 | 70/30 | scratches & abrasion | no abrasion |
| 30 | 75/25 | scratches & abrasion | slight abrasion |
| 31 | 80/20 | scratches & abrasion | slight abrasion |
| 32 | 100/0 | scratches & abrasion | slight abrasion |

As shown in Table VIb, above, coatings comprising a copolymer of 2-hydroxyethyl methacrylate and 4-hydroxybutyl acrylate, prepared in accordance with the methods of the present invention, exhibit only slight abrasion when rubbed against cloth and, therefore, appear useful as skin coatings or barriers.

The surface tension of copolymers of 2-hydroxyethyl methacrylate and 4-hydroxybutyl acrylate and copolymers of 2-hydroxyethyl methacrylate and 4-hydroxybutyl acrylate containing 0.1%, 0.2%, 0.5% or 1% of a silicone surfactant were determined and compared to the surface tensions of water and ethanol. The results of the surface tension testing is set forth in Table VIc.

TABLE VIc

| | Surface Tension | |
|---|---|---|
| Example No. | | Surface Tension dynes/cm |
| 33 | water | 74.1 |
| 34 | ethanol | 24.1 |
| 35 | copolymer of 2-HEMA/4-HBA | 30.4 |

TABLE VIc-continued

| | Surface Tension | |
|---|---|---|
| Example No. | | Surface Tension dynes/cm |
| 36a | copolymer of 2-HEMA/4-HBA 0.1% surfactant | 26 |
| 36b | copolymer of 2-HEMA/4-HBA 0.2% surfactant | 24.1 |

TABLE VIc-continued

Surface Tension

| Example No. | | Surface Tension dynes/cm |
|---|---|---|
| 36c | copolymer of 2-HEMA/4-HBA 0.5% surfactant | 23.9 |
| 36d | copolymer of 2-HEMA/4-HBA 1% surfactant | 23.3 |

As shown in Table VIc, above, the copolymer of 2-hydroxyethyl methacrylate and 4-hydrobutyl acrylate has a surface tension of about 30 dynes/cm. The addition, of at least 0.1% of a silicon surfactant to the copolymer of 2-hydroxyethyl methacrylate and 4-hydrobutyl acrylate reduces the surface tension of the copolymer to 26 dynes/cm or lower.

In general, to "wet" a surface, it is necessary to use a material that has a surface tension that is similar to and, preferably, lower than the surface tension of the surface to be "wetted." Human skin has a surface tension of about 27 dynes/cm. To "wet" the surface of human skin, it is necessary to utilize a material that possesses a surface tension that is similar than the surface tension of human skin. Using a copolymer 2-hydroxyethyl methacrylate and 4-hydrobutyl acrylate, it is possible to provide a continuous copolymer coatings for the surface of human skin without experiencing bleeding or gaps therein.

EXAMPLE 37

Preparation of Copolymer of 2-hydroxyethyl Methacrylate and 4-hydroxybutyl Acrylate in an Ethanol/Water Solution Recipe (1002.4 Gram Batch)

| Reactor Charge | |
|---|---|
| 2-Hydroxyethyl Methacrylate (Mitsubishi) | 200 grams |
| 4-Hydroxybutyl acrylate | 100 grams |
| Ethanol | 400 grams |
| Deionized Water | 260 grams |
| Initiator Charge | |
| Deionized Water | 10 grams |
| Sodium Persulfate (0.5%) | 1.5 grams |
| Cook-Off Initiator #1 | |
| Deionized Water | 10 grams |
| Sodium Persulfate | 0.3 grams |
| Cook off Initiator #2 | |
| Deionized Water | 10 grams |
| Sodium Persulfate | 0.3 grams |
| Cook off Initiator #3 | |
| Deionized Water | 10 grams |
| Sodium Metabisulfite | 0.3 grams |
| Total | 1002.4 grams |

Procedure

1. The Reactor Charge was weighed out into a flask and poured into a reaction kettle with mixing, and was heated with an 80° C. jacket and a $N_2$ purge kettle.
2. The Cook-Off initiator #1 was weighed into a small beaker and mixed until the solids dissolved.
3. About three hours after the addition of the Reactor Charge, Cook-Off initiator #1 was added to the kettle.
4. The Cook-Off initiator #2 was weighed into a small beaker and mixed until the solids dissolved.
5. About one hour after the addition of Cook-Off initiator #1, Cook-Off initiator #2 was added to the kettle.
6. The Cook-Off initiator #3 was weighed into a small beaker and mixed until the solids dissolved.
7. One hour after the addition of Cook-Off initiator #2, Cook-Off initiator #3 was added to the kettle.
8. About one-half hour after the addition of Cook-Off initiator #3, the kettle contents were cooled and discharged.

The polymeric product synthesized in Example No. 14, above, exhibited the following properties:

Appearance: clear to light-yellow gel-free liquid
Solids: 30%
Residual monomers

| 2-Hydroxyethyl Methacrylate | 0.02% |
|---|---|
| 4-Hydroxybutyl Acrylate | <0.01% |

Pressure sensitive adhesives were prepared comprising either the homopolymer of poly-4-hydoxybutyl acrylate prepared in an alcohol/water mixture, a homopolymer of poly-2-hydroxyethyl methacrylate prepared in an alcohol/water mixture, or a copolymer of poly-2-hydroxyethyl methacrylate and poly-4-hydroxybutyl acrylate prepared in an alcohol/water mixture as described above.

Each of the pressure sensitive adhesive compositions were evaluated for static shear properties and peel adhesion properties on stainless steel substrates and polymeric substrates, such as high density polyethylene (HDPE). The results of the tests are shown in Table VIIa.

TABLE VIIa

| Ex. | HEMA/ 4-HBA | Polymer/ PEG | Shear, min. ¼ in². 500 g | 180° Peel, lb/in 15 min., SS | 180° Peel, lb/in 15 min., HDPE | 180° Peel, lb/in 24 hr., SS | 180° Peel, lb/in 24 hr, HDPE |
|---|---|---|---|---|---|---|---|
| 38 | 0/100 | 100/0 | 4,260 (+) | 3.423 (ft) | 0.695 (cl) | 4,187 (ft) | 2.165 (cl) |
| 39 | 50/50 | 75/25 | 63.4 (sp) | 3.391 (cl) | 1.116 (cl) | 3.761 (cl) | 0.937 (cl) |
| 40 | 100/0 | 60/40 | 223.4 (sp) | 2.973 (cl) | 0.466 (cl) | 3.042 (ft) | 0.865 (cl) |

The tack of the pressure sensitive adhesive was determined by a modified spherical probe adhesion test that involves recording and analyzing the entire stress-strain behavior of a pressure sensitive adhesive during bonding and debonding of the probe. The test apparatus consists of a stainless steel spherical probe connected to a force transducer. The force transducer measures the force acting upon the spherical probe. The probe is moved up and down by a rotating screw driven by a stepping motor. A pressure sensitive adhesive sample is bonded adhesive side up to the test platform with a double-sided tape. During bonding of the probe to the pressure sensitive adhesive, the probe moves down and compresses the adhesive to a pre-determined force (i.e.—compression force). During the debonding process, the probe ascends and separates from the pressure sensitive adhesive sample and a pre-determined test speed. As the probe ascends, the adhesive sample becomes elongated and exerts a tensile force on the transducer. As the adhesive is further elongated, the stress increases in the adhesive until it reaches the interfacial strength between the probe and the adhesive, at which point the probe separates from the adhesive sample. The debonding strength of the adhesive sample is measured by the magnitude of the force and duration time of the probe. The results of the tests are shown in Table VIb, below. For a detailed description for the measurement of the tack of pressure sensitive adhesives, see "Avery Adhesive Test, AAT", *Adhesives Age*, Vol. 10, No. 10, pp.18–23 (1997).

TABLE VIIb

| Ex. | HEMA/ 4-HBA Copolymer | Polymer/PEG | Force (N) | Energy Nm × 10$^{-5}$ |
|---|---|---|---|---|
| 38 | 0/100 | 100/0 | 0.977 | 0.144 |
| 39 | 50/50 | 75/25 | 1.359 | 0.079 |
| 40 | 100/0 | 60/40 | 1.089 | 0.024 |

As described hereinabove, the copolymers of 2-hydroxyethyl methacrylate and 4-hydrobutyl acrylate prepared according to the method of the present invention possess the capability to undergo self crosslinking with thermal treatment. Examples 41–44 are copolymers of 2-hydroxyethyl methacrylate and 4-hydroxybutyl acrylate prepared in ethanol, where the ratio of HEMA to 4-HBA is 67/33. Examples 46–48 are copolymers of 2-hydroxyethyl methacrylate and 4-hydroxybutyl acrylate prepared in a solution of ethanol and water, where the ratio of HEMA to 4-HBA is 60/40. Examples 50–52 are copolymers of 2-hydroxyethyl methacrylate and 4-hydroxybutyl acrylate prepared in a solution of ethanol and water, where the ratio of HEMA to 4-HBA is 50/50. All of the copolymer products were cast into films and the films were dried at 70° C. for 15 minutes. Thereafter, the percent (%) insoluble, percent (%) strain at break, and Young's modulus were tested for each copolymer product. Comparative Examples 41, 45, and 49 were dried at 70° C. for 15 minutes, but were not cured further.

The strain of a particular body refers to the change in the dimensions of that body in response to an applied force. The Young's modulus of a particular body refers to the ratio between the compressive stress and the elongation of a solid body. The % strain at break and the Young's modulus of the copolymers of 2-hydroxyethyl methacrylate and 4-hydroxybutyl acrylate were determined according to ASTM Standard D 638M (93) using dumbell-shaped test samples.

The results of the tensile testing and percent insoluble in methanol of samples are reported in Table VIII below.

TABLE VIII

| Ex. | HEMA/ 4-HBA ratio | Curing conditions | Tensile Testing | | % insoluble in MeOH |
|---|---|---|---|---|---|
| | | | % Strain at break | Young's Modulus, psi | |
| C41 | 67/33 | — | 253.5 | 17227 | 33.8 |
| 42 | 67/33 | 100° C., 5 min | 195.3 | 23489 | 56.8 |
| 43 | 67/33 | 125° C., 5 min | 184.2 | 31192 | 67.1 |
| 44 | 67/33 | 150° C., 5 min | 150 | 59470 | 89.7 |
| C45 | 60/40 | — | 399.4 | 500.2 | 59.3 |
| 46 | 60/40 | 100° C., 5 min | 383.4 | 1499.6 | 60.6 |
| 47 | 60/40 | 125° C., 5 min | 342.7 | 3917.4 | 59.1 |
| 48 | 60/40 | 150° C., 5 min | 328.8 | 5514.1 | 75.3 |
| C49 | 50/50 | — | 564.9 | 89 | 53.1 |
| 50 | 50/50 | 100° C., 5 min | 524.9 | 193.5 | 61.6 |
| 51 | 50/50 | 125° C., 5 min | 495.3 | 148.6 | 72 |
| 52 | 50/50 | 150° C., 5 min | 356.8 | 449.3 | 83 |

As shown in Table VIII, the copolymers of HEMA and 4-HBA can be self-crosslinked with thermal treatment only. The cured copolymers exhibit lower strains at break and higher moduli as compared to the uncured copolymers. The ability to self crosslink is especially beneficial where the copolymeric product is intended to be utilized for skin applications and, therefore, it would be advantageous to avoid the use crosslinking agents that may be toxic.

EXAMPLE 53

Preparation of Copolymer of 2-hydroxyethyl Methacrylate and 4-hydroxybutyl Acrylate in an Ethanol/Water Solution Recipe

| Reactor Charge | |
|---|---|
| 2-Hydroxyethyl Methacrylate (Mitsubishi) | 16.64 Kg |
| 4-Hydroxybutyl acrylate | 8.32 Kg |
| Ethanol | 24.12 Kg |
| Deionized Water | 24.12 Kg |
| Initiator Charge | |
| Deionized Water | 0.41 Kg |
| Sodium Persulfate | 0.13 Kg |
| Cook-Off Initiator #1 | |
| Deionized Water | 0.2 Kg |
| Ethanol | 0.2 Kg |
| Sodium Persulfate | 0.025 Kg |
| Cook off Initiator #2 | |
| Deionized Water | 0.2 Kg |
| Ethanol | 0.2 Kg |
| Sodium Persulfate | 0.025 Kg |
| Cook off Initiator #3 | |
| Deionized Water | 0.2 Kg |
| Ethanol | 0.2 Kg |
| Sodium Metabisulfite | 0.025 Kg |
| Total | 75.4 Kg |

Procedure

1. Begin heating reactor with a 83° C. jacket and with a $N_2$ purge.
2. The Reactor Charge was weighed out into a weight tank and transferred to the reactor with mixing.
3. When Reactor Charge reaches a temperature of about 76° C., the Initiator Charge was added to the reactor.
4. With reaction temperature going to 85° C. Start hold period. Hold for three hours (reaction to 77.5° C.).
5. The Cook-Off initiator #1 was weighed into a beaker, and mixed until the solids dissolved.
6. About three hours after the addition of the Reactor Charge, Cook-Off initiator #1 was added to the reactor.
7. The Cook-Off initiator #2 was weighed into a beaker and mixed until the solids dissolved.
8. About one hour after the addition of Cook-Off initiator #1, Cook-Off initiator #2 was added to the reactor.
9. The Cook-Off initiator #3 was weighed into a beaker and mixed until the solids dissolved.
10. One hour after the addition of Cook-Off initiator #2, Cook-Off initiator #3 was added to the reactor.
11. About one hour after the addition of Cook-Off initiator #3, the reactor contents were cooled and the leaching process started.

Samples of the polymerization product were taken from the reactor every hour throughout the reaction to evaluate the conversion of the monomers to the copolymeric product and the residual monomers remaining in the reactor. The amount of the residual monomers remaining in the reactor after each hour of the reaction are shown in Table IX below.

TABLE IX

| Hour | Residual Monomer | |
|---|---|---|
| | HEMA | 4-HBA |
| 1 | 0.25% | 0.45% |
| 2 | 82 ppm | 700 ppm |
| 3 | 85 ppm | 360 ppm |
| 4 | 90 ppm | 120 ppm |
| 5 | 80 ppm | 50 ppm |
| 6 | 50 ppm | <10 ppm |

As is shown in Table IX, one hour after the addition of Cook-Off Initiator #3, the reaction mixture only contains 55 ppm HEMA residual monomer and <10 ppm 4-HBA residual monomer. These results demonstrate that the copolymerization of HEMA and 4-HBA in a solution of alcohol and water results in a very efficient conversion of monomer into copolymer product with a very low occurrence of residual monomer in the final copolymeric product.

It should be noted that a leaching process may also be utilized to remove any residual monomers and initiators, thus further purifying the copolymeric product of HEMA and 4-HBA. A suitable leaching process for use with the polymer prepared according the present invention is set forth below.

Leaching Process

First Leach

| | |
|---|---|
| Water to precipitate polymer | 94.1 Kg |
| Decant off effluent | 93.3 Kg |
| Ethanol to redissolve | 7.5 Kg |

Residual monomer remaining after first leach:

| | |
|---|---|
| HEMA | <50 ppm |
| 4-HBA | <10 ppm |

Second Leach

| | |
|---|---|
| Water to precipitate polymer | 74.8 Kg |
| Decant off effluent | 92.9 Kg |
| Ethanol to redissolve | 7.5 Kg |

Residual monomer remaining after second leach:

| | |
|---|---|
| HEMA | <50 ppm |
| 4-HBA | <10 ppm |

Third Leach

| | |
|---|---|
| Water to precipitate polymer | 74.8 Kg |
| Decant off effluent | 81.5 Kg |
| Ethanol to redissolve | 9.4 Kg |

Residual monomer remaining after first leach:

| | |
|---|---|
| HEMA | <50 ppm |
| 4-HBA | <10 ppm |

The leached polymeric product synthesized in Example No. 53, above, exhibited the following properties:

| | |
|---|---|
| Viscosity, cPs | 660 |
| % Solids content | 23.6% |
| % Ethanol | 23.5% |
| % Water | 52.9% |
| Residual monomers | |
| 2-Hydroxyethyl Methacrylate | <50 ppm |
| 4-Hydroxybutyl Acrylate | <10 ppm |

Extensive leaching processes have been conventionally used in the art to remove residual monomers, initiators, and other reactants from the final polymeric products require the use of elevated temperatures, reduced pressures, centrifugation and/or multiple washes. To the contrary, all of the polymeric products prepared by the methods of the present invention have very low levels of residual monomers and other reactants remaining after the polymerization process. However, if further purification is desired, the polymeric products may be subjected to a leaching process with water and ambient temperature and pressure.

EXAMPLE 54

Preparation of Clear Core/Shell Polymer Emulsion

| | grams |
|---|---|
| Reactor Charge | |
| Deionized Water | 175.7 |
| Airvol 523 (15% solution) | 65.0 |
| Disponyl FES 77 (32%) | 14.3 |
| NaFeEDTA | 0.02 |
| Tert-Butyl Hydroperoxide | 0.3 |
| Activator Feed | |
| Deionized Water | 150.9 |
| Sodium Formaldehyde Sulfoxylate | 1.1 |
| Core Feeds | |

-continued

|  | grams |
|---|---|
| Water Soluble Monomer Feed | |
| Deionized Water | 338.0 |
| 2-Hydroxyethyl Methacrylate | 160.0 |
| n-Vinyl Pyrrolidone | 100.0 |
| tert-Butyl Hydroperoxide | 2.0 |
| PreEmulsion Feed | |
| Deionized Water | 105.2 |
| Airvol 523 (15% solution) | 32.5 |
| Disponyl FES 77 (32%) | 14.3 |
| Butyl Acrylate | 100.0 |
| Diethylaminoethyl Methacrylate | 40.0 |
| Shell Feed | |
| 2-Hydroxyethyl Methacrylate | 50.0 |
| n-Vinyl Pyrrolidone | 31.3 |
| Butyl Acrylate | 40.0 |
| Methacrylic Acid | 3.8 |
| Tert-Butyl Hydroperoxide | 0.1 |
| Ammonium Hydroxide (28%) | 1.9 |
| Cook Off | |
| Tert-Butyl Hydroperoxide | 0.5 |
| Total | 1426.8 |

Procedure

1. Heated Reactor Charge to 53–55° C. with a 55° C. jacket. Mixed at 125 RPM and used a nitrogen purge.
2. Added 15 g of PreEmulsion Feed to Reactor.
3. Waited 5 minutes, then added 7 g of Activator solution.
4. Waited 5 minutes, then began 3 Feeds:
   Monomer: 600 g/180 min. (=3.33 g/min)
   PreEmulsion: 277 g/180 min. (=1.54 g/min)
   Activator: 145 ml/270 min. (=0.54 ml/min)
5. 20 minutes after Monomer & PreEmulsion feeds ended, began shell feed: 127 g/60 (=2.11 g/min).
6. Continued Activator feed for 30 minutes after Shell feed ended. Then stopped Activator Feed and added Cook Off.
7. Cooked for 30 minutes, then cool and discharged.

The resulting polymer had the following properties:

| Solids | 32.5% |
|---|---|
| Viscosity | 111 cPs |

EXAMPLE 55

Preparation of Clear Core/Shell Polymer Emulsion

|  | grams |
|---|---|
| Reactor Charge | |
| Deionized Water | 143.0 |
| Airvol 523 (10% solution) | 95.7 |
| Disponyl FES 77 (32%) | 14.3 |

-continued

|  | grams |
|---|---|
| NaFeEDTA | 0.02 |
| tert-Butyl Hydroperoxide | 0.3 |
| Activator Feed | |
| Deionized Water | 135.9 |
| Sodium Formaldehyde Sulfoxylate | 1.1 |
| Core Feeds | |
| Monomer Feed | |
| Deionized Water | 83.0 |
| 2-Hydroxyethyl Methacrylate | 80.0 |
| n-Vinyl Pyrrolidone | 30.0 |
| tert-Butyl Hydroperoxide | 2.0 |
| PreEmulsion Feed | |
| Deionized Water | 36.9 |
| Airvol 523 (10% solution) | 48.8 |
| Disponyl FES 77 (32%) | 14.3 |
| Butyl Acrylate | 63.5 |
| Methyl Acrylate | 9.5 |
| Methyl Methacrylate | 9.5 |
| Diethylaminoethyl Methacrylate | 25.0 |
| Trifluoroethyl Methacrylate | 2.5 |
| Shell Feed-Monomer | |
| 2-Hydroxyethyl Methacrylate | 36.3 |
| n-vinyl Pyrrolidone | 9.9 |
| Dimethylaminoethyl Acrylate-Methyl Chloride Quaternary | 7.1 |
| Methacrylic Acid | 9.9 |
| Methyl Acrylate | 11.0 |
| Methyl Methacrylate | 33.3 |
| Trifluoroethyl Methacrylate | 2.5 |
| tert-Butyl Hydroperoxide | 0.2 |
| Shell Feed-Ammonia | |
| Deionized Water | 107.1 |
| Ammonium Hydroxide (30%) | 5.0 |
| Cook Off | |
| Tert-Butyl Hydroperoxide | 0.5 |
| Total | 1018.1 |

Procedure

1. Heated Reactor Charge to 53–55° C. with a 55° C. jacket. Mixed at 125 RPM and used a nitrogen purge.
2. Added 15 g of PreEmulsion Feed to Reactor.
3. Waited 5 minutes, then added 7 g of Activator solution.
4. Waited 5 minutes, then began 3 Feeds:
   Monomer: 195 g/100 min. (=1.95 g/min)
   PreEmulsion: 195 g/100 min. (=1.95 g/min)
   Activator: 130 ml/240min. (=0.54 ml/min)
5. 20 minutes after Monomer and PreEmulsion feeds ended, began Shell Monomer feed: 110 g/60 min (=1.83 g/min) and began Shell Ammonia feed: 110 g/60 min (=1.83 g/min).
6. Continued Activator feed for 30 minutes after Shell feed ended. Then stopped Activator Feed and added Cook Off.
7. Cooked for 30 minutes, then cooled and discharged.

The resulting polymer had the following properties:

| Solids | 33.9% |
|---|---|
| Viscosity | 300 cPs |

EXAMPLE 56

Preparation of Copolymer by Alkyl Acrylate Emulsion/Water-Soluble Feeds Method

| Reactor Charge | |
|---|---|
| Deionized Water | 175.7 g |
| Airvol 523 (15% solution) | 65 g |
| Disponyl FES 77 (32%) | 14.3 g |
| NaFeEDTA | 0.02 g |
| tert-Butyl Hydroperoxide | 0.3 g |
| Monomer Feed | |
| Deionized Water | 338 g |
| 2-Hydroxyethyl Methacrylate | 160 g |
| n-Vinyl Pyrrolidone | 100 g |
| tert-Butyl Hydroperoxide | 2 g |
| PreEmulsion Feed | |
| Deionized Water | 105.2 g |
| Airvol 523 (15% solution) | 32.5 g |
| Disponyl FES 77 (32%) | 14.3 g |
| Butyl Acrylate | 100 g |
| Diethylaminoethyl Methacrylate | 40 g |
| Activator Feed | |
| Deioinized Water | 135.9 g |
| Sodium Formaldehyde Sulfoxylate | 1.1 g |
| Cook Off | |
| tert-Butyl Hydroperoxide | 0.5 g |
| Total | 1284.8 g |

Procedure

1. The reactor charge was heated to about 53–55° C. with a 55° C. jacket. Mixed at 125 RPM and used a nitrogen purge.
2. 15 g of PreEmulsion Feed was added to the reactor.
3. After 5 minutes, 7 g of Activator solution was added to the reactor.
4. After 5 minutes, begin to add three feeds:
   Monomer Feed 600 g/210 minutes (2.86 g/min)
   PreEmulsion Feed 277 g/210 minutes (1.32 g/min)
   Activator Feed 130 ml/240 minutes (0.54 ml/min)
5. Continue to add Activator Feed for 30 minutes after Monomer and PreEmulsion feeds end.
6. Stop adding Activator Feed and add Cook Off.
7. Cook for 30 minutes, then cool and discharge.

The resulting polymer had the following properties:

| Solids | 31.8% |
|---|---|
| Viscosity | 78 cPs |

Example No. 56 is a poly 2-hydroxyethylmethacrylate copolymer prepared in water emulsions according to the Alkyl Acrylate emulsion/water-soluble feeds method of the present invention. Example Nos. 57–59 are poly 2-hydroxyethylmethacrylate copolymers prepared in water emulsions according to the core/shell method of the present invention. Example Nos. 56–59 were evaluated as coatings for ink jet applications. Example No. 57 of Table X is the copolymer prepared according to Example No 54 described hereinabove. Example No. 59 of Table X is the copolymer prepared according to Example No. 55 described hereinabove. The copolymer coatings of the present invention were compared to Comparative Example Nos. 60–63.

The poly 2-hydroxyethyl methacrylate copolymer emulsions of Example Nos. 56–59 were coated onto Mylar™ clear polyester films (Dupont; Wilmington, Del.) having a thickness of 4 millimeters (mm) at a coat weight of about 20 to about 25 g/m². The coating was dried at 70° C. for about 15 minutes. The clear polyester film having the dried coating thereon was cut into 8½"×11" sheets for testing.

Comparative Example Nos. 60 and 61 are premium inkjet transparency films for overhead projectors that are commercially available from Hewlett Packard Company (Palo Alto, Calif.) and Minnesota Mining and Manufacturing Company (3M; Saint Paul, Minn.). Comparative Example No. 62 is a premium glossy paper for inkjet printer that comprises a clear polyester film with an opaque coating thereon that is commercially available from Hewlett Packard Company. Comparative Example No. 63 is a plain clear polyester film without a coating.

The poly 2-hydroxyethyl methacrylate copolymer coatings were evaluated for clarity, image quality, drying time, ink density, and water resistance. Each property was evaluated on a scale from 1 to 5, with 1 being the lowest possible rating and 5 being the highest possible rating.

The clarity was evaluated by a visual inspection of the coated film before printing for haziness and particulate matter.

The image quality was evaluated by a visual inspection performed after printing. The visual inspection was performed using a 10× magnifying glass, looking for indications of "feathering", which represents fuzzy edges of images, "mud cracking", and "cascading", which is a measure of the coverage in the fill areas.

The ink density was measured after printing using a densitometer (Tobias IQ 150 portable reflection densitometer) in a 100% fill area of each color. The units for ink density are density units.

The drying time of the ink on the coated films was measured immediately after the printing was completed. The dry time was tested by testing the smearing of the various colors on the film every 30 seconds until the ink dried. The time indicated in Table X is the time for the last color to smear. Although the testing was performed on film, it is important to note that the acrylic emulsion ink jet receptive coatings of the present invention are also useful as glossy coatings on paper that is to be utilized for ink jet printing.

The water resistance was tested about 20 minutes after the printing was completed. Each example was held at an angle while about 5 ml of water was dripped onto the 100% fill area of each color. The results of the above described tests are set forth in Table X, below.

TABLE X

Evaluation of 2-hydroxyethyl methacrylate copolymers as ink jet coatings

| Example No. | 56 | 57 | 58 | 59 | C60 | C61 | C62 | C63 |
|---|---|---|---|---|---|---|---|---|
| Coat Weight | 25 | 19 | 22 | 21 | — | — | — | — |
| Clarity* | 4 | 4 | 4.5 | 3 | 1 | 2 | opaque | 5 |
| Image Quality* | 3 | 3 | 3.5 | 3.5 | 3 | 3 | 4 | 1 |
| Ink Density | | | | | | | | |
| Black | 0.82 | 0.88 | 1.42 | 1.42 | 1.82 | 2.04 | 1.76 | 0.34 |
| Cyan | 0.74 | 0.76 | 0.87 | 0.85 | 0.70 | 0.72 | 0.71 | 0.96 |
| Magenta | 1.74 | 1.82 | 1.88 | 1.82 | 1.45 | 1.59 | 1.33 | 1.17 |
| Yellow | 1.2 | 1.19 | 1.25 | 1.25 | 1.25 | 1.19 | 1.29 | 0.21 |
| Drying Time, minutes | 3 | 3 | 2 | 2 | 1.5 | 1.5 | 1 | 1200 |
| Water Resistance* | 2 | 2.5 | 4 | 4 | 2 | 1 | 3 | 1 |

*1(worst)–5 (best)

Comparative Example Nos. C60 and C61 are commercially available ink jet transparency films having a grainy appearance. Comparative Example No. C62 is a commercially available ink jet paper that is a pigmented film. Comparative Example No. C63 is a commercially available plain polyester film without a coating, which does not absorb or dry ink. As one can see from Table X, the hydrophilic emulsions of the present invention are particularly useful as clear coatings for ink jet recording films. The clear coatings provide excellent performance without the need for the addition of pigments and, therefore, avoids the grainy/hazy appearance associated with the commercially available films.

EXAMPLE 64

Preparation of Poly(HEMA) Powder

Recipe (100 Gram Batch)

| The following were added to a reaction vessel with stirring: | |
|---|---|
| Deionized Water | 60.0 g |
| 2-Hydroxyethyl Methacrylate (Mitsubishi) | 30.0 g |
| After 15 minutes of a nitrogen purge, the following was added: | |
| Sodium Metabisulfite (10% solution) | 5.0 g |
| After an additional 15 minutes of a nitrogen purge, the following was added: | |
| Sodium Metabisulfite (10% solution) | 5.0 g |

The reaction was held at ambient temperature for an additional 4 hours with a constant nitrogen flow. The product was chopped and leached overnight, then dried. The dried product was ground up into a powder (about 50 microns). The product synthesized in Example No. 64, above, exhibited 9.7%, gel as determined by the gel content method described hereinabove.

The powder (25 g) was compounded with PEG 400 polyethylene glycol (25 g) to form a pressure-sensitive adhesive. PEG 400 polyethylene glycol is commercially available from Union Carbide under the trade designation Carbowax®, Sentry Grade, Polyethylene Glycol 400.

The tack of the pressure sensitive adhesive was determined by a modified spherical probe adhesion test that involves recording and analyzing the entire stress-strain behavior of a pressure sensitive adhesive during bonding and debonding of the probe. The test apparatus consists of a stainless steel spherical probe connected to a force transducer. The force transducer measures the force acting upon the spherical probe. The probe is moved up and down by a rotating screw driven by a stepping motor. A pressure sensitive adhesive sample is bonded adhesive side up to the test platform with a double-sided tape. During bonding of the probe to the pressure sensitive adhesive, the probe moves down and compresses the adhesive to a pre-determined force (i.e.—compression force). During the debonding process, the probe ascends and separates from the pressure sensitive adhesive sample and a pre-determined test speed. As the probe ascends, the adhesive sample becomes elongated and exerts a tensile force on the transducer. As the adhesive is further elongated, the stress increases in the adhesive until it reaches the interfacial strength between the probe and the adhesive, at which point the probe separates from the adhesive sample. The debonding strength of the adhesive sample is measured by the magnitude of the force and duration time of the probe. The pressure sensitive adhesive of Example No. 64 exhibited a tack value of 0.2303 N Force and 93.965 Nm ($\times 10^{-5}$) Energy. For a detailed description for the measurement of the tack of pressure sensitive adhesives, see "Avery Adhesive Test, AAT", *Adhesives Age*, Vol. 10, No. 10, pp.18–23 (1997).

Example Nos. 65–73 are examples of 1–1.5 mm thick pressure sensitive adhesives comprising poly 2-hydroxyethyl methacrylate powders blended with polyethylene glycol (PEG) 400 at a powder:PEG ratio of 1:2. The poly 2-hydroxyethyl methacrylate powders were prepared using different HEMA monomer sources. The tack and rheometrics of the pressure sensitive adhesives are reported in Table XIa, below.

TABLE XIa

Pressure Sensitive Adhesives of poly 2-hydroxyethyl methacrylate and polyethylene glycol

| | | | | | Rheometrics | | | |
|---|---|---|---|---|---|---|---|---|
| Ex. | % INT/ACT | % Gel | Force (N) | Energy Nm($10^{-5}$) | G' 0.1 rad/s dyne/cm × $10^4$ | G' 100 rad/s dyne/cm × $10^4$ | G" 0.1 rad/s dyne/cm × $10^4$ | G" 100 rad/s dyne/cm × $10^4$ |
| 65* | 0.1 | 98.5 | 0.1312 | 3.4189 | 17.8420 | 2.0629 | 33.9930 | 6.7337 |
| 66* | 0.8 | 85.8 | 0.1827 | 15.0930 | 4.3926 | 0.7101 | 13.9110 | 5.0524 |
| 67* | 1.6 | 76.5 | 0.1535 | 17.6360 | 1.8554 | 0.3791 | 8.6069 | 4.4009 |
| 68** | 0.1 | 97.1 | 0.2215 | 6.2883 | 17.2500 | 2.6183 | 31.8970 | 5.3206 |
| 69** | 0.8 | 63.8 | 0.1332 | 67.8080 | 0.8932 | 0.6411 | 10.5470 | 5.0334 |
| 70** | 1.6 | 14.8 | 0.0531 | 153.7300 | 0.0817 | 0.1560 | 6.3956 | 4.6835 |
| 71*** | 0.1 | 96.7 | 0.1476 | 4.4343 | 2.8014 | 0.3687 | 5.4282 | 1.0169 |
| 72*** | 0.8 | 73.5 | 0.1757 | 33.4000 | 3.2641 | 1.0506 | 18.8390 | 8.1289 |
| 73*** | 1.6 | 59.2 | 0.0500 | 22.6810 | 0.2321 | 0.1943 | 6.6193 | 5.1477 |

HEMA sources:
*Rohm & Haas OGM,
**Mitsubishi SEC,
***RohmTech BM 903

Table XIa shows poly HEMA powder prepared with various sources of HEMA monomers, and various ratios of initiator/activator can be formulated with polyethylene glycol to form a pressure sensitive adhesive. The pressure sensitive adhesives have good adhesive performance (i.e.— high Force and Energy as measured by the ATT test described hereinabove).

Example No. 74–82 in Table VIb are examples of pressure sensitive adhesives comprising poly 2-hydroxyethyl methacrylate powders blended with polyethylene glycol (PEG) 400 at powder:PEG ratios of 1:1, 1:2 and 1:3. The poly 2-hydroxyethyl methacrylate powders were prepared with HEMA monomers commerically available from Mitsubishi. The tack, including Force (N) and Energy (Nm×$10^{-5}$) of the pressure sensitive adhesives are reported in Table XIb, below.

TABLE XIb

Pressure Sensitive Adhesives of poly 2-hydroxyethyl methacrylate* and polyethylene glycol

| Example* | % INT/ACT | % Gel | Powder:PEG | Force (N) | Energy Nm(×$10^{-5}$) |
|---|---|---|---|---|---|
| 74 | 0.1 | 95.7 | 1:1 | 0.1504 | 2.8897 |
| 75 | 0.8 | 66.2 | 1:1 | 0.2626 | 14.8660 |
| 76 | 1.6 | 9.7 | 1:1 | 0.2303 | 93.9650 |
| 77 | 0.1 | 97.1 | 1:2 | 0.2215 | 6.2883 |
| 78 | 0.8 | 63.8 | 1:2 | 0.1332 | 67.8080 |
| 79 | 1.6 | 14.8 | 1:2 | 0.0531 | 153.7300 |
| 80 | 0.1 | 95.7 | 1:3 | 0.1184 | 4.1229 |
| 81 | 0.8 | 66.2 | 1:3 | 0.0450 | 21.1301 |
| 82 | 1.6 | 9.7 | 1:3 | elongation too high | |

*Mitsubishi SEC

Table XIb shows that low gel polyHEMA powder prepared with the Mitsubishi HEMA monomers formulated with lower levels polyethylene glycol provides the highest ATT values. Because of the low gel content of the polyHEMA powder, it is possible to reduce the amount of plasticizer used to prepare a pressure sensitive adhesive.

Example Nos. 83–89 in Table XII are poly 2-hydroxyethyl methacrylate polymers prepared by blending 2-hydroxyethyl methacrylate monomers having less than 3 weight percent alkylene glycol methacrylate impurities and containing 0.05–0.1% by weight of ethylene glycol dimethacrylate with 2-hydroxyethyl methacrylate monomers having less than 3 weight percent alkylene glycol methacrylate impurities and greater than 0.15% by weight of ethylene glycol dimethacrylate. The poly HEMA powders were formulated with PEG at a ratio of one part poly HEMA powder to two parts PEG plasticizer. As shown in Table XII, poly 2-hydroxyethyl methacrylate prepared according to the present invention having a % INT/ACT from about 0.1 to about 1.6 exhibit a Force of about 0.12 N to about 0.2 N and an Energy of about 4.7 Nm (×$10^{-5}$) to about 40 Nm (×$10^{-5}$).

The rheometrics for the poly 2-hydroxyethyl methacrylate was also evaluated. A detailed description relating to the measurement of modulus is provided in "Viscoelastic Windows of Pressure-Sensitive Adhesives", E. P. Chang, *J. Adhesion*, Vol. 34 pp. 189–200 (1991), and "Viscoelastic Properties of Pressure-Sensitive Adhesives", E. P. Chang, *J. Adhesion*, Vol. 60 pp. 233–248, (1997). Briefly, dynamic shear modulus (G) can be resolved into components of storage modulus (G') plus dissipation modulus (G"). In dynamic mechanical testing with varying amplitude and frequency, sinusoidal deformation is applied to the test sample and the resultant torque or force transmitted through the sample to a transducer is measured. Both the strain and the torque signals are amplified and input to a central processing unit where the phase angle between the strain and torque and the dynamic modulus are calculated using programs related to the test mode and sample geometry selected.

TABLE XII

| | | | | Avery Tack | | Rheometrics dyne/cm × $10^4$ | | | |
|---|---|---|---|---|---|---|---|---|---|
| Ex. | HEMA OGM*:SEC** | % INT/ACT | % Gel | Force (N) | Energy Nm($10^{-5}$) | G' 0.1 rad/s | G' 100 rad/s | G" 0.1 rad/s | G" 100 rad/s |
| 83 | 50:50 | 0.1 | 93.3 | 0.1391 | 4.719 | 17.0220 | 30.8500 | 2.2762 | 5.1992 |
| 84 | 50:50 | 0.8 | 75.8 | 0.1999 | 26.223 | 2.8982 | 12.8910 | 0.8750 | 4.8199 |

TABLE XII-continued

| | | | | Avery Tack | | Rheometrics dyne/cm × $10^4$ | | | |
|---|---|---|---|---|---|---|---|---|---|
| Ex. | HEMA OGM*:SEC** | % INT/ACT | % Gel | Force (N) | Energy Nm($10^{-5}$) | G' 0.1 rad/s | G' 100 rad/s | G" 0.1 rad/s | G" 100 rad/s |
| 85 | 50:50 | 1.6 | 58.9 | 0.1290 | 39.340 | 0.5618 | 5.5776 | 0.2443 | 3.1655 |
| 86 | 75:25 | 0.1 | 92.0 | 0.1464 | 4.998 | 6.5796 | 13.2500 | 0.9310 | 2.6070 |
| 87 | 75:25 | 0.8 | 79.7 | 0.1560 | 14.257 | 5.2057 | 17.9140 | 1.1070 | 5.9671 |
| 88 | 75:25 | 0.8 | 78.8 | 0.1675 | 15.706 | 5.8394 | 20.0840 | 1.2593 | 6.8274 |
| 89 | 75:25 | 1.6 | 62.2 | 0.1647 | 24.573 | 1.4052 | 9.5499 | 0.4508 | 5.0231 |

*Mitsubishi SEC
**Rohm & Haas Rocryl OGM

Table XII shows that pressure sensitive adhesives having adequate ATT performance can be prepared using a combination of low gel producing HEMA monomers (Mitsubishi) and high gel producing HEMA monomers (Rohrn & Haas).

EXAMPLE 90

A copolymer of comprising 67.5 weight % 2-hydroxyethyl methacrylate, 30 weight % 4-hydroxybutyl acrylate and 2.5 weight % methacrylic acid was prepared according to the following recipe and procedure:

Recipe

| Reactor Charge | |
|---|---|
| 2-Hydroxyethyl Methacrylate (Mitsubishi) | 270 g |
| 4-Hydroxybutyl acrylate | 120 g |
| Methacrylic acid | 10 g |
| Ethanol | 373.2 g |
| Deionized Water | 373.2 g |
| Initiator Charge | |
| Deionized Water | 10 g |
| Sodium Persulfate (0.5%) | 2 g |
| Cook-Off Initiator #1 | |
| Deionized Water | 5 g |
| Ethanol | 5 g |
| Sodium Persulfate | 0.4 g |
| Cook off Initiator #2 | |
| Deionized Water | 5 g |
| Ethanol | 5 g |
| Sodium Persulfate | 0.4 g |
| Cook off Initiator #3 | |
| Deionized Water | 5 g |
| Ethanol | 5 g |
| Sodium Metabisulfite | 0.4 g |
| Total | 1189.6 g |

Polymerization Procedure

1. The Reactor Charge was weighed out into a flask and introduced into a reaction kettle.
2. The Reactor Charge was heated with a 80° C. jacket and with $N_2$ purging of the Reactor Charge.
3. The initiator charge was added to the heated and $N_2$ purged Reactor Charge.
4. After about 10 minutes, the polymerization was started for a three hour period, while maintaining a jacket temperature of about 83° C.
5. After about three hours of polymerization, Cook Off Initiator #1 was added into the reaction kettle.
6. One hour after adding Cook Off Initiator #1, Cook Off Initiator #2 was added to the reaction kettle.
7. One hour after adding Cook Off Initiator #2, Cook Off Initiator #3 was added to the reaction kettle.
8. After an additional hour of heating, the reaction kettle was cooled.

The water insoluble copolymer prepared in Example 1 was subjected to a leaching process to remove residual unreacted monomer. The leaching process is described below.

Leaching Process 1096 grams of polymer solution was transferred to the leaching vessel and the leaching process to remove unreacted monomer is described below.

| First Leach | |
|---|---|
| Water added to precipitate polymer | 2200 g |
| Decant off effluent | 1708.8 g |
| Ethanol to redissolve | 160 g |
| Second Leach | |
| Water added to precipitate polymer | 1100 g |
| Decant off effluent | 989.4 g |
| Ethanol to redissolve | 120 g |
| Third Leach | |
| Water added to precipitate polymer | 1100 g |
| Decant off effluent | 1366.5 g |
| Ethanol to redissolve | 140 g |

After completion of the leaching process of the copolymer product of Example 90, the pH of the leached copolymer was adjusted with 4 grams of a 30% ammonium hydroxide solution. The copolymer product was diluted to 5% total solids content (TSC) with water. By visual inspection, the pH adjusted copolymer product appeared slightly hazy in solution. The pH of the diluted copolymer was further adjusted by the addition of 2 grams of 30% by weight ammonium hydroxide solution. The copolymer product was again diluted to 5% TSC with water. The pH of the copolymer product was measured to be 6.6 and, upon visual inspection, the copolymer product appeared clear in solution.

The leached and pH adjusted water soluble copolymer product synthesized in Example No. 90, above, exhibited the following properties:

| | |
|---|---|
| Viscosity, cPs | 864 |
| % Solids content | 20.9% |
| % Ethanol | 15.9% |
| % Water | 63.2% |
| Residual monomer | |
| 2-Hydroxyethyl Methacrylate | <15 ppm |
| 4-Hydroxybutyl Acrylate | <10 ppm |
| Methacrylic Acid | <0.01% |

The presence of any gel formation in the copolymer product was determined by visually inspecting the polymerization mixture or a poured thin film of the copolymer product for any particulate. The appearance of the copolymer product in this example was determined utilizing a visual test looking at the clarity of a poured thin film of the copolymer solution.

The percent solids in the copolymer product was measured by accurately weighing a small aluminum dish, then accurately weighing about 1 gram of wet copolymer sample. The aluminum dish with the sample was dried under an infrared lamp for about 15 minutes. The aluminum dish with the dried sample was cooled and then accurately reweighed. The weight of the dried sample divided by the wet sample multiplied by 100 is the percent total solids in the sample.

The viscosity of the copolymer product was measured under ambient conditions (23–25° C.) with a Brookfield LV Viscometer using an appropriate spindle and speed for the measured viscosity. The viscosity units are centipoise, cPs.

The protocols described hereinabove that were used to measure and evaluate the appearance, percent solids and viscosity of the copolymer product of Example No. 90 apply to all of the below described inventive polymer examples produced according to the present invention, and the comparative examples, unless specifically indicated. The polymerization procedure described above for Example 1, was used for Example Nos. 91–95, 99 and 100 and Comparative Example Nos. 96–98, unless otherwise indicated.

EXAMPLE 91

A copolymer of comprising 97.5 weight % 2-hydroxyethyl methacrylate and 2.5 weight % methacrylic acid was prepared according to the following recipe:

Recipe

| | |
|---|---|
| Reactor Charge | |
| 2-Hydroxyethyl Methacrylate (Mitsubishi) | 292.5 g |
| Methacrylic acid | 7.5 g |
| Ethanol | 280 g |
| Deionized Water | 280 g |
| Initiator Charge | |
| Deionized Water | 10 g |
| Sodium Persulfate (0.5%) | 1.5 g |
| Cook-Off Initiator #1 | |
| Deionized Water | 5 g |
| Ethanol | 5 g |
| Sodium Persulfate | 0.3 g |

-continued

| | |
|---|---|
| Cook off Initiator #2 | |
| Deionized Water | 5 g |
| Ethanol | 5 g |
| Sodium Persulfate | 0.3 g |
| Cook off Initiator #3 | |
| Deionized Water | 5 g |
| Ethanol | 5 g |
| Sodium Metabisulfite | 0.3 g |
| Total | 902.4 g |

The water insoluble copolymer of Example 91 was subjected to a leaching process to remove the residual unreacted monomer. The leaching process is described below.

Leaching Process 755 grams of polymer solution was transferred to the leaching vessel and the polymer was subjected to the leaching process to remove unreacted monomer, as described below.

| | |
|---|---|
| First Leach | |
| Water added to precipitate polymer | 1510 g |
| Decant off effluent | 1207.7 g |
| Ethanol to redissolve | 120 g |
| Second Leach | |
| Water added to precipitate polymer | 755 g |
| Decant off effluent | 986.2 g |
| Ethanol to redissolve | 90 g |
| Third Leach | |
| Water added to precipitate polymer | 755 g |
| Decant off effluent | 832.5 g |
| Ethanol to redissolve | 75 g |

After completion of the leaching of the copolymer product of Example 91, the leached copolymer was pH adjusted with 4 grams of a 30% ammonium hydroxide solution and 96 grams of deionized water. The pH of the copolymer product was measured to be 6.4. The copolymer was diluted to 5% total solids content with water and, upon visual inspection, the copolymer product appeared clear in solution.

The leached and pH adjusted copolymer product synthesized in Example No. 91, above, exhibited the following properties:

| | |
|---|---|
| Viscosity, cPs | 12,140 |
| % Solids content | 23.7% |
| % Ethanol | 10.3% |
| % Water | 66% |
| Residual monomers | |
| 2-Hydroxyethyl Methacrylate | <15 ppm |
| Methacrylic Acid | <0.01% |

EXAMPLE 92

A copolymer comprising 97.5 weight % 2-hydroxyethyl methacrylate and 2.5 weight % methacrylic acid was prepared according to the following recipe:

| Reactor Charge | |
| --- | --- |
| 2-Hydroxyethyl Methacrylate (Mitsubishi) | 292.5 g |
| Methacrylic acid | 7.5 g |
| Ethanol | 280 g |
| Deionized Water | 280 g |
| Initiator Charge | |
| Deionized Water | 10 g |
| Sodium Persulfate (0.5%) | 1.5 g |
| Cook-Off Initiator #1 | |
| Deionized Water | 5 g |
| Ethanol | 5 g |
| Sodium Persulfate | 0.3 g |
| Cook off Initiator #2 | |
| Deionized Water | 5 g |
| Ethanol | 5 g |
| Sodium Persulfate | 0.3 g |
| Cook off Initiator #3 | |
| Deionized Water | 5 g |
| Ethanol | 5 g |
| Sodium Metabisulfite | 0.3 g |
| Total | 902.4 g |

The water insoluble copolymer of Example 92 was subjected to a leaching process to remove residual unreacted monomer. According to this example, the copolymer product was redissolved in propylene glycol instead of ethanol. The leaching process is described below.

Leaching Process 800 grams of polymer solution was transferred to the leaching vessel and the polymer product was subjected to the leaching process to remove unreacted monomer, as described below.

| First Leach | |
| --- | --- |
| Water added to precipitate polymer | 1600 g |
| Decant off effluent | 1397 g |
| Propylene glycol to redissolve | 165 g |
| Second Leach | |
| Water added to precipitate polymer | 800 g |
| Decant off effluent | 1132 g |
| Propylene glycol to redissolve | 140 g |
| Third Leach | |
| Water added to precipitate polymer | 800 g |
| Decant off effluent | 996 g |
| Propylene glycol to redissolve | 121 g |

After completion of the leaching of the copolymer product of Example 92, the leached copolymer was pH adjusted with 3 grams of a 30% ammonium hydroxide solution in 300 grams of deionized water. The pH of the copolymer product was measured to be 5.8. The copolymer was diluted to 5% total solids content with water and, upon visual inspection, the copolymer product appeared clear in solution. The leached and pH adjusted copolymer product synthesized in Example No. 92, above, exhibited the following properties:

| Viscosity, cPs | 61,600 |
| --- | --- |
| % Solids content | 25.5% |
| % Water | 64.2% |
| % Propylene glycol | 10.3% |
| % Ethanol | 0.7% |
| Residual monomers | |
| 2-Hydroxyethyl Methacrylate | <0.59% |
| Methacrylic Acid | <0.01% |

EXAMPLE 93

A copolymer of comprising 67.5 weight % 2-hydroxyethyl methacrylate, 30 weight % 4-hydroxybutyl acrylate and 2.5 weight % methacrylic acid was prepared according to the following recipe:

Recipe

| Reactor Charge | |
| --- | --- |
| 2-Hydroxyethyl Methacrylate (Mitsubishi) | 337.5 g |
| 4-Hydroxybutyl acrylate | 150 g |
| Methacrylic acid | 12.5 g |
| Ethanol | 466.5 g |
| Deionized Water | 466.5 g |
| Initiator Charge | |
| Deionized Water | 12.5 g |
| Sodium Persulfate (0.5%) | 2.5 g |
| Cook-Off Initiator #1 | |
| Deionized Water | 6.25 g |
| Ethanol | 6.25 g |
| Sodium Persulfate | 0.5 g |
| Cook off Initiator #2 | |
| Deionized Water | 6.25 g |
| Ethanol | 6.25 g |
| Sodium Persulfate | 0.5 g |
| Cook off Initiator #3 | |
| Deionized Water | 6.25 g |
| Ethanol | 6.25 g |
| Sodium Metabisulfite | 0.5 g |
| Total | 1487 g |

Leaching Process 1000 grams of polymer solution was transferred to the leaching vessel and the polymer product was subjected to a leaching process to remove unreacted monomer, as described below.

| First Leach | |
| --- | --- |
| Water added to precipitate polymer | 2000 g |
| Decant off effluent | 1225 g |
| Ethanol to redissolve | 145 g |
| Second Leach | |
| Water added to precipitate polymer | 1000 g |
| Decant off effluent | 1189 g |
| Ethanol to redissolve | 145 g |

-continued

| Third Leach | |
|---|---|
| Water added to precipitate polymer | 1000 g |
| Decant off effluent | 1024 g |
| Ethanol to redissolve | 145 g |
| Fourth Leach | |
| Water added to precipitate polymer | 1000 g |
| Decant off effluent | 1093 g |

After completion of the leaching of the copolymer product of Example 93, the copolymer product was both redissolved and the pH adjusted in a solution of 4 grams of a 30% ammonium hydroxide solution in 150 grams of deionized water. The copolymer product was diluted to 5% total solids content (TSC) with water. Upon visual inspection the copolymer product appeared slightly hazy. The pH of the diluted copolymer was further adjusted by the addition of 2.4 grams of 30% by weight ammonium hydroxide solution. The copolymer product was again diluted to 5% TSC with water. The pH was the copolymer product was measured to be 7.6 and, upon visual inspection, the copolymer product appeared clear in solution. The leached and pH adjusted copolymer product synthesized in Example No. 93, above, exhibited the following properties:

| Viscosity, cPs | 1904 |
|---|---|
| % Solids content | 18.4% |
| % Ethanol | 4% |
| % Water | 81.2% |
| Residual monomers | |
| 2-Hydroxyethyl Methacrylate | <15 ppm |
| 4-Hydroxybutyl acrylate | <20 ppm |
| Methacrylic Acid | <0.01% |

EXAMPLE 94

329 grams of polymer product prepared in accordance with Example 4 was transferred to the leaching vessel and the polymer product was subjected to a leaching process to remove unreacted monomer, as described below.

Leaching Process

| First Leach | |
|---|---|
| Water added to precipitate polymer | 660 g |
| Decant off effluent | 472.6 g |
| Ethanol to redissolve | 50 g |
| Second Leach | |
| Water added to precipitate polymer | 330 g |
| Decant off effluent | 349.6 g |
| Ethanol to redissolve | 50 g |
| Third Leach | |
| Water added to precipitate polymer | 330 g |
| Decant off effluent | 407.6 g |

After completion of the leaching of the copolymer product, the copolymer product was both redissolved and pH adjusted with a solution containing 1.7 grams of triethanolamine in 50 grams of deionized water and. Upon visual inspection, the copolymer product appeared hazy in solution. The copolymer product was diluted to 5% TSC with water. Upon visual inspection, the copolymer product appeared milky in solution. The pH of the diluted copolymer product was adjusted with an additional 2.1 grams of triethanolamine. The pH of the copolymer was measured as 6.3. The copolymer product was added diluted to 5% TSC and, upon visual inspection, the copolymer was clear in solution. The leached and pH adjusted copolymer product of Example No. 94 exhibited the following properties:

| Viscosity, cPs | 6480 |
|---|---|
| % Solids content | 20.3% |
| % Ethanol | 8.3% |
| % Water | 71.4% |
| Residual monomers | |
| 2-Hydroxyethyl Methacrylate | <30 ppm |
| 4-Hydroxybutyl acrylate | <20 ppm |
| methacrylic acid | 0.1% |

EXAMPLE 95

A copolymer comprising 60 weight % 2-hydroxyethyl methacrylate, 30 weight % 4-hydroxybutyl acrylate and 10 weight % methacrylic acid was prepared according to the following recipe:

Recipe

| Reactor Charge | |
|---|---|
| 2-Hydroxyethyl Methacrylate (Mitsubishi) | 240 g |
| 4-Hydroxybutyl acrylate | 120 g |
| Methacrylic acid | 40 g |
| Ethanol | 373.2 g |
| Deionized Water | 373.2 g |
| Initiator Charge | |
| Deionized Water | 10 g |
| Sodium Persulfate (0.5%) | 2 g |
| Cook-Off Initiator #1 | |
| Deionized Water | 5 g |
| Ethanol | 5 g |
| Sodium Persulfate | 0.4 g |
| Cook off Initiator #2 | |
| Deionized Water | 5 g |
| Ethanol | 5 g |
| Sodium Persulfate | 0.4 g |
| Cook off Initiator #3 | |
| Deionized Water | 5 g |
| Ethanol | 5 g |
| Sodium Metabisulfite | 0.4 g |
| Total | 1189.6 g |

The water insoluble was subjected to a leaching process to remove residual unreacted monomer. The leaching process is described below.

Leaching Process 1078 grams of copolymer solution of Example 95 was transferred to the leaching vessel and copolymer was subjected to a leaching process to remove unreacted monomer, as described below.

| First Leach | | |
|---|---|---|
| Water to precipitate polymer | 2000 | g |
| Decant off effluent | 1515.4 | g |
| Ethanol to redissolve | 150 | g |
| Second Leach | | |
| Water to precipitate polymer | 1000 | g |
| Decant off effluent | 924.8 | g |
| Ethanol to redissolve | 150 | g |
| Third Leach | | |
| Water to precipitate polymer | 1000 | g |
| Decant off effluent | 1184.5 | g |
| Ethanol to redissolve | 150 | g |

After completion of the leaching of the copolymer product of Example 95, the pH of the leached copolymer was adjusted with 4 grams of a 30% ammonium hydroxide solution. Upon visual inspection, the copolymer product appeared clear in solution. The copolymer product was then diluted to 5% TSC with water. Upon visual inspection, the copolymer product precipitated out of solution. The pH of the diluted copolymer product was adjusted with 6 grams of a 30% ammonium hydroxide solution. The pH of the was measured as 6.5. The copolymer product was again diluted to 5% TSC and, upon visual inspection, the copolymer was clear in solution. The leached and pH adjusted copolymer product synthesized in Example No. 95, above, exhibited the following properties:

| | | |
|---|---|---|
| Viscosity, cPs | 2920 | |
| % Solids content | 19.9% | |
| % Ethanol | 20.5% | |
| % Water | 59.6% | |
| Residual monomers | | |
| 2-Hydroxyethyl Methacrylate | <30 ppm | |
| 4-Hydroxybutyl acrylate | <20 ppm | |
| Methacrylic Acid | <0.01% | |

COMPARATIVE EXAMPLE 96

A copolymer of 67.5 weight % 2-hydroxyethyl methacrylate, 30 weight % 4-hydroxybutyl acrylate and 2.5 weight % methacrylic acid was prepared according to the following recipe. The copolymer of Comparative Example 96 was prepared with a 2-hydroxyethyl methacrylate monomer source containing 0.17 weight % ethylene glycol dimethacrylate impurity, which monomer source is commercially available from Rohm & Haas under the tradename Rocryl 400:

Recipe

| Reactor Charge | | |
|---|---|---|
| 2-Hydroxyethyl Methacrylate (Rohm & Haas) | 270 | g |
| 4-Hydroxybutyl acrylate | 120 | g |
| Methacrylic acid | 10 | g |
| Ethanol | 373.2 | g |
| Deionized Water | 373.2 | g |
| Initiator Charge | | |
| Deionized Water | 10 | g |
| Sodium Persulfate (0.5%) | 2 | g |
| Cook-Off Initiator #1 | | |
| Deionized Water | 5 | g |
| Ethanol | 5 | g |
| Sodium Persulfate | 0.4 | g |
| Cook off Initiator #2 | | |
| Deionized Water | 5 | g |
| Ethanol | 5 | g |
| Sodium Persulfate | 0.4 | g |
| Cook off Initiator #3 | | |
| Deionized Water | 5 | g |
| Ethanol | 5 | g |
| Sodium Metabisulfite | 0.4 | g |
| Total | 1189.6 | g |

The copolymer of Comparative Example 96 formed a hydrogel during the polymerization process. Without being bound to any particular theory, the inventor surmises that the formation of the hydrogel can be attributed to the higher level of ethylene glycol dimethacrylate present in the 2-hydroxyethyl methacrylate monomer source from Rohm & Haas.

COMPARATIVE EXAMPLE 97

A homopolymer of 2-hydroxyethyl methacrylate was prepared according to the following recipe:

Recipe

| Reactor Charge | | |
|---|---|---|
| 2-Hydroxyethyl Methacrylate (Mitsubishi) | 233.4 | g |
| Ethanol | 225.5 | g |
| Deionized Water | 225.5 | g |
| Initiator Charge | | |
| Deionized Water | 3.8 | g |
| Sodium Persulfate (0.5%) | 1.17 | g |
| Cook-Off Initiator #1 | | |
| Deionized Water | 1.9 | g |
| Ethanol | 1.9 | g |
| Sodium Persulfate | 0.23 | g |
| Cook off Initiator #2 | | |
| Deionized Water | 1.9 | g |
| Ethanol | 1.9 | g |
| Sodium Persulfate | 0.23 | g |
| Cook off Initiator #3 | | |
| Deionized Water | 1.9 | g |
| Ethanol | 1.9 | g |
| Sodium Metabisulfite | 0.23 | g |
| Total | 701.46 | g |

Leaching Process 550 grams of the water insoluble copolymer prepared in accordance with Comparative Example 97 was transferred to the leaching vessel and the copolymer was subjected to a leaching process to remove unreacted monomer, as described below.

| First Leach | |
|---|---|
| Water added to precipitate polymer | 1100 g |
| Decant off effluent | 1361 g |
| Ethanol to redissolve | 100 g |
| Second Leach | |
| Water added to precipitate polymer | 1000 g |
| Decant off effluent | 1105 g |
| Ethanol to redissolve | 100 g |
| Third Leach | |
| Water added to precipitate polymer | 1000 g |
| Decant off effluent | 1271 g |
| Ethanol to redissolve | 125 g |

After completion of the leaching of the homopolymer of Comparative Example 97, the pH of 90 grams of the leached homopolymer was adjusted 9.7 with 0.28 grams of a 30% ammonium hydroxide solution. The pH adjusted homopolymer product was diluted to 5% TSC with water. Upon dilution, the homopolymer precipitated out of solution, indicating that it was insoluble in water. The leached and pH adjusted copolymer product synthesized in Comparative Example No. 97 exhibited the following properties:

| | |
|---|---|
| Viscosity, cPs | 1900 |
| % Solids content | 25.6% |
| % Ethanol | 16.5% |
| % Water | 57.9% |
| Residual monomers | |
| 2-Hydroxyethyl Methacrylate | <0.01% |
| 4-Hydroxybutyl acrylate | <0.01% |

COMPARATIVE EXAMPLE 98

A copolymer comprising 67 weight % 2-hydroxyethyl methacrylate and 33 weight % 4-hydroxybutyl acrylate was prepared in accordance with the following recipe:

Recipe

| Reactor Charge | |
|---|---|
| 2-Hydroxyethyl Methacrylate (Mitsubishi) | 16.6 Kg |
| 4-Hydroxybutyl acrylate | 8.3 Kg |
| Ethanol | 24.1 Kg |
| Deionized Water | 24.1 Kg |
| Initiator Charge | |
| Deionized Water | 0.4 Kg |
| Sodium Persulfate (0.5%) | 0.13 Kg |
| Cook-Off Initiator #1 | |
| Deionized Water | 0.2 Kg |
| Ethanol | 0.2 Kg |
| Sodium Persulfate | 0.025 Kg |

| -continued | |
|---|---|
| Cook off Initiator #2 | |
| Deionized Water | 0.2 Kg |
| Ethanol | 0.2 Kg |
| Sodium Persulfate | 0.025 Kg |
| Cook off Initiator #3 | |
| Deionized Water | 0.2 Kg |
| Ethanol | 0.2 Kg |
| Sodium Persulfate (Metabisulfite) | 0.025 Kg |
| Total | 75 Kg |

Leaching Process 75 kilograms of the water insoluble copolymer prepared in accordance with Comparative Example 98 was transferred to the leaching vessel and the copolymer was subjected to a leaching process to remove unreacted monomer is described below.

| First Leach | |
|---|---|
| Water to precipitate polymer | 94.1 Kg |
| Decant off effluent | 93.3 Kg |
| Ethanol to redissolve | 7.5 Kg |
| Second Leach | |
| Water to precipitate polymer | 74.8 Kg |
| Decant off effluent | 92.9 Kg |
| Ethanol to redissolve | 7.5 Kg |
| Third Leach | |
| Water to precipitate polymer | 74.8 Kg |
| Decant off effluent | 81.5 Kg |
| Ethanol to redissolve | 9.4 Kg |

After completion of the leaching of the copolymer product of Comparative Example 98, the pH of 90 grams of the leached copolymer adjusted with 0.022 grams of a 30% ammonium hydroxide solution. The pH was measured to be about 8.38. Upon visual inspection, the copolymer was clear in solution. The copolymer was then diluted to 5% TSC with water. Upon visual inspection, the diluted copolymer product of Comparative Example 98 appeared as a milky dispersion in solution. The leached and pH adjusted copolymer product synthesized in Comparative Example No. 98, above, exhibited the following properties:

| | |
|---|---|
| Viscosity, cPs | 660 |
| % Solids content | 23.6% |
| % Ethanol | 23.5% |
| % Water | 52.9% |
| Residual monomers | |
| 2-Hydroxyethyl Methacrylate | <50 ppm |
| 4-Hydroxybutyl acrylate | <10 ppm |

EXAMPLE 99

1625 grams of the leached, water insoluble copolymer prepared in accordance with Comparative Example 99 was transferred to the leaching vessel and the copolymer was subjected to an additional leaching process to replace the ethanol with propylene glycol, as described below.

2$^{nd}$ Leaching Process

| First Leach | |
|---|---|
| Water to precipitate polymer | 1625 g |
| Decant off effluent | 1999 g |
| Propylene glycol to redissolve | 150 g |
| Second Leach | |
| Water to precipitate polymer | 1625 g |
| Decant off effluent | 2048 g |
| Propylene glycol to redissolve | 100 g |
| Third Leach | |
| Water to precipitate polymer | 1625 g |
| Decant off effluent | 1788 g |
| Propylene glycol to redissolve | 100 g |

The leached copolymer product of Example 99 exhibited the following properties:

| | |
|---|---|
| Viscosity, cPs | 80,000 |
| pH | 3.2 |
| % Solids content | 29% |
| % Water | 59% |
| % Propylene glycol | 12% |
| % Ethanol | 0.3% |
| Residual monomers | |
| 2-Hydroxyethyl Methacrylate | 90 ppm |
| 4-Hydroxybutyl acrylate | 25 ppm |

EXAMPLE 100

A homopolymer of 2-hydroxyethyl methacrylate was prepared in accordance with the following recipe:

Recipe

| Reactor Charge | |
|---|---|
| 2-Hydroxyethyl Methacrylate (Mitsubishi) | 24.96 Kg |
| Ethanol | 24.12 Kg |
| Deionized Water | 24.12 Kg |
| Initiator Charge | |
| Deionized Water | 0.41 Kg |
| Sodium Persulfate (0.5%) | 0.13 Kg |
| Cook-Off Initiator #1 | |
| Deionized Water | 0.2 Kg |
| Ethanol | 0.2 Kg |
| Sodium Persulfate | 0.025 Kg |
| Cook off Initiator #2 | |
| Deionized Water | 0.2 Kg |
| Ethanol | 0.2 Kg |
| Sodium Persulfate | 0.025 Kg |
| Cook off Initiator #3 | |
| Deionized Water | 0.2 Kg |
| Ethanol | 0.2 Kg |
| Sodium Metabisulfite | 0.025 Kg |
| Total | 74.59 Kg |
| % Solids Content | 34.7% |

The was subjected to a leaching process to remove the residual unreacted 2-hydroxyethyl methacrylate monomer.

Leaching Process 75 kilograms of the water insoluble homopolymer prepared in accordance with Example 100 was transferred to the leaching vessel and the polymer was subject to a leaching process to remove unreacted monomer, as described below.

| First Leach | |
|---|---|
| Water to precipitate polymer | 131.6 Kg |
| Decant off effluent | 105.3 Kg |
| Ethanol to redissolve | 8.5 Kg |
| Second Leach | |
| Water to precipitate polymer | 73.5 Kg |
| Decant off effluent | 84.4 Kg |
| Ethanol to redissolve | 7.8 Kg |
| Third Leach | |
| Water to precipitate polymer | 74.9 Kg |
| Decant off effluent | 84.1 Kg |
| Ethanol to redissolve | 9.4 Kg |

2$^{nd}$ Leaching Process 1624 grams of leached polymer prepared in accordance with Example 100 was transferred to the leaching vessel and the polymer was subjected to a further leaching process to replace the ethanol with propylene glycol, as described below.

| First Leach | |
|---|---|
| Water to precipitate polymer | 1624 g |
| Decant off effluent | 2062 g |
| Propylene glycol to redissolve | 154 g |
| Second Leach | |
| Water to precipitate polymer | 1624 g |
| Decant off effluent | 1873 g |
| Propylene glycol to redissolve | 108 g |
| Third Leach | |
| Water to precipitate polymer | 1624 g |
| Decant off effluent | 1718 g |
| Propylene glycol to redissolve | 103 g |

The leached copolymer product synthesized in Example 100, above, exhibited the following properties:

| | |
|---|---|
| Viscosity, cPs | 540,000 |
| pH | 3.5 |
| % Solids content | 28% |
| % Water | 58% |
| % Propylene glycol | 14% |
| % Ethanol | 0.5% |
| Residual monomer | |
| 2-Hydroxyethyl Methacrylate | <10 ppm |

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. A method for the preparation of a powdered poly 2-hydroxyethyl methacrylate comprising:
    introducing monomeric 2-hydroxyethyl methacrylate containing ethylene glycol dimethacrylate impurities of at least 0.05% by weight of the monomer into water;
    polymerizing the 2-hydroxyethyl methacrylate to form a polymerization mixture;
    drying said polymerization mixture; and
    forming a powder from said dried polymerization mixture.

2. The method of claim 1, wherein the monomeric 2-hydroxyethyl methacrylate contains ethylene glycol dimethacrylate impurities in the range of about 0.05 to about 0.1% by weight of the monomer.

3. The method of claim 1, wherein the monomeric 2-hydroxyethyl methacrylate contains impurities in a total amount of no more than about 3% by weight of the monomer, and wherein the impurities are selected from the group consisting of ethylene glycol dimethacrylate, diethylene glycol monomethacrylate, methacrylic acid and mixtures thereof.

4. The method of claim 1, comprising introducing monomeric 2-hydroxyethyl methacrylate containing ethylene glycol dimethacrylate impurities of at least 0.05% by weight of the monomer, an initiator, and an activator into water, wherein the amount of each of the initiator and activator is in the range of about 0.1 to about 1.6%, based on the weight of the monomer.

5. The method of claim 1, further comprising blending the powder with a polyalkylene glycol to prepare a hydrophilic pressure sensitive adhesive.

6. The method of claim 5, wherein the polyalkylene glycol is selected from the group consisting of polyethylene glycol, polypropylene glycol and copolymers of ethylene glycol and propylene glycol, and mixtures thereof.

7. The method of claim 5, wherein the ratio of powder to polyalkylene glycol in is the range of about 1:1 to about 1:3.

8. The method of claim 2, wherein the monomeric 2-hydroxyethyl methacrylate contains impurities in a total amount of no more than about 3% by weight of the monomer, and wherein the impurities are selected from the group consisting of ethylene glycol dimethacrylate, diethylene glycol monomethacrylate, methacrylic acid and mixtures thereof.

9. The method of claim 2, comprising introducing monomeric 2-hydroxyethyl methacrylate containing ethylene glycol dimethacrylate impurities in the range of about 0.05 to about 0.1% by weight of the monomer, an initiator, and an activator into water, wherein the amount of each of the initiator and activator is in the range of about 0.1 to about 1.6%, based on the weight of the monomer.

10. The method of claim 2, further comprising blending the powder with a polyalkylene glycol to prepare a hydrophilic pressure sensitive adhesive.

11. The method of claim 10, wherein the polyalkylene glycol is selected from the group consisting of polyethylene glycol, polypropylene glycol and copolymers of ethylene glycol and propylene glycol, and mixtures thereof.

12. The method of claim 10, wherein the ratio of powder to polyalkylene glycol in is the range of about 1:1 to about 1:3.

13. The method of claim 1, wherein the monomeric 2-hydroxyethyl methacrylate introduced into the water includes a blend of monomeric 2-hydroxyethyl methacrylate containing ethylene glycol dimethacrylate impurities in the range of about 0.05 to about 0.1% by weight of the monomer and monomeric 2-hydroxyethyl methacrylate containing ethylene glycol dimethacrylate impurities in an amount greater than about 0.15% by weight of the monomer.

14. The method of claim 13, wherein the monomeric 2-hydroxyethyl methacrylate contains impurities in a total amount of no more than about 3% by weight of the monomer, and wherein the impurities are selected from the group consisting of ethylene glycol dimethacrylate, diethylene glycol monomethacrylate, methacrylic acid and mixtures thereof.

15. The method of claim 13, comprising introducing monomeric 2-hydroxyethyl methacrylate containing ethylene glycol dimethacrylate impurities in the range of about 0.05 to about 0.1% by weight of the monomer, monomeric 2-hydroxyethyl methacrylate containing ethylene glycol dimethacrylate impurities in an amount greater than about 0.15% by weight of the monomer, an initiator, and an activator into water, wherein the amount of each of the initiator and activator is in the range of about 0.1 to about 1.6%, based on the weight of the monomer.

16. The method of claim 13, further comprising blending the powder with a polyalkylene glycol to prepare a hydrophilic pressure sensitive adhesive.

17. The method of claim 16, wherein the polyalkylene glycol is selected from the group consisting of polyethylene glycol, polypropylene glycol and copolymers of ethylene glycol and propylene glycol, and mixtures thereof.

18. The method of claim 16, wherein the ratio of powder to polyalkylene glycol in is the range of about 1:1 to about 1:3.

19. A hydrophilic pressure sensitive adhesive prepared by the method of claim 5.

20. A hydrophilic pressure sensitive adhesive prepared by the method of claim 10.

21. A hydrophilic pressure sensitive adhesive prepared by the method of claim 16.

22. A cosmetic composition or skin care composition containing the powder prepared by the method of claim 1.

23. A cosmetic composition or skin care composition containing the powder prepared by the method of claim 2.

24. A method of coating a substrate comprising applying the hydrophilic pressure sensitive adhesive prepared by the method of claim 5 to the substrate.

25. A method of coating a substrate comprising applying the hydrophilic pressure sensitive adhesive prepared by the method of claim 10 to the substrate.

26. A method of coating a substrate comprising applying the hydrophilic pressure sensitive adhesive prepared by the method of claim 16 to the substrate.

27. The method of claim 1, wherein the monomeric 2-hydroxyethyl methacrylate contains ethylene glycol dimethacrylate impurities in the range of about 0.05 to about 0.17% by weight of the monomer.

* * * * *